(12) United States Patent
Nicholas et al.

(10) Patent No.: US 11,147,548 B2
(45) Date of Patent: Oct. 19, 2021

(54) ADAPTER ASSEMBLY AND LOADING UNITS FOR SURGICAL STAPLING DEVICES

(71) Applicant: Covidien LP, Mansfield, MA (US)

(72) Inventors: David Nicholas, Trumbull, CT (US);
John Beardsley, Wallingford, CT (US);
Russell Pribanic, Roxbury, CT (US)

(73) Assignee: Covidien LP, Mansfield, MA (US)

( * ) Notice: Subject to any disclaimer, the term of this patent is extended or adjusted under 35 U.S.C. 154(b) by 190 days.

(21) Appl. No.: 16/171,893

(22) Filed: Oct. 26, 2018

(65) Prior Publication Data

US 2019/0059879 A1 Feb. 28, 2019

Related U.S. Application Data

(63) Continuation of application No. 14/703,956, filed on May 5, 2015, now Pat. No. 10,117,650.

(51) Int. Cl.
*A61B 17/072* (2006.01)
*A61B 17/068* (2006.01)
(Continued)

(52) U.S. Cl.
CPC .......... *A61B 17/068* (2013.01); *A61B 17/072* (2013.01); *A61B 17/07207* (2013.01);
(Continued)

(58) Field of Classification Search
CPC ................ A61B 17/068; A61B 17/072; A61B 17/07214; A61B 17/115; A61B 2017/07214; A61B 2017/07278; A61B 2017/07228; A61B 2017/00477; A61B 17/07207; A61B 2017/00398; A61B 2017/2927; A61B 2017/2929; A61B 2017/2947
(Continued)

(56) References Cited

U.S. PATENT DOCUMENTS 3,079,606 A 3/1963 Bobrov et al.
3,490,675 A 1/1970 Green et al.
(Continued)

FOREIGN PATENT DOCUMENTS

CN 101011285 A 8/2007
CN 101015471 A 8/2007
(Continued)

OTHER PUBLICATIONS

Extended European Search Report corresponding to International Application No. EP 15 15 1076.5 dated Apr. 22, 2015.
(Continued)

*Primary Examiner* — Scott A Smith
(74) *Attorney, Agent, or Firm* — Carter, DeLuca & Farrell, LLP

(57) ABSTRACT

A surgical apparatus is provided. The surgical apparatus includes a proximal body portion, a distal body portion selectively articulable relative to the proximal body portion at an articulation joint, and a first drive gear disposed within the distal body portion. The distal body portion has a diameter and a length. The length of the distal body portion is substantially the same as the diameter of the distal body portion.

17 Claims, 30 Drawing Sheets

(51) Int. Cl.
  *A61B 17/29* (2006.01)
  *A61B 17/00* (2006.01)
(52) U.S. Cl.
  CPC ............ *A61B 2017/0046* (2013.01); *A61B 2017/00398* (2013.01); *A61B 2017/00734* (2013.01); *A61B 2017/00964* (2013.01); *A61B 2017/07214* (2013.01); *A61B 2017/07278* (2013.01); *A61B 2017/2929* (2013.01); *A61B 2017/2947* (2013.01)
(58) Field of Classification Search
  USPC ............ 227/19, 175.1, 175.2, 176.1, 180.1; 606/1, 139, 219
  See application file for complete search history.

(56) References Cited

U.S. PATENT DOCUMENTS

| | | | |
|---|---|---|---|
| 3,499,591 | A | 3/1970 | Green |
| 3,777,538 | A | 12/1973 | Heatherly et al. |
| 3,882,854 | A | 5/1975 | Hulka et al. |
| 4,027,510 | A | 6/1977 | Hiltebrandt |
| 4,086,926 | A | 5/1978 | Green et al. |
| 4,241,861 | A | 12/1980 | Fleischer |
| 4,244,372 | A | 1/1981 | Kapitanov et al. |
| 4,429,695 | A | 2/1984 | Green |
| 4,505,414 | A | 3/1985 | Filipi |
| 4,520,817 | A | 6/1985 | Green |
| 4,589,413 | A | 5/1986 | Malyshev et al. |
| 4,596,351 | A | 6/1986 | Fedotov et al. |
| 4,602,634 | A | 7/1986 | Barkley |
| 4,605,001 | A | 8/1986 | Rothfuss et al. |
| 4,608,981 | A | 9/1986 | Rothfuss et al. |
| 4,610,383 | A | 9/1986 | Rothfuss et al. |
| 4,633,861 | A | 1/1987 | Chow et al. |
| 4,633,874 | A | 1/1987 | Chow et al. |
| 4,671,445 | A | 6/1987 | Barker et al. |
| 4,700,703 | A | 10/1987 | Resnick et al. |
| 4,703,887 | A | 11/1987 | Clanton et al. |
| 4,728,020 | A | 3/1988 | Green et al. |
| 4,752,024 | A | 6/1988 | Green et al. |
| 4,784,137 | A | 11/1988 | Kulik et al. |
| 4,863,088 | A | 9/1989 | Redmond et al. |
| 4,869,415 | A | 9/1989 | Fox |
| 4,892,244 | A | 1/1990 | Fox et al. |
| 4,955,959 | A | 9/1990 | Tompkins et al. |
| 4,978,049 | A | 12/1990 | Green |
| 4,991,764 | A | 2/1991 | Mericle |
| 5,014,899 | A | 5/1991 | Presty et al. |
| 5,031,814 | A | 7/1991 | Tompkins et al. |
| 5,040,715 | A | 8/1991 | Green et al. |
| 5,065,929 | A | 11/1991 | Schulze et al. |
| 5,071,430 | A | 12/1991 | de Salis et al. |
| 5,074,454 | A | 12/1991 | Peters |
| 5,083,695 | A | 1/1992 | Foslien et al. |
| 5,084,057 | A | 1/1992 | Green et al. |
| 5,106,008 | A | 4/1992 | Tompkins et al. |
| 5,111,987 | A | 5/1992 | Moeinzadeh et al. |
| 5,129,570 | A | 7/1992 | Schulze et al. |
| 5,141,144 | A | 8/1992 | Foslien et al. |
| 5,156,315 | A | 10/1992 | Green et al. |
| 5,156,614 | A | 10/1992 | Green et al. |
| 5,163,943 | A | 11/1992 | Mohiuddin et al. |
| 5,170,925 | A | 12/1992 | Madden et al. |
| 5,171,247 | A | 12/1992 | Hughett et al. |
| 5,173,133 | A | 12/1992 | Morin et al. |
| 5,180,092 | A | 1/1993 | Crainich |
| 5,188,274 | A | 2/1993 | Moeinzadeh et al. |
| 5,220,928 | A | 6/1993 | Oddsen et al. |
| 5,221,036 | A | 6/1993 | Takase |
| 5,242,457 | A | 9/1993 | Akopov et al. |
| 5,246,156 | A | 9/1993 | Rothfuss et al. |
| 5,253,793 | A | 10/1993 | Green et al. |
| 5,263,629 | A | 11/1993 | Trumbull et al. |
| RE34,519 | E | 1/1994 | Fox et al. |
| 5,275,323 | A | 1/1994 | Schulze et al. |
| 5,282,807 | A | 2/1994 | Knoepfler |
| 5,289,963 | A | 3/1994 | McGarry et al. |
| 5,307,976 | A | 5/1994 | Olson et al. |
| 5,308,576 | A | 5/1994 | Green et al. |
| 5,312,023 | A | 5/1994 | Green et al. |
| 5,318,221 | A | 6/1994 | Green et al. |
| 5,326,013 | A | 7/1994 | Green et al. |
| 5,328,077 | A | 7/1994 | Lou |
| 5,330,486 | A | 7/1994 | Wilk |
| 5,332,142 | A | 7/1994 | Robinson et al. |
| 5,336,232 | A | 8/1994 | Green et al. |
| 5,344,061 | A | 9/1994 | Crainich |
| 5,352,238 | A | 10/1994 | Green et al. |
| 5,356,064 | A | 10/1994 | Green et al. |
| 5,358,506 | A | 10/1994 | Green et al. |
| 5,364,001 | A | 11/1994 | Bryan |
| 5,364,002 | A | 11/1994 | Green et al. |
| 5,364,003 | A | 11/1994 | Williamson, IV |
| 5,366,133 | A | 11/1994 | Geiste |
| 5,376,095 | A | 12/1994 | Ortiz |
| 5,379,933 | A | 1/1995 | Green et al. |
| 5,381,943 | A | 1/1995 | Allen et al. |
| 5,382,255 | A | 1/1995 | Castro et al. |
| 5,383,880 | A | 1/1995 | Hooven |
| 5,389,098 | A | 2/1995 | Tsuruta et al. |
| 5,395,033 | A | 3/1995 | Byrne et al. |
| 5,395,034 | A | 3/1995 | Allen et al. |
| 5,397,046 | A | 3/1995 | Savage et al. |
| 5,397,324 | A | 3/1995 | Carroll et al. |
| 5,403,312 | A | 4/1995 | Yates et al. |
| 5,405,072 | A | 4/1995 | Zlock et al. |
| 5,407,293 | A | 4/1995 | Crainich |
| 5,413,268 | A | 5/1995 | Green et al. |
| 5,415,334 | A | 5/1995 | Williamson et al. |
| 5,415,335 | A | 5/1995 | Knodell, Jr. |
| 5,417,361 | A | 5/1995 | Williamson, IV |
| 5,423,471 | A | 6/1995 | Mastri et al. |
| 5,425,745 | A | 6/1995 | Green et al. |
| 5,431,322 | A | 7/1995 | Green et al. |
| 5,431,323 | A | 7/1995 | Smith et al. |
| 5,433,721 | A | 7/1995 | Hooven et al. |
| 5,441,193 | A | 8/1995 | Gravener |
| 5,445,304 | A | 8/1995 | Plyley et al. |
| 5,447,265 | A | 9/1995 | Vidal et al. |
| 5,452,836 | A * | 9/1995 | Huitema ............ A61B 17/072 227/176.1 |
| 5,452,837 | A | 9/1995 | Williamson, IV et al. |
| 5,456,401 | A | 10/1995 | Green et al. |
| 5,464,300 | A | 11/1995 | Crainich |
| 5,465,895 | A | 11/1995 | Knodel et al. |
| 5,467,911 | A | 11/1995 | Tsuruta et al. |
| 5,470,007 | A | 11/1995 | Plyley et al. |
| 5,470,010 | A | 11/1995 | Rothfuss et al. |
| 5,472,132 | A | 12/1995 | Savage et al. |
| 5,474,566 | A | 12/1995 | Alesi et al. |
| 5,476,206 | A | 12/1995 | Green et al. |
| 5,478,003 | A | 12/1995 | Green et al. |
| 5,480,089 | A | 1/1996 | Blewett |
| 5,482,197 | A | 1/1996 | Green et al. |
| 5,484,095 | A | 1/1996 | Green et al. |
| 5,484,451 | A | 1/1996 | Akopov et al. |
| 5,485,947 | A | 1/1996 | Olson et al. |
| 5,485,952 | A | 1/1996 | Fontayne |
| 5,486,185 | A | 1/1996 | Freitas et al. |
| 5,487,499 | A | 1/1996 | Sorrentino et al. |
| 5,487,500 | A | 1/1996 | Knodel et al. |
| 5,489,058 | A | 2/1996 | Plyley et al. |
| 5,490,856 | A | 2/1996 | Person et al. |
| 5,497,933 | A | 3/1996 | DeFonzo et al. |
| 5,501,689 | A | 3/1996 | Green et al. |
| 5,505,363 | A | 4/1996 | Green et al. |
| 5,507,426 | A | 4/1996 | Young et al. |
| 5,518,163 | A | 5/1996 | Hooven |
| 5,518,164 | A | 5/1996 | Hooven |
| 5,529,235 | A | 6/1996 | Boiarski et al. |
| 5,531,744 | A | 7/1996 | Nardella et al. |
| 5,535,934 | A | 7/1996 | Boiarski et al. |
| 5,535,935 | A | 7/1996 | Vidal et al. |

(56) References Cited

U.S. PATENT DOCUMENTS

| | | |
|---|---|---|
| 5,535,937 A | 7/1996 | Boiarski et al. |
| 5,540,375 A | 7/1996 | Bolanos et al. |
| 5,542,594 A | 8/1996 | McKean et al. |
| 5,549,628 A | 8/1996 | Cooper et al. |
| 5,549,637 A | 8/1996 | Crainich |
| 5,551,622 A | 9/1996 | Yoon |
| 5,553,675 A | 9/1996 | Pitzen et al. |
| 5,553,765 A | 9/1996 | Knodel et al. |
| 5,554,164 A | 9/1996 | Wilson et al. |
| 5,554,169 A | 9/1996 | Green et al. |
| 5,560,530 A | 10/1996 | Bolanos et al. |
| 5,560,532 A | 10/1996 | DeFonzo et al. |
| 5,562,239 A | 10/1996 | Boiarski et al. |
| 5,562,241 A | 10/1996 | Knodel et al. |
| 5,562,682 A | 10/1996 | Oberlin et al. |
| 5,562,701 A | 10/1996 | Huiterna et al. |
| 5,564,615 A | 10/1996 | Bishop et al. |
| 5,571,116 A | 11/1996 | Bolanos et al. |
| 5,573,169 A | 11/1996 | Green et al. |
| 5,573,543 A | 11/1996 | Akopov et al. |
| 5,575,799 A | 11/1996 | Bolanos et al. |
| 5,575,803 A | 11/1996 | Cooper et al. |
| 5,577,654 A | 11/1996 | Bishop |
| 5,579,107 A | 11/1996 | Wright et al. |
| 5,584,425 A | 12/1996 | Savage et al. |
| 5,586,711 A | 12/1996 | Plyley et al. |
| 5,588,580 A | 12/1996 | Paul et al. |
| 5,588,581 A | 12/1996 | Conlon et al. |
| 5,597,107 A | 1/1997 | Knodel et al. |
| 5,601,224 A | 2/1997 | Bishop et al. |
| 5,607,095 A | 3/1997 | Smith et al. |
| 5,609,560 A | 3/1997 | Ichikawa et al. |
| 5,615,820 A | 4/1997 | Viola |
| 5,618,291 A | 4/1997 | Thompson et al. |
| 5,624,452 A | 4/1997 | Yates |
| 5,626,587 A | 5/1997 | Bishop et al. |
| 5,628,446 A | 5/1997 | Geiste et al. |
| 5,630,539 A | 5/1997 | Plyley et al. |
| 5,630,540 A | 5/1997 | Blewett |
| 5,630,541 A | 5/1997 | Williamson, IV et al. |
| 5,632,432 A | 5/1997 | Schulze et al. |
| 5,634,584 A | 6/1997 | Okorocha et al. |
| 5,636,780 A | 6/1997 | Green et al. |
| 5,645,209 A | 7/1997 | Green et al. |
| 5,647,526 A | 7/1997 | Green et al. |
| 5,651,491 A | 7/1997 | Heaton et al. |
| 5,653,373 A | 8/1997 | Green et al. |
| 5,653,374 A | 8/1997 | Young et al. |
| 5,653,721 A | 8/1997 | Knodel et al. |
| 5,655,698 A | 8/1997 | Yoon |
| 5,657,921 A | 8/1997 | Young et al. |
| 5,658,300 A | 8/1997 | Bito et al. |
| 5,662,258 A | 9/1997 | Knodel et al. |
| 5,662,259 A | 9/1997 | Yoon |
| 5,662,260 A | 9/1997 | Yoon |
| 5,662,662 A | 9/1997 | Bishop et al. |
| 5,662,666 A | 9/1997 | Onuki et al. |
| 5,665,085 A | 9/1997 | Nardella |
| 5,667,517 A | 9/1997 | Hooven |
| 5,669,544 A | 9/1997 | Schulze et al. |
| 5,673,840 A | 10/1997 | Schulze et al. |
| 5,673,841 A | 10/1997 | Schulze et al. |
| 5,673,842 A | 10/1997 | Bittner et al. |
| 5,676,674 A | 10/1997 | Bolanos et al. |
| 5,680,981 A | 10/1997 | Mililli et al. |
| 5,680,982 A | 10/1997 | Schulze et al. |
| 5,680,983 A | 10/1997 | Plyley et al. |
| 5,690,269 A | 11/1997 | Bolanos et al. |
| 5,692,668 A | 12/1997 | Schulze et al. |
| 5,697,542 A | 12/1997 | Knodel et al. |
| 5,702,409 A | 12/1997 | Rayburn et al. |
| 5,704,534 A | 1/1998 | Huitema et al. |
| 5,706,997 A | 1/1998 | Green et al. |
| 5,709,334 A | 1/1998 | Sorrentino et al. |
| 5,711,472 A | 1/1998 | Bryan |
| 5,713,505 A | 2/1998 | Huitema |
| 5,715,988 A | 2/1998 | Palmer |
| 5,716,366 A | 2/1998 | Yates |
| 5,718,359 A | 2/1998 | Palmer et al. |
| 5,725,536 A | 3/1998 | Oberlin et al. |
| 5,725,554 A | 3/1998 | Simon et al. |
| 5,728,110 A | 3/1998 | Vidal et al. |
| 5,732,806 A | 3/1998 | Foshee et al. |
| 5,735,848 A | 4/1998 | Yates et al. |
| 5,743,456 A | 4/1998 | Jones et al. |
| 5,749,893 A | 5/1998 | Vidal et al. |
| 5,752,644 A | 5/1998 | Bolanos et al. |
| 5,762,255 A | 6/1998 | Chrisman et al. |
| 5,762,256 A | 6/1998 | Mastri et al. |
| 5,769,303 A | 6/1998 | Knodel et al. |
| 5,769,892 A | 6/1998 | Kingwell |
| 5,772,099 A | 6/1998 | Gravener |
| 5,772,673 A | 6/1998 | Cuny et al. |
| 5,779,130 A | 7/1998 | Alesi et al. |
| 5,779,131 A | 7/1998 | Knodel et al. |
| 5,779,132 A | 7/1998 | Knodel et al. |
| 5,782,396 A | 7/1998 | Mastri et al. |
| 5,782,397 A | 7/1998 | Koukline |
| 5,782,834 A | 7/1998 | Lucey et al. |
| 5,785,232 A | 7/1998 | Vidal et al. |
| 5,797,536 A | 8/1998 | Smith et al. |
| 5,797,537 A | 8/1998 | Oberlin et al. |
| 5,797,538 A | 8/1998 | Heaton et al. |
| 5,810,811 A | 9/1998 | Yates et al. |
| 5,810,855 A | 9/1998 | Rayburn et al. |
| 5,814,055 A | 9/1998 | Knodel et al. |
| 5,814,057 A | 9/1998 | Oi et al. |
| 5,816,471 A | 10/1998 | Plyley et al. |
| 5,817,109 A | 10/1998 | McGarry et al. |
| 5,820,009 A | 10/1998 | Melling et al. |
| 5,823,066 A | 10/1998 | Huitema et al. |
| 5,826,776 A | 10/1998 | Schulze et al. |
| 5,829,662 A | 11/1998 | Allen et al. |
| 5,833,695 A | 11/1998 | Yoon |
| 5,836,147 A | 11/1998 | Schnipke |
| 5,862,972 A | 1/1999 | Green et al. |
| 5,865,361 A | 2/1999 | Milliman et al. |
| 5,871,135 A | 2/1999 | Williamson, IV et al. |
| 5,873,873 A | 2/1999 | Smith et al. |
| 5,878,938 A | 3/1999 | Bittner et al. |
| 5,893,506 A | 4/1999 | Powell |
| 5,894,979 A | 4/1999 | Powell |
| 5,897,562 A | 4/1999 | Bolanos et al. |
| 5,901,895 A | 5/1999 | Heaton et al. |
| 5,911,352 A | 6/1999 | Racenet et al. |
| 5,911,353 A | 6/1999 | Bolanos et al. |
| 5,918,791 A | 7/1999 | Sorrentino et al. |
| 5,919,198 A | 7/1999 | Graves, Jr. et al. |
| 5,922,001 A | 7/1999 | Yoon |
| 5,931,847 A | 8/1999 | Bittner et al. |
| 5,941,442 A | 8/1999 | Geiste et al. |
| 5,954,259 A | 9/1999 | Viola et al. |
| 5,964,774 A | 10/1999 | McKean et al. |
| 5,980,510 A | 11/1999 | Tsonton et al. |
| 5,988,479 A | 11/1999 | Palmer |
| 6,004,335 A | 12/1999 | Vaitekunas et al. |
| 6,010,054 A | 1/2000 | Johnson et al. |
| 6,032,849 A | 3/2000 | Mastri et al. |
| 6,045,560 A | 4/2000 | McKean et al. |
| 6,063,097 A | 5/2000 | Oi et al. |
| 6,079,606 A | 6/2000 | Milliman et al. |
| 6,099,551 A | 8/2000 | Gabbay |
| 6,109,500 A | 8/2000 | Alli et al. |
| 6,131,789 A | 10/2000 | Schulze et al. |
| 6,131,790 A | 10/2000 | Piraka |
| 6,155,473 A | 12/2000 | Tompkins et al. |
| 6,165,169 A | 12/2000 | Panescu et al. |
| 6,197,017 B1 | 3/2001 | Brock et al. |
| 6,202,914 B1 | 3/2001 | Geiste et al. |
| 6,241,139 B1 | 6/2001 | Milliman et al. |
| 6,250,532 B1 | 6/2001 | Green et al. |
| 6,264,086 B1 | 7/2001 | McGuckin, Jr. |
| 6,264,087 B1 | 7/2001 | Whitman |
| 6,269,977 B1 | 8/2001 | Moore |

(56) References Cited

U.S. PATENT DOCUMENTS

| | | |
|---|---|---|
| 6,279,809 B1 | 8/2001 | Nicolo |
| 6,315,183 B1 | 11/2001 | Piraka |
| 6,315,184 B1 | 11/2001 | Whitman |
| 6,325,810 B1 | 12/2001 | Hamilton et al. |
| 6,330,965 B1 | 12/2001 | Milliman et al. |
| 6,391,038 B2 | 5/2002 | Vargas et al. |
| 6,398,797 B2 | 6/2002 | Bombard et al. |
| 6,436,097 B1 | 8/2002 | Nardella |
| 6,439,446 B1 | 8/2002 | Perry et al. |
| 6,443,973 B1 | 9/2002 | Whitman |
| 6,463,623 B2 | 10/2002 | Ahn et al. |
| 6,478,804 B2 | 11/2002 | Vargas et al. |
| 6,488,196 B1 | 12/2002 | Fenton, Jr. |
| 6,503,257 B2 | 1/2003 | Grant et al. |
| 6,505,768 B2 | 1/2003 | Whitman |
| 6,544,274 B2 | 4/2003 | Danitz et al. |
| 6,554,844 B2 | 4/2003 | Lee et al. |
| 6,565,554 B1 | 5/2003 | Niemeyer |
| 6,587,750 B2 | 7/2003 | Gerbi et al. |
| 6,592,597 B2 | 7/2003 | Grant et al. |
| 6,594,552 B1 | 7/2003 | Nowlin et al. |
| 6,602,252 B2 | 8/2003 | Mollenauer |
| 6,612,053 B2 | 9/2003 | Liao |
| 6,619,529 B2 | 9/2003 | Green et al. |
| D480,808 S | 10/2003 | Wells et al. |
| 6,644,532 B2 | 11/2003 | Green et al. |
| 6,656,193 B2 | 12/2003 | Grant et al. |
| 6,669,073 B2 | 12/2003 | Milliman et al. |
| 6,681,978 B2 | 1/2004 | Geiste et al. |
| 6,698,643 B2 | 3/2004 | Whitman |
| 6,716,232 B1 | 4/2004 | Vidal et al. |
| 6,722,552 B2 | 4/2004 | Fenton, Jr. |
| 6,731,473 B2 | 5/2004 | Li et al. |
| 6,743,240 B2 | 6/2004 | Smith et al. |
| 6,755,338 B2 | 6/2004 | Hahnen et al. |
| 6,783,524 B2 | 8/2004 | Anderson et al. |
| 6,786,382 B1 | 9/2004 | Hoffman |
| 6,808,262 B2 | 10/2004 | Chapoy et al. |
| 6,817,509 B2 | 11/2004 | Geiste et al. |
| 6,830,174 B2 | 12/2004 | Hillstead et al. |
| 6,835,199 B2 | 12/2004 | McGuckin, Jr. et al. |
| 6,843,403 B2 | 1/2005 | Whitman |
| RE38,708 E | 3/2005 | Bolanos et al. |
| 6,877,647 B2 | 4/2005 | Green et al. |
| 6,889,116 B2 | 5/2005 | Jinno |
| 6,905,057 B2 | 6/2005 | Swayze et al. |
| 6,945,444 B2 | 9/2005 | Gresham et al. |
| 6,953,138 B1 | 10/2005 | Dworak et al. |
| 6,953,139 B2 | 10/2005 | Milliman et al. |
| 6,959,852 B2 | 11/2005 | Shelton, IV et al. |
| 6,962,594 B1 | 11/2005 | Thevenet |
| 6,964,363 B2 | 11/2005 | Wales et al. |
| 6,978,921 B2 | 12/2005 | Shelton, IV et al. |
| 6,981,628 B2 | 1/2006 | Wales |
| 6,986,451 B1 | 1/2006 | Mastri et al. |
| 6,988,649 B2 | 1/2006 | Shelton, IV et al. |
| 6,991,627 B2 | 1/2006 | Madhani et al. |
| 6,994,714 B2 | 2/2006 | Vargas et al. |
| 7,000,818 B2 | 2/2006 | Shelton, IV et al. |
| 7,000,819 B2 | 2/2006 | Swayze et al. |
| 7,032,799 B2 | 4/2006 | Viola et al. |
| 7,044,352 B2 | 5/2006 | Shelton, IV et al. |
| 7,044,353 B2 | 5/2006 | Mastri et al. |
| 7,055,730 B2 | 6/2006 | Ehrenfels et al. |
| 7,055,731 B2 | 6/2006 | Shelton, IV et al. |
| 7,059,508 B2 | 6/2006 | Shelton, IV et al. |
| 7,070,083 B2 | 7/2006 | Jankowski |
| 7,083,075 B2 | 8/2006 | Swayze et al. |
| 7,097,089 B2 | 8/2006 | Marczyk |
| 7,111,769 B2 | 9/2006 | Wales et al. |
| 7,114,642 B2 | 10/2006 | Whitman |
| 7,121,446 B2 | 10/2006 | Arad et al. |
| 7,128,253 B2 | 10/2006 | Mastri et al. |
| 7,128,254 B2 | 10/2006 | Shelton, IV et al. |
| 7,140,527 B2 | 11/2006 | Ehrenfels et al. |
| 7,140,528 B2 | 11/2006 | Shelton, IV |
| 7,143,923 B2 | 12/2006 | Shelton, IV et al. |
| 7,143,924 B2 | 12/2006 | Scirica et al. |
| 7,143,925 B2 | 12/2006 | Shelton, IV et al. |
| 7,143,926 B2 | 12/2006 | Shelton, IV et al. |
| 7,147,138 B2 | 12/2006 | Shelton, IV |
| 7,159,750 B2 | 1/2007 | Racenet et al. |
| 7,168,604 B2 | 1/2007 | Milliman et al. |
| 7,172,104 B2 | 2/2007 | Scirica et al. |
| 7,188,758 B2 | 3/2007 | Viola et al. |
| 7,207,471 B2 | 4/2007 | Heinrich et al. |
| 7,213,736 B2 | 5/2007 | Wales et al. |
| 7,225,963 B2 | 6/2007 | Scirica |
| 7,225,964 B2 | 6/2007 | Mastri et al. |
| 7,238,195 B2 | 7/2007 | Viola |
| 7,246,734 B2 | 7/2007 | Shelton, IV |
| 7,258,262 B2 | 8/2007 | Mastri et al. |
| 7,278,562 B2 | 10/2007 | Mastri et al. |
| 7,278,563 B1 | 10/2007 | Green |
| 7,287,682 B1 | 10/2007 | Ezzat et al. |
| 7,293,685 B2 | 11/2007 | Ehrenfels et al. |
| 7,296,722 B2 | 11/2007 | Ivanko |
| 7,296,724 B2 | 11/2007 | Green et al. |
| 7,296,772 B2 | 11/2007 | Wang |
| 7,300,444 B1 | 11/2007 | Nielsen et al. |
| 7,303,107 B2 | 12/2007 | Milliman et al. |
| 7,303,108 B2 | 12/2007 | Shelton, IV |
| 7,308,998 B2 | 12/2007 | Mastri et al. |
| 7,326,232 B2 | 2/2008 | Viola et al. |
| 7,328,828 B2 | 2/2008 | Ortiz et al. |
| 7,328,829 B2 | 2/2008 | Arad et al. |
| 7,334,717 B2 | 2/2008 | Rethy et al. |
| 7,354,447 B2 | 4/2008 | Shelton, IV et al. |
| 7,357,287 B2 | 4/2008 | Shelton, IV et al. |
| 7,364,061 B2 | 4/2008 | Swayze et al. |
| 7,367,485 B2 | 5/2008 | Shelton, IV et al. |
| 7,377,928 B2 | 5/2008 | Zubik et al. |
| 7,380,695 B2 | 6/2008 | Doll et al. |
| 7,380,696 B2 | 6/2008 | Shelton, IV et al. |
| 7,396,356 B2 | 7/2008 | Mollenauer |
| 7,398,907 B2 | 7/2008 | Racenet et al. |
| 7,399,310 B2 | 7/2008 | Edoga et al. |
| 7,401,720 B1 | 7/2008 | Durrani |
| 7,401,721 B2 | 7/2008 | Holsten et al. |
| 7,404,508 B2 | 7/2008 | Smith et al. |
| 7,404,509 B2 | 7/2008 | Ortiz et al. |
| 7,407,074 B2 | 8/2008 | Ortiz et al. |
| 7,407,075 B2 | 8/2008 | Holsten et al. |
| 7,407,077 B2 | 8/2008 | Ortiz et al. |
| 7,407,078 B2 | 8/2008 | Shelton, IV et al. |
| 7,416,101 B2 | 8/2008 | Shelton, IV et al. |
| 7,419,080 B2 | 9/2008 | Smith et al. |
| 7,419,081 B2 | 9/2008 | Ehrenfels et al. |
| 7,419,495 B2 | 9/2008 | Menn et al. |
| 7,422,139 B2 | 9/2008 | Shelton, IV et al. |
| 7,424,965 B2 | 9/2008 | Racenet et al. |
| 7,431,189 B2 | 10/2008 | Shelton, IV et al. |
| 7,431,730 B2 | 10/2008 | Viola |
| 7,434,715 B2 | 10/2008 | Shelton, IV et al. |
| 7,434,716 B2 * | 10/2008 | Viola ............... A61B 17/07207 227/176.1 |
| 7,434,717 B2 | 10/2008 | Shelton, IV et al. |
| 7,438,208 B2 | 10/2008 | Larson |
| 7,438,209 B1 | 10/2008 | Hess et al. |
| 7,441,684 B2 | 10/2008 | Shelton, IV et al. |
| 7,441,685 B1 | 10/2008 | Boudreaux |
| 7,448,525 B2 | 11/2008 | Shelton, IV et al. |
| 7,451,904 B2 | 11/2008 | Shelton, IV |
| 7,455,208 B2 | 11/2008 | Wales et al. |
| 7,455,676 B2 | 11/2008 | Holsten et al. |
| 7,458,494 B2 | 12/2008 | Matsutani et al. |
| 7,461,767 B2 | 12/2008 | Viola et al. |
| 7,462,185 B1 | 12/2008 | Knodel |
| 7,464,846 B2 | 12/2008 | Shelton, IV et al. |
| 7,464,847 B2 | 12/2008 | Viola et al. |
| 7,464,848 B2 | 12/2008 | Green et al. |
| 7,464,849 B2 | 12/2008 | Shelton, IV et al. |
| 7,467,740 B2 | 12/2008 | Shelton, IV et al. |
| 7,472,814 B2 | 1/2009 | Mastri et al. |

(56) References Cited

U.S. PATENT DOCUMENTS

| | | | |
|---|---|---|---|
| 7,472,815 B2 | 1/2009 | Shelton, IV et al. |
| 7,472,816 B2 | 1/2009 | Holsten et al. |
| 7,473,258 B2 | 1/2009 | Clauson et al. |
| 7,481,347 B2 | 1/2009 | Roy |
| 7,481,348 B2 | 1/2009 | Marczyk |
| 7,481,349 B2 | 1/2009 | Holsten et al. |
| 7,481,824 B2 | 1/2009 | Boudreaux et al. |
| 7,487,899 B2 | 2/2009 | Shelton, IV et al. |
| 7,490,749 B2 | 2/2009 | Schall et al. |
| 7,494,039 B2 | 2/2009 | Racenet et al. |
| 7,500,979 B2 | 3/2009 | Hueil et al. |
| 7,503,474 B2 | 3/2009 | Hillstead et al. |
| 7,506,790 B2 | 3/2009 | Shelton, IV |
| 7,506,791 B2 | 3/2009 | Omaits et al. |
| 7,510,107 B2 | 3/2009 | Timm et al. |
| 7,513,408 B2 | 4/2009 | Shelton, IV et al. |
| 7,517,356 B2 | 4/2009 | Heinrich |
| 7,537,602 B2 | 5/2009 | Whitman |
| 7,543,729 B2 | 6/2009 | Ivanko |
| 7,543,730 B1 | 6/2009 | Marczyk |
| 7,543,731 B2 | 6/2009 | Green et al. |
| 7,552,854 B2 | 6/2009 | Wixey et al. |
| 7,556,185 B2 | 7/2009 | Viola |
| 7,556,186 B2 | 7/2009 | Milliman |
| 7,559,450 B2 | 7/2009 | Wales et al. |
| 7,559,452 B2 | 7/2009 | Wales et al. |
| 7,559,453 B2 | 7/2009 | Heinrich et al. |
| 7,559,937 B2 | 7/2009 | de la Torre et al. |
| 7,565,993 B2 | 7/2009 | Milliman et al. |
| 7,568,603 B2 | 8/2009 | Shelton, IV et al. |
| 7,568,604 B2 | 8/2009 | Ehrenfels et al. |
| 7,571,845 B2 | 8/2009 | Viola |
| 7,575,144 B2 | 8/2009 | Ortiz et al. |
| 7,584,880 B2 | 9/2009 | Racenet et al. |
| 7,588,174 B2 | 9/2009 | Holsten et al. |
| 7,588,175 B2 | 9/2009 | Timm et al. |
| 7,588,176 B2 | 9/2009 | Timm et al. |
| 7,588,177 B2 | 9/2009 | Racenet |
| 7,597,229 B2 | 10/2009 | Boudreaux et al. |
| 7,597,230 B2 | 10/2009 | Racenet et al. |
| 7,600,663 B2 | 10/2009 | Green |
| 7,604,150 B2 | 10/2009 | Boudreaux |
| 7,604,151 B2 | 10/2009 | Hess et al. |
| 7,607,557 B2 | 10/2009 | Shelton, IV et al. |
| 7,611,038 B2 | 11/2009 | Racenet et al. |
| 7,617,961 B2 | 11/2009 | Viola |
| 7,624,902 B2 | 12/2009 | Marczyk et al. |
| 7,624,903 B2 | 12/2009 | Green et al. |
| 7,631,793 B2 | 12/2009 | Rethy et al. |
| 7,631,794 B2 | 12/2009 | Rethy et al. |
| 7,635,073 B2 | 12/2009 | Heinrich |
| 7,635,074 B2 | 12/2009 | Olson et al. |
| 7,635,373 B2 | 12/2009 | Ortiz |
| 7,637,409 B2 | 12/2009 | Marczyk |
| 7,637,410 B2 | 12/2009 | Marczyk |
| 7,641,091 B2 | 1/2010 | Olson et al. |
| 7,641,095 B2 | 1/2010 | Viola |
| 7,644,848 B2 | 1/2010 | Swayze et al. |
| 7,648,055 B2 | 1/2010 | Marczyk |
| 7,651,017 B2 | 1/2010 | Ortiz et al. |
| 7,654,431 B2 | 2/2010 | Hueil et al. |
| 7,658,311 B2 | 2/2010 | Boudreaux |
| 7,658,312 B2 | 2/2010 | Vidal et al. |
| 7,665,646 B2 | 2/2010 | Prommersberger |
| 7,665,647 B2 | 2/2010 | Shelton, IV et al. |
| 7,669,746 B2 | 3/2010 | Shelton, IV |
| 7,670,334 B2 | 3/2010 | Hueil et al. |
| 7,673,780 B2 | 3/2010 | Shelton, IV et al. |
| 7,673,781 B2 | 3/2010 | Swayze et al. |
| 7,673,782 B2 | 3/2010 | Hess et al. |
| 7,673,783 B2 | 3/2010 | Morgan et al. |
| 7,678,121 B1 | 3/2010 | Knodel |
| 7,681,772 B2 | 3/2010 | Green et al. |
| 7,682,367 B2 | 3/2010 | Shah et al. |
| 7,682,368 B1 | 3/2010 | Bombard et al. |
| 7,690,547 B2 | 4/2010 | Racenet et al. |
| 7,694,865 B2 | 4/2010 | Scirica |
| 7,699,205 B2 | 4/2010 | Ivanko |
| 7,703,653 B2 | 4/2010 | Shah et al. |
| 7,721,931 B2 | 5/2010 | Shelton, IV et al. |
| 7,721,933 B2 | 5/2010 | Ehrenfels et al. |
| 7,721,935 B2 | 5/2010 | Racenet et al. |
| 7,726,537 B2 | 6/2010 | Olson et al. |
| 7,726,538 B2 | 6/2010 | Holsten et al. |
| 7,726,539 B2 | 6/2010 | Holsten et al. |
| 7,731,072 B2 | 6/2010 | Timm et al. |
| 7,735,703 B2 | 6/2010 | Morgan et al. |
| 7,738,971 B2 | 6/2010 | Swayze et al. |
| 7,740,159 B2 | 6/2010 | Shelton, IV et al. |
| 7,740,160 B2 | 6/2010 | Viola |
| 7,743,960 B2 | 6/2010 | Whitman et al. |
| 7,744,628 B2 | 6/2010 | Viola |
| 7,753,245 B2 | 7/2010 | Boudreaux et al. |
| 7,753,248 B2 | 7/2010 | Viola |
| 7,757,924 B2 | 7/2010 | Gerbi et al. |
| 7,757,925 B2 | 7/2010 | Viola et al. |
| 7,762,445 B2 | 7/2010 | Heinrich et al. |
| 7,766,209 B2 | 8/2010 | Baxter, III et al. |
| 7,766,210 B2 | 8/2010 | Shelton, IV et al. |
| 7,766,924 B1 | 8/2010 | Bombard et al. |
| 7,766,928 B2 | 8/2010 | Ezzat et al. |
| 7,770,774 B2 | 8/2010 | Mastri et al. |
| 7,770,775 B2 | 8/2010 | Shelton, IV et al. |
| 7,776,060 B2 | 8/2010 | Mooradian et al. |
| 7,780,055 B2 | 8/2010 | Scirica et al. |
| 7,784,662 B2 | 8/2010 | Wales et al. |
| 7,789,283 B2 | 9/2010 | Shah |
| 7,789,889 B2 | 9/2010 | Zubik et al. |
| 7,793,812 B2 | 9/2010 | Moore et al. |
| 7,793,814 B2 | 9/2010 | Racenet et al. |
| 7,794,475 B2 | 9/2010 | Hess et al. |
| 7,798,385 B2 | 9/2010 | Boyden et al. |
| 7,798,386 B2 | 9/2010 | Schall et al. |
| 7,799,039 B2 | 9/2010 | Shelton, IV et al. |
| 7,803,151 B2 | 9/2010 | Whitman |
| 7,810,690 B2 | 10/2010 | Bilotti et al. |
| 7,810,692 B2 | 10/2010 | Hall et al. |
| 7,810,693 B2 | 10/2010 | Broehl et al. |
| 7,815,090 B2 | 10/2010 | Marczyk |
| 7,815,091 B2 | 10/2010 | Marczyk |
| 7,815,092 B2 | 10/2010 | Whitman et al. |
| 7,819,296 B2 | 10/2010 | Hueil et al. |
| 7,819,297 B2 | 10/2010 | Doll et al. |
| 7,819,298 B2 | 10/2010 | Hall et al. |
| 7,819,299 B2 | 10/2010 | Shelton, IV et al. |
| 7,819,796 B2 | 10/2010 | Blake et al. |
| 7,819,896 B2 | 10/2010 | Racenet |
| 7,823,760 B2 | 11/2010 | Zemlok et al. |
| 7,823,761 B2 | 11/2010 | Boyden et al. |
| 7,824,426 B2 | 11/2010 | Racenet et al. |
| 7,828,186 B2 | 11/2010 | Wales |
| 7,828,187 B2 | 11/2010 | Green et al. |
| 7,828,188 B2 | 11/2010 | Jankowski |
| 7,828,189 B2 | 11/2010 | Holsten et al. |
| 7,832,408 B2 | 11/2010 | Shelton, IV et al. |
| 7,832,611 B2 | 11/2010 | Boyden et al. |
| 7,832,612 B2 | 11/2010 | Baxter et al. |
| 7,837,079 B2 | 11/2010 | Holsten et al. |
| 7,837,081 B2 | 11/2010 | Holsten et al. |
| 7,841,503 B2 | 11/2010 | Sonnenschein et al. |
| 7,845,533 B2 | 12/2010 | Marczyk et al. |
| 7,845,534 B2 | 12/2010 | Viola et al. |
| 7,845,535 B2 | 12/2010 | Scircia |
| 7,845,537 B2 | 12/2010 | Shelton, IV et al. |
| 7,845,538 B2 | 12/2010 | Whitman |
| 7,850,703 B2 | 12/2010 | Bombard et al. |
| 7,857,183 B2 | 12/2010 | Shelton, IV |
| 7,857,184 B2 | 12/2010 | Viola |
| 7,857,185 B2 | 12/2010 | Swayze |
| 7,857,186 B2 | 12/2010 | Baxter, III et al. |
| 7,861,906 B2 | 1/2011 | Doll et al. |
| 7,861,907 B2 | 1/2011 | Green et al. |
| 7,866,524 B2 | 1/2011 | Krehel |
| 7,866,525 B2 | 1/2011 | Scirica |

(56) References Cited

U.S. PATENT DOCUMENTS

| | | |
|---|---|---|
| 7,866,526 B2 | 1/2011 | Green et al. |
| 7,866,527 B2 | 1/2011 | Hall et al. |
| 7,866,528 B2 | 1/2011 | Olson et al. |
| 7,870,989 B2 | 1/2011 | Viola et al. |
| 7,886,952 B2 | 2/2011 | Scirica et al. |
| 7,891,532 B2 | 2/2011 | Mastri et al. |
| 7,891,533 B2 | 2/2011 | Green et al. |
| 7,891,534 B2 | 2/2011 | Wenchell et al. |
| 7,896,214 B2 | 3/2011 | Farascioni |
| 7,900,805 B2 | 3/2011 | Shelton, IV et al. |
| 7,901,416 B2 | 3/2011 | Nolan et al. |
| 7,905,380 B2 | 3/2011 | Shelton, IV et al. |
| 7,905,381 B2 | 3/2011 | Baxter, III et al. |
| 7,909,039 B2 | 3/2011 | Hur |
| 7,909,220 B2 | 3/2011 | Viola |
| 7,909,221 B2 | 3/2011 | Viola et al. |
| 7,909,224 B2 | 3/2011 | Prommersberger |
| 7,913,891 B2 | 3/2011 | Doll et al. |
| 7,913,893 B2 | 3/2011 | Mastri et al. |
| 7,914,543 B2 | 3/2011 | Roth et al. |
| 7,918,230 B2 | 4/2011 | Whitman et al. |
| 7,918,276 B2 | 4/2011 | Guignard et al. |
| 7,922,061 B2 | 4/2011 | Shelton, IV et al. |
| 7,922,063 B2 | 4/2011 | Zemlok et al. |
| 7,922,064 B2 | 4/2011 | Boyden et al. |
| 7,926,691 B2 | 4/2011 | Viola et al. |
| 7,926,692 B2 | 4/2011 | Racenet et al. |
| 7,934,628 B2 | 5/2011 | Wenchell et al. |
| 7,934,630 B2 | 5/2011 | Shelton, IV et al. |
| 7,934,631 B2 | 5/2011 | Balbierz et al. |
| 7,942,300 B2 | 5/2011 | Rethy et al. |
| 7,942,303 B2 | 5/2011 | Shah |
| 7,950,560 B2 | 5/2011 | Zemlok et al. |
| 7,950,561 B2 | 5/2011 | Aranyi |
| 7,950,562 B2 | 5/2011 | Beardsley et al. |
| 7,954,682 B2 | 6/2011 | Giordano et al. |
| 7,954,683 B1 | 6/2011 | Knodel et al. |
| 7,954,684 B2 | 6/2011 | Boudreaux |
| 7,954,685 B2 | 6/2011 | Viola |
| 7,954,686 B2 | 6/2011 | Baxter, III et al. |
| 7,954,687 B2 | 6/2011 | Zemlok et al. |
| 7,959,051 B2 | 6/2011 | Smith et al. |
| 7,963,431 B2 | 6/2011 | Scirica |
| 7,963,432 B2 | 6/2011 | Knodel et al. |
| 7,963,433 B2 | 6/2011 | Whitman et al. |
| 7,967,178 B2 | 6/2011 | Scirica et al. |
| 7,967,179 B2 | 6/2011 | Olson et al. |
| 7,967,180 B2 | 6/2011 | Scirica |
| 7,975,894 B2 | 7/2011 | Boyden et al. |
| 7,980,443 B2 | 7/2011 | Scheib et al. |
| 7,988,026 B2 | 8/2011 | Knodel et al. |
| 7,988,027 B2 | 8/2011 | Olson et al. |
| 7,988,028 B2 | 8/2011 | Farascioni et al. |
| 7,992,758 B2 | 8/2011 | Whitman et al. |
| 7,997,468 B2 | 8/2011 | Farascioni |
| 7,997,469 B2 | 8/2011 | Olson et al. |
| 8,002,795 B2 | 8/2011 | Beetel |
| 8,006,885 B2 | 8/2011 | Marczyk |
| 8,006,887 B2 | 8/2011 | Marczyk |
| 8,007,505 B2 | 8/2011 | Weller et al. |
| 8,007,513 B2 | 8/2011 | Nalagatla et al. |
| 8,011,550 B2 | 9/2011 | Aranyi et al. |
| 8,011,551 B2 | 9/2011 | Marczyk et al. |
| 8,011,552 B2 | 9/2011 | Ivanko |
| 8,011,553 B2 | 9/2011 | Mastri et al. |
| 8,011,555 B2 | 9/2011 | Tarinelli et al. |
| 8,012,170 B2 | 9/2011 | Whitman et al. |
| 8,015,976 B2 | 9/2011 | Shah |
| 8,016,177 B2 | 9/2011 | Bettuchi et al. |
| 8,016,178 B2 | 9/2011 | Olson et al. |
| 8,020,742 B2 | 9/2011 | Marczyk |
| 8,020,743 B2 | 9/2011 | Shelton, IV |
| 8,028,882 B2 | 10/2011 | Viola |
| 8,028,883 B2 | 10/2011 | Stopek |
| 8,028,884 B2 | 10/2011 | Sniffin et al. |
| 8,033,438 B2 | 10/2011 | Scirica |
| 8,033,440 B2 | 10/2011 | Wenchell et al. |
| 8,033,441 B2 | 10/2011 | Marczyk |
| 8,033,442 B2 | 10/2011 | Racenet et al. |
| 8,034,077 B2 | 10/2011 | Smith et al. |
| 8,035,487 B2 | 10/2011 | Malackowski |
| 8,038,044 B2 | 10/2011 | Viola |
| 8,038,045 B2 | 10/2011 | Bettuchi et al. |
| 8,052,024 B2 | 11/2011 | Viola et al. |
| 8,056,787 B2 | 11/2011 | Boudreaux et al. |
| 8,056,788 B2 | 11/2011 | Mastri et al. |
| 8,056,791 B2 | 11/2011 | Whitman |
| 8,061,577 B2 | 11/2011 | Racenet et al. |
| 8,066,166 B2 | 11/2011 | Demmy et al. |
| 8,070,033 B2 | 12/2011 | Milliman et al. |
| 8,070,034 B1 | 12/2011 | Knodel |
| 8,070,035 B2 | 12/2011 | Holsten et al. |
| 8,074,858 B2 | 12/2011 | Marczyk |
| 8,074,859 B2 | 12/2011 | Kostrzewski |
| 8,074,862 B2 | 12/2011 | Shah |
| 8,083,118 B2 | 12/2011 | Milliman et al. |
| 8,083,119 B2 | 12/2011 | Prommersberger |
| 8,083,120 B2 | 12/2011 | Shelton, IV et al. |
| 8,087,563 B2 | 1/2012 | Milliman et al. |
| 8,091,753 B2 | 1/2012 | Viola |
| 8,091,754 B2 | 1/2012 | Ehrenfels et al. |
| 8,091,756 B2 | 1/2012 | Viola |
| 8,092,493 B2 | 1/2012 | Marczyk |
| 8,096,459 B2 | 1/2012 | Ortiz et al. |
| 8,096,460 B2 | 1/2012 | Blier et al. |
| 8,100,309 B2 | 1/2012 | Marczyk |
| 8,100,310 B2 | 1/2012 | Zemlok |
| 8,102,008 B2 | 1/2012 | Wells |
| 8,113,406 B2 | 2/2012 | Holsten et al. |
| 8,113,407 B2 | 2/2012 | Holsten et al. |
| 8,113,408 B2 | 2/2012 | Wenchell et al. |
| 8,113,409 B2 | 2/2012 | Cohen et al. |
| 8,113,410 B2 | 2/2012 | Hall et al. |
| 8,123,101 B2 | 2/2012 | Racenet et al. |
| 8,127,975 B2 | 3/2012 | Olson et al. |
| 8,127,976 B2 | 3/2012 | Scirica et al. |
| 8,132,703 B2 | 3/2012 | Milliman et al. |
| 8,132,705 B2 | 3/2012 | Viola et al. |
| 8,132,706 B2 | 3/2012 | Marczyk et al. |
| 8,136,713 B2 | 3/2012 | Hathaway et al. |
| 8,141,762 B2 | 3/2012 | Bedi et al. |
| 8,152,041 B2 | 4/2012 | Kostrzewski |
| 8,157,148 B2 | 4/2012 | Scirica |
| 8,157,150 B2 | 4/2012 | Viola et al. |
| 8,157,151 B2 | 4/2012 | Ingmanson et al. |
| 8,157,152 B2 | 4/2012 | Holsten et al. |
| 8,162,197 B2 | 4/2012 | Mastri et al. |
| 8,167,185 B2 | 5/2012 | Shelton, IV et al. |
| 8,167,186 B2 | 5/2012 | Racenet et al. |
| 8,172,121 B2 | 5/2012 | Krehel |
| 8,172,124 B2 | 5/2012 | Shelton, IV et al. |
| 8,181,837 B2 | 5/2012 | Roy |
| 8,186,555 B2 | 5/2012 | Shelton, IV et al. |
| 8,186,557 B2 | 5/2012 | Cohen et al. |
| 8,186,558 B2 | 5/2012 | Sapienza |
| 8,186,559 B1 | 5/2012 | Whitman |
| 8,186,560 B2 | 5/2012 | Hess |
| 8,193,044 B2 | 6/2012 | Kenneth |
| 8,196,795 B2 | 6/2012 | Moore et al. |
| 8,196,796 B2 | 6/2012 | Shelton, IV et al. |
| 8,201,721 B2 | 6/2012 | Zemlok et al. |
| 8,205,619 B2 | 6/2012 | Shah et al. |
| 8,205,780 B2 | 6/2012 | Sorrentino et al. |
| 8,205,781 B2 | 6/2012 | Baxter, III et al. |
| 8,210,412 B2 | 7/2012 | Marczyk |
| 8,210,416 B2 | 7/2012 | Milliman et al. |
| 8,216,236 B2 | 7/2012 | Heinrich et al. |
| 8,220,688 B2 | 7/2012 | Laurent et al. |
| 8,220,690 B2 | 7/2012 | Hess |
| 8,225,979 B2 | 7/2012 | Farascioni et al. |
| 8,231,040 B2 | 7/2012 | Zemlok et al. |
| 8,231,041 B2 | 7/2012 | Marczyk et al. |
| 8,235,272 B2 | 8/2012 | Nicholas et al. |
| 8,235,273 B2 | 8/2012 | Olson et al. |

(56) References Cited

U.S. PATENT DOCUMENTS

| | | |
|---|---|---|
| 8,235,274 B2 | 8/2012 | Cappola |
| 8,236,010 B2 | 8/2012 | Ortiz et al. |
| 8,240,536 B2 | 8/2012 | Marczyk |
| 8,240,537 B2 | 8/2012 | Marczyk |
| 8,241,322 B2 | 8/2012 | Whitman et al. |
| 8,245,897 B2 | 8/2012 | Tzakis et al. |
| 8,245,898 B2 | 8/2012 | Smith et al. |
| 8,245,899 B2 | 8/2012 | Swensgard et al. |
| 8,245,931 B2 | 8/2012 | Shigeta |
| 8,252,009 B2 | 8/2012 | Weller et al. |
| 8,256,653 B2 | 9/2012 | Farascioni |
| 8,256,654 B2 | 9/2012 | Bettuchi et al. |
| 8,256,655 B2 | 9/2012 | Sniffin et al. |
| 8,256,656 B2 | 9/2012 | Milliman et al. |
| 8,267,300 B2 | 9/2012 | Boudreaux |
| 8,272,551 B2 | 9/2012 | Knodel et al. |
| 8,272,553 B2 | 9/2012 | Mastri et al. |
| 8,272,554 B2 | 9/2012 | Whitman et al. |
| 8,276,594 B2 | 10/2012 | Shah |
| 8,276,801 B2 | 10/2012 | Zemlok et al. |
| 8,281,973 B2 | 10/2012 | Wenchell et al. |
| 8,286,847 B2 | 10/2012 | Taylor |
| 8,286,848 B2 | 10/2012 | Wenchell et al. |
| 8,286,850 B2 | 10/2012 | Viola |
| 8,292,146 B2 | 10/2012 | Holsten et al. |
| 8,292,147 B2 | 10/2012 | Viola |
| 8,292,148 B2 | 10/2012 | Viola |
| 8,292,149 B2 | 10/2012 | Ivanko |
| 8,292,150 B2 | 10/2012 | Bryant |
| 8,292,151 B2 | 10/2012 | Viola |
| 8,292,152 B2 | 10/2012 | Milliman et al. |
| 8,292,153 B2 | 10/2012 | Jankowski |
| 8,292,154 B2 | 10/2012 | Marczyk |
| 8,292,155 B2 | 10/2012 | Shelton, IV et al. |
| 8,292,156 B2 | 10/2012 | Kostrzewski |
| 8,292,158 B2 | 10/2012 | Sapienza |
| 8,308,040 B2 | 11/2012 | Huang et al. |
| 8,308,041 B2 | 11/2012 | Kostrzewski |
| 8,308,042 B2 | 11/2012 | Aranyi |
| 8,308,043 B2 | 11/2012 | Bindra et al. |
| 8,308,044 B2 | 11/2012 | Viola |
| 8,308,046 B2 | 11/2012 | Prommersberger |
| 8,308,757 B2 | 11/2012 | Hillstead et al. |
| 8,317,070 B2 | 11/2012 | Hueil et al. |
| 8,317,071 B1 | 11/2012 | Knodel |
| 8,322,455 B2 | 12/2012 | Shelton, IV et al. |
| 8,322,589 B2 | 12/2012 | Boudreaux |
| 8,328,061 B2 | 12/2012 | Kasvikis |
| 8,328,065 B2 | 12/2012 | Shah |
| 8,333,313 B2 | 12/2012 | Boudreaux et al. |
| 8,336,751 B2 | 12/2012 | Scirica |
| 8,336,753 B2 | 12/2012 | Olson et al. |
| 8,336,754 B2 | 12/2012 | Cappola et al. |
| 8,342,377 B2 | 1/2013 | Milliman et al. |
| 8,342,378 B2 | 1/2013 | Marczyk et al. |
| 8,342,379 B2 | 1/2013 | Whitman et al. |
| 8,342,380 B2 | 1/2013 | Viola |
| 8,348,123 B2 | 1/2013 | Scirica et al. |
| 8,348,124 B2 | 1/2013 | Scirica |
| 8,348,125 B2 | 1/2013 | Viola et al. |
| 8,348,126 B2 | 1/2013 | Olson et al. |
| 8,348,127 B2 | 1/2013 | Marczyk |
| 8,348,129 B2 | 1/2013 | Bedi et al. |
| 8,348,130 B2 | 1/2013 | Shah et al. |
| 8,348,131 B2 | 1/2013 | Omaits et al. |
| 8,348,855 B2 | 1/2013 | Hillely et al. |
| 8,353,437 B2 | 1/2013 | Boudreaux |
| 8,353,440 B2 | 1/2013 | Whitman et al. |
| 8,356,740 B1 | 1/2013 | Knodel |
| 8,357,174 B2 | 1/2013 | Roth et al. |
| 8,360,294 B2 | 1/2013 | Scirica |
| 8,360,297 B2 | 1/2013 | Shelton, IV et al. |
| 8,360,298 B2 | 1/2013 | Farascioni et al. |
| 8,360,299 B2 | 1/2013 | Zemlok et al. |
| 8,365,971 B1 | 2/2013 | Knodel |
| 8,365,972 B2 | 2/2013 | Aranyi et al. |
| 8,365,973 B1 | 2/2013 | White et al. |
| 8,365,976 B2 | 2/2013 | Hess et al. |
| 8,371,491 B2 | 2/2013 | Huitema et al. |
| 8,371,492 B2 | 2/2013 | Aranyi et al. |
| 8,371,493 B2 | 2/2013 | Aranyi et al. |
| 8,381,828 B2 | 2/2013 | Whitman et al. |
| 8,381,961 B2 | 2/2013 | Holsten et al. |
| 8,387,848 B2 | 3/2013 | Johnson et al. |
| 8,387,849 B2 | 3/2013 | Buesseler et al. |
| 8,387,850 B2 | 3/2013 | Hathaway et al. |
| 8,388,652 B2 | 3/2013 | Viola |
| 8,393,513 B2 | 3/2013 | Jankowski |
| 8,393,514 B2 | 3/2013 | Shelton, IV et al. |
| 8,393,516 B2 | 3/2013 | Kostrzewski |
| 8,397,971 B2 | 3/2013 | Yates et al. |
| 8,397,972 B2 | 3/2013 | Kostrzewski |
| 8,403,195 B2 | 3/2013 | Beardsley et al. |
| 8,403,196 B2 | 3/2013 | Beardsley et al. |
| 8,403,197 B2 | 3/2013 | Vidal et al. |
| 8,403,198 B2 | 3/2013 | Sorrentino et al. |
| 8,403,956 B1 | 3/2013 | Thompson et al. |
| 8,408,439 B2 | 4/2013 | Huang et al. |
| 8,408,440 B2 | 4/2013 | Olson et al. |
| 8,408,442 B2 | 4/2013 | Racenet et al. |
| 8,413,868 B2 | 4/2013 | Cappola |
| 8,413,869 B2 | 4/2013 | Heinrich |
| 8,413,871 B2 | 4/2013 | Racenet et al. |
| 8,418,904 B2 | 4/2013 | Wenchell et al. |
| 8,418,905 B2 | 4/2013 | Milliman |
| 8,418,906 B2 | 4/2013 | Farascioni et al. |
| 8,418,907 B2 | 4/2013 | Johnson et al. |
| 8,418,908 B1 | 4/2013 | Beardsley |
| 8,419,768 B2 | 4/2013 | Marczyk |
| 8,424,735 B2 | 4/2013 | Viola et al. |
| 8,424,736 B2 | 4/2013 | Scirica et al. |
| 8,424,737 B2 | 4/2013 | Scirica |
| 8,424,739 B2 | 4/2013 | Racenet et al. |
| 8,424,740 B2 | 4/2013 | Shelton, IV et al. |
| 8,439,244 B2 | 5/2013 | Holcomb et al. |
| 8,439,245 B2 | 5/2013 | Knodel et al. |
| 8,439,246 B1 | 5/2013 | Knodel |
| 8,444,036 B2 | 5/2013 | Shelton, IV |
| 8,444,037 B2 | 5/2013 | Nicholas et al. |
| 8,444,038 B2 | 5/2013 | Farascioni et al. |
| 8,448,832 B2 | 5/2013 | Viola et al. |
| 8,453,652 B2 | 6/2013 | Stopek |
| 8,453,905 B2 | 6/2013 | Holcomb et al. |
| 8,453,906 B2 | 6/2013 | Huang et al. |
| 8,453,907 B2 | 6/2013 | Laurent et al. |
| 8,453,908 B2 | 6/2013 | Bedi et al. |
| 8,453,909 B2 | 6/2013 | Olson et al. |
| 8,453,910 B2 | 6/2013 | Bettuchi et al. |
| 8,453,912 B2 | 6/2013 | Mastri et al. |
| 8,453,913 B2 | 6/2013 | Milliman |
| 8,453,914 B2 | 6/2013 | Laurent et al. |
| 8,454,628 B2 | 6/2013 | Smith et al. |
| 8,459,520 B2 | 6/2013 | Giordano et al. |
| 8,459,521 B2 | 6/2013 | Zemlok et al. |
| 8,459,522 B2 | 6/2013 | Marczyk |
| 8,459,523 B2 | 6/2013 | Whitman |
| 8,459,524 B2 | 6/2013 | Pribanic et al. |
| 8,459,525 B2 | 6/2013 | Yates et al. |
| 8,464,922 B2 | 6/2013 | Marczyk |
| 8,464,923 B2 | 6/2013 | Shelton, IV |
| 8,469,252 B2 | 6/2013 | Holcomb et al. |
| 8,469,254 B2 | 6/2013 | Czernik et al. |
| 8,474,677 B2 | 7/2013 | Woodard, Jr. et al. |
| 8,479,967 B2 | 7/2013 | Marczyk |
| 8,479,968 B2 | 7/2013 | Hodgkinson et al. |
| 8,479,969 B2 | 7/2013 | Shelton, IV |
| 8,485,412 B2 | 7/2013 | Shelton, IV et al. |
| 8,490,852 B2 | 7/2013 | Viola |
| 8,496,152 B2 | 7/2013 | Viola |
| 8,496,154 B2 | 7/2013 | Marczyk et al. |
| 8,496,156 B2 | 7/2013 | Sniffin et al. |
| 8,496,683 B2 | 7/2013 | Prommersberger et al. |
| 8,499,993 B2 | 8/2013 | Shelton, IV et al. |
| 8,505,799 B2 | 8/2013 | Viola et al. |

(56) References Cited

U.S. PATENT DOCUMENTS

| | | |
|---|---|---|
| 8,505,802 B2 | 8/2013 | Viola et al. |
| 8,511,575 B2 | 8/2013 | Cok |
| 8,512,359 B2 | 8/2013 | Whitman et al. |
| 8,512,402 B2 | 8/2013 | Marczyk et al. |
| 8,517,239 B2 * | 8/2013 | Scheib ............. A61B 17/07207 227/175.1 |
| 8,517,241 B2 | 8/2013 | Nicholas et al. |
| 8,517,243 B2 | 8/2013 | Giordano et al. |
| 8,517,244 B2 | 8/2013 | Shelton, IV et al. |
| 8,523,041 B2 | 9/2013 | Ishitsuki et al. |
| 8,523,042 B2 | 9/2013 | Masiakos et al. |
| 8,523,043 B2 | 9/2013 | Ullrich et al. |
| 8,534,528 B2 | 9/2013 | Shelton, IV |
| 8,540,128 B2 | 9/2013 | Shelton, IV et al. |
| 8,540,129 B2 | 9/2013 | Baxter, III et al. |
| 8,540,130 B2 | 9/2013 | Moore et al. |
| 8,540,131 B2 | 9/2013 | Swayze |
| 8,540,733 B2 | 9/2013 | Whitman et al. |
| 8,544,711 B2 | 10/2013 | Ma et al. |
| 8,550,325 B2 | 10/2013 | Cohen et al. |
| 8,556,151 B2 | 10/2013 | Viola |
| 8,561,870 B2 | 10/2013 | Baxter, III et al. |
| 8,561,873 B2 | 10/2013 | Ingmanson et al. |
| 8,561,874 B2 | 10/2013 | Scirica |
| 8,567,656 B2 | 10/2013 | Shelton, IV et al. |
| 8,573,461 B2 | 11/2013 | Shelton, IV et al. |
| 8,573,463 B2 | 11/2013 | Scirica et al. |
| 8,573,465 B2 | 11/2013 | Shelton, IV |
| 8,579,176 B2 | 11/2013 | Smith et al. |
| 8,579,177 B2 | 11/2013 | Beetel |
| 8,584,919 B2 | 11/2013 | Hueil et al. |
| 8,584,920 B2 | 11/2013 | Hodgkinson |
| 8,590,762 B2 | 11/2013 | Hess et al. |
| 8,596,515 B2 | 12/2013 | Okoniewski |
| 8,602,288 B2 | 12/2013 | Shelton, IV et al. |
| 8,608,045 B2 | 12/2013 | Smith et al. |
| 8,608,046 B2 | 12/2013 | Laurent et al. |
| 8,608,047 B2 | 12/2013 | Holsten et al. |
| 8,613,383 B2 | 12/2013 | Beckman et al. |
| 8,613,384 B2 | 12/2013 | Pastorelli et al. |
| 8,616,427 B2 | 12/2013 | Viola |
| 8,616,430 B2 | 12/2013 | (Prommersberger) Stopek et al. |
| 8,627,994 B2 | 1/2014 | Zemlok et al. |
| 8,628,544 B2 | 1/2014 | Farascioni |
| 8,631,988 B2 | 1/2014 | Viola |
| 8,631,989 B2 | 1/2014 | Aranyi et al. |
| 8,631,991 B2 | 1/2014 | Cropper et al. |
| 8,632,525 B2 | 1/2014 | Kerr et al. |
| 8,632,535 B2 | 1/2014 | Shelton, IV et al. |
| 8,636,187 B2 | 1/2014 | Hueil et al. |
| 8,636,190 B2 | 1/2014 | Zemlok et al. |
| 8,636,192 B2 | 1/2014 | Farascioni et al. |
| 8,636,762 B2 | 1/2014 | Whitman et al. |
| 8,636,766 B2 | 1/2014 | Milliman et al. |
| 8,640,940 B2 | 2/2014 | Ohdaira |
| 8,657,174 B2 | 2/2014 | Yates et al. |
| 8,657,177 B2 | 2/2014 | Scirica et al. |
| 8,657,178 B2 | 2/2014 | Hueil et al. |
| 8,662,371 B2 | 3/2014 | Viola |
| 8,668,129 B2 | 3/2014 | Olson |
| 8,672,206 B2 | 3/2014 | Aranyi et al. |
| 8,672,208 B2 | 3/2014 | Hess et al. |
| 8,672,209 B2 | 3/2014 | Crainich |
| 8,678,263 B2 | 3/2014 | Viola |
| 8,678,990 B2 | 3/2014 | Wazer et al. |
| 8,679,155 B2 | 3/2014 | Knodel et al. |
| 8,684,247 B2 | 4/2014 | Scirica et al. |
| 8,684,249 B2 | 4/2014 | Racenet et al. |
| 8,690,039 B2 | 4/2014 | Beardsley et al. |
| 8,695,865 B2 | 4/2014 | Smith et al. |
| 8,695,866 B2 | 4/2014 | Leimbach et al. |
| 8,701,958 B2 | 4/2014 | Shelton, IV et al. |
| 8,701,959 B2 | 4/2014 | Shah |
| 8,701,961 B2 | 4/2014 | Ivanko |
| 8,708,213 B2 | 4/2014 | Shelton, IV et al. |
| 8,714,429 B2 | 5/2014 | Demmy |
| 8,715,277 B2 | 5/2014 | Weizman |
| 8,720,766 B2 | 5/2014 | Hess et al. |
| 8,721,630 B2 | 5/2014 | Ortiz et al. |
| 8,727,197 B2 | 5/2014 | Hess et al. |
| 8,727,200 B2 | 5/2014 | Roy |
| 8,733,612 B2 | 5/2014 | Ma |
| 8,740,034 B2 | 6/2014 | Morgan et al. |
| 8,740,039 B2 | 6/2014 | Farascioni |
| 8,746,533 B2 | 6/2014 | Whitman |
| 8,757,465 B2 | 6/2014 | Woodard, Jr. et al. |
| 8,758,391 B2 | 6/2014 | Swayze et al. |
| 8,763,877 B2 | 7/2014 | Schall et al. |
| 8,763,879 B2 | 7/2014 | Shelton, IV et al. |
| 8,770,458 B2 | 7/2014 | Scirica |
| 8,777,082 B2 | 7/2014 | Scirica |
| 8,783,541 B2 | 7/2014 | Shelton, IV et al. |
| 8,783,542 B2 | 7/2014 | Riestenberg et al. |
| 8,789,737 B2 | 7/2014 | Hodgkinson et al. |
| 8,789,738 B2 | 7/2014 | Knodel et al. |
| 8,789,739 B2 | 7/2014 | Swensgard |
| 8,800,838 B2 | 8/2014 | Shelton, IV |
| 8,800,840 B2 | 8/2014 | Jankowski |
| 8,800,841 B2 | 8/2014 | Ellerhorst et al. |
| 8,806,973 B2 | 8/2014 | Ross et al. |
| 8,808,311 B2 | 8/2014 | Heinrich et al. |
| 8,814,024 B2 | 8/2014 | Woodard, Jr. et al. |
| 8,814,025 B2 | 8/2014 | Miller et al. |
| 8,820,603 B2 | 9/2014 | Shelton, IV et al. |
| 8,820,605 B2 | 9/2014 | Shelton, IV |
| 8,820,607 B2 | 9/2014 | Marczyk |
| 8,827,133 B2 | 9/2014 | Shelton, IV et al. |
| 8,827,134 B2 | 9/2014 | Viola et al. |
| 8,833,632 B2 | 9/2014 | Swensgard |
| 8,840,003 B2 | 9/2014 | Morgan et al. |
| 8,840,603 B2 | 9/2014 | Shelton, IV et al. |
| 8,875,972 B2 | 11/2014 | Weisenburgh, II et al. |
| 8,893,946 B2 | 11/2014 | Boudreaux et al. |
| 8,899,462 B2 | 12/2014 | Kostrzewski et al. |
| 8,939,344 B2 | 1/2015 | Olson et al. |
| 8,960,519 B2 | 2/2015 | Whitman et al. |
| 8,961,396 B2 | 2/2015 | Azarbarzin et al. |
| 8,968,276 B2 | 3/2015 | Zemlok et al. |
| 8,968,337 B2 | 3/2015 | Whitfield et al. |
| 8,992,422 B2 | 3/2015 | Spivey et al. |
| 9,023,014 B2 | 5/2015 | Chowaniec et al. |
| 9,055,943 B2 | 6/2015 | Zemlok et al. |
| 9,064,653 B2 | 6/2015 | Prest et al. |
| 9,113,875 B2 | 8/2015 | Viola et al. |
| 9,216,013 B2 | 12/2015 | Scirica et al. |
| 9,282,961 B2 | 3/2016 | Whitman et al. |
| 9,282,963 B2 | 3/2016 | Bryant |
| 9,295,522 B2 | 3/2016 | Kostrzewski |
| 9,307,986 B2 | 4/2016 | Hall et al. |
| 9,700,318 B2 | 7/2017 | Scirica et al. |
| 9,775,610 B2 | 10/2017 | Nicholas et al. |
| 10,117,650 B2 | 11/2018 | Nicholas et al. |
| 2002/0049454 A1 | 4/2002 | Whitman et al. |
| 2002/0165541 A1 | 11/2002 | Whitman |
| 2003/0165794 A1 | 9/2003 | Matoba |
| 2004/0108357 A1 | 6/2004 | Milliman et al. |
| 2004/0199180 A1 | 10/2004 | Knodel et al. |
| 2004/0199181 A1 | 10/2004 | Knodel et al. |
| 2004/0243151 A1 | 12/2004 | Demmy et al. |
| 2004/0267310 A1 | 12/2004 | Racenet et al. |
| 2005/0103819 A1 | 5/2005 | Racenet et al. |
| 2005/0216055 A1 | 9/2005 | Scirica et al. |
| 2006/0049229 A1 | 3/2006 | Milliman et al. |
| 2006/0142740 A1 | 6/2006 | Sherman et al. |
| 2006/0180634 A1 | 8/2006 | Shelton et al. |
| 2006/0289602 A1 | 12/2006 | Wales et al. |
| 2007/0023476 A1 | 2/2007 | Whitman et al. |
| 2007/0073341 A1 | 3/2007 | Smith et al. |
| 2007/0084897 A1 | 4/2007 | Shelton et al. |
| 2007/0102472 A1 | 5/2007 | Shelton |
| 2007/0106317 A1 | 5/2007 | Shelton et al. |
| 2007/0119901 A1 | 5/2007 | Ehrenfels et al. |
| 2007/0145096 A1 | 6/2007 | Viola et al. |
| 2007/0170225 A1 | 7/2007 | Shelton et al. |

(56) References Cited

U.S. PATENT DOCUMENTS

| | | |
|---|---|---|
| 2007/0175949 A1 | 8/2007 | Shelton et al. |
| 2007/0175950 A1 | 8/2007 | Shelton et al. |
| 2007/0175951 A1 | 8/2007 | Shelton et al. |
| 2007/0175955 A1 | 8/2007 | Shelton et al. |
| 2007/0179528 A1 | 8/2007 | Soltz et al. |
| 2007/0194079 A1 | 8/2007 | Hueil |
| 2007/0194082 A1 | 8/2007 | Morgan et al. |
| 2008/0029570 A1 | 2/2008 | Shelton et al. |
| 2008/0029573 A1 | 2/2008 | Shelton et al. |
| 2008/0029574 A1 | 2/2008 | Shelton et al. |
| 2008/0029575 A1 | 2/2008 | Shelton et al. |
| 2008/0078802 A1 | 4/2008 | Hess et al. |
| 2008/0110961 A1 | 5/2008 | Voegele et al. |
| 2008/0167736 A1 | 7/2008 | Swayze et al. |
| 2008/0169328 A1 | 7/2008 | Shelton |
| 2008/0169332 A1 | 7/2008 | Shelton et al. |
| 2008/0169333 A1 | 7/2008 | Shelton et al. |
| 2008/0237296 A1 | 10/2008 | Boudreaux et al. |
| 2008/0257935 A1 | 10/2008 | Viola |
| 2008/0287987 A1 | 11/2008 | Boyden et al. |
| 2008/0296346 A1 | 12/2008 | Shelton, IV et al. |
| 2008/0308602 A1 | 12/2008 | Timm et al. |
| 2008/0308603 A1 | 12/2008 | Shelton et al. |
| 2009/0001121 A1 | 1/2009 | Hess et al. |
| 2009/0001130 A1 | 1/2009 | Hess et al. |
| 2009/0090763 A1 | 4/2009 | Zemlok et al. |
| 2009/0090764 A1 | 4/2009 | Viola |
| 2009/0090766 A1 | 4/2009 | Knodel |
| 2009/0101692 A1 | 4/2009 | Whitman et al. |
| 2009/0242610 A1 | 10/2009 | Shelton, IV et al. |
| 2009/0255974 A1 | 10/2009 | Viola |
| 2009/0272787 A1 | 11/2009 | Scirica |
| 2009/0277949 A1 | 11/2009 | Viola et al. |
| 2009/0283568 A1 | 11/2009 | Racenet et al. |
| 2009/0308907 A1 | 12/2009 | Nalagatla et al. |
| 2010/0012703 A1 | 1/2010 | Calabrese et al. |
| 2010/0069942 A1 | 3/2010 | Shelton, IV |
| 2010/0127041 A1 | 5/2010 | Morgan et al. |
| 2010/0133317 A1 | 6/2010 | Shelton, IV et al. |
| 2010/0147921 A1 | 6/2010 | Olson |
| 2010/0147922 A1 | 6/2010 | Olson |
| 2010/0155453 A1 | 6/2010 | Bombard et al. |
| 2010/0193566 A1 | 8/2010 | Scheib et al. |
| 2010/0193568 A1 | 8/2010 | Scheib et al. |
| 2010/0211053 A1 | 8/2010 | Ross et al. |
| 2010/0224668 A1 | 9/2010 | Fontayne et al. |
| 2010/0249802 A1 | 9/2010 | May et al. |
| 2010/0252611 A1 | 10/2010 | Ezzat et al. |
| 2010/0305552 A1 | 12/2010 | Shelton, IV et al. |
| 2010/0320252 A1 | 12/2010 | Viola et al. |
| 2011/0006099 A1 | 1/2011 | Hall et al. |
| 2011/0006101 A1 | 1/2011 | Hall et al. |
| 2011/0017801 A1 | 1/2011 | Zemlok et al. |
| 2011/0024477 A1 | 2/2011 | Hall |
| 2011/0024478 A1 | 2/2011 | Shelton, IV |
| 2011/0036891 A1 | 2/2011 | Zemlok et al. |
| 2011/0068148 A1 | 3/2011 | Hall et al. |
| 2011/0071508 A1 | 3/2011 | Duval et al. |
| 2011/0087276 A1 | 4/2011 | Bedi et al. |
| 2011/0101069 A1 | 5/2011 | Bombard et al. |
| 2011/0108603 A1 | 5/2011 | Racenet et al. |
| 2011/0114702 A1 | 5/2011 | Farascioni |
| 2011/0121049 A1 | 5/2011 | Malinouskas et al. |
| 2011/0132961 A1 | 6/2011 | Whitman et al. |
| 2011/0132964 A1 | 6/2011 | Weisenburgh, II et al. |
| 2011/0139851 A1 | 6/2011 | McCuen |
| 2011/0147433 A1 | 6/2011 | Shelton, IV et al. |
| 2011/0155781 A1 | 6/2011 | Swensgard et al. |
| 2011/0155786 A1 | 6/2011 | Shelton, IV |
| 2011/0155787 A1 | 6/2011 | Baxter, III et al. |
| 2011/0163146 A1 | 7/2011 | Ortiz et al. |
| 2011/0163149 A1 | 7/2011 | Viola |
| 2011/0172648 A1 | 7/2011 | Jeong |
| 2011/0174099 A1 | 7/2011 | Ross et al. |
| 2011/0192881 A1 | 8/2011 | Balbierz et al. |
| 2011/0192882 A1 | 8/2011 | Hess et al. |
| 2011/0192883 A1 | 8/2011 | Whitman et al. |
| 2011/0204119 A1 | 8/2011 | McCuen |
| 2011/0276057 A1 | 11/2011 | Conlon et al. |
| 2011/0278343 A1 | 11/2011 | Knodel et al. |
| 2011/0288573 A1 | 11/2011 | Yates et al. |
| 2011/0290851 A1 | 12/2011 | Shelton, IV |
| 2011/0290853 A1 | 12/2011 | Shelton, IV et al. |
| 2011/0290854 A1 | 12/2011 | Timm et al. |
| 2011/0290855 A1 | 12/2011 | Moore et al. |
| 2011/0290856 A1 | 12/2011 | Shelton, IV et al. |
| 2012/0016362 A1 | 1/2012 | Heinrich et al. |
| 2012/0037683 A1 | 2/2012 | Lee |
| 2012/0053406 A1 | 3/2012 | Conlon et al. |
| 2012/0061446 A1 | 3/2012 | Knodel et al. |
| 2012/0061450 A1 | 3/2012 | Kostrzewski |
| 2012/0074196 A1 | 3/2012 | Shelton, IV et al. |
| 2012/0074199 A1 | 3/2012 | Olson et al. |
| 2012/0074200 A1 | 3/2012 | Schmid et al. |
| 2012/0080474 A1 | 4/2012 | Farascioni |
| 2012/0080475 A1 | 4/2012 | Smith et al. |
| 2012/0080478 A1 | 4/2012 | Morgan et al. |
| 2012/0080479 A1 | 4/2012 | Shelton, IV |
| 2012/0080481 A1 | 4/2012 | Widenhouse et al. |
| 2012/0080482 A1 | 4/2012 | Schall et al. |
| 2012/0080484 A1 | 4/2012 | Morgan et al. |
| 2012/0080485 A1 | 4/2012 | Woodard, Jr. et al. |
| 2012/0080486 A1 | 4/2012 | Woodard, Jr. et al. |
| 2012/0080488 A1 | 4/2012 | Shelton, IV et al. |
| 2012/0080489 A1 | 4/2012 | Shelton, IV et al. |
| 2012/0080490 A1 | 4/2012 | Shelton, IV et al. |
| 2012/0080491 A1 | 4/2012 | Shelton, IV et al. |
| 2012/0080493 A1 | 4/2012 | Shelton, IV et al. |
| 2012/0080494 A1 | 4/2012 | Thompson et al. |
| 2012/0080495 A1 | 4/2012 | Holcomb et al. |
| 2012/0080498 A1 | 4/2012 | Shelton, IV et al. |
| 2012/0080499 A1 | 4/2012 | Schall et al. |
| 2012/0080502 A1 | 4/2012 | Morgan et al. |
| 2012/0089131 A1 | 4/2012 | Zemlok et al. |
| 2012/0091183 A1 | 4/2012 | Manoux et al. |
| 2012/0100200 A1 | 4/2012 | Belcheva et al. |
| 2012/0104071 A1 | 5/2012 | Bryant |
| 2012/0116368 A1 | 5/2012 | Viola |
| 2012/0138659 A1 | 6/2012 | Marczyk et al. |
| 2012/0175399 A1 | 7/2012 | Shelton et al. |
| 2012/0181322 A1 | 7/2012 | Whitman et al. |
| 2012/0187179 A1 | 7/2012 | Gleiman |
| 2012/0193394 A1 | 8/2012 | Holcomb et al. |
| 2012/0193399 A1 | 8/2012 | Holcomb et al. |
| 2012/0199632 A1 | 8/2012 | Spivey et al. |
| 2012/0211542 A1 | 8/2012 | Racenet |
| 2012/0223121 A1 | 9/2012 | Viola et al. |
| 2012/0223123 A1 | 9/2012 | Baxter et al. |
| 2012/0228358 A1 | 9/2012 | Zemlok et al. |
| 2012/0234893 A1 | 9/2012 | Schuckmann et al. |
| 2012/0234895 A1 | 9/2012 | O'Connor et al. |
| 2012/0234897 A1 | 9/2012 | Shelton, IV et al. |
| 2012/0234899 A1 | 9/2012 | Scheib et al. |
| 2012/0239009 A1 | 9/2012 | Mollere et al. |
| 2012/0241491 A1 | 9/2012 | Aldridge et al. |
| 2012/0241492 A1 | 9/2012 | Shelton, IV et al. |
| 2012/0241493 A1 | 9/2012 | Baxter, III et al. |
| 2012/0241496 A1 | 9/2012 | Mandakolathur Vasudevan et al. |
| 2012/0241497 A1 | 9/2012 | Mandakolathur Vasudevan et al. |
| 2012/0241498 A1 | 9/2012 | Gonzalez et al. |
| 2012/0241499 A1 | 9/2012 | Baxter, III et al. |
| 2012/0241500 A1 | 9/2012 | Timmer et al. |
| 2012/0241501 A1 | 9/2012 | Swayze et al. |
| 2012/0241502 A1 | 9/2012 | Aldridge et al. |
| 2012/0241503 A1 | 9/2012 | Baxter, III et al. |
| 2012/0241504 A1 | 9/2012 | Soltz et al. |
| 2012/0241505 A1 | 9/2012 | Alexander, III et al. |
| 2012/0245428 A1 | 9/2012 | Smith et al. |
| 2012/0248169 A1 | 10/2012 | Widenhouse et al. |
| 2012/0248170 A1 | 10/2012 | Marczyk |
| 2012/0255986 A1 | 10/2012 | Petty |
| 2012/0286021 A1 | 11/2012 | Kostrzewski |
| 2012/0286022 A1 | 11/2012 | Olson et al. |
| 2012/0292369 A1 | 11/2012 | Munro, III et al. |

(56) References Cited

U.S. PATENT DOCUMENTS

| | | |
|---|---|---|
| 2012/0298719 A1 | 11/2012 | Shelton, IV et al. |
| 2012/0298722 A1 | 11/2012 | Hess et al. |
| 2012/0312858 A1 | 12/2012 | Patankar et al. |
| 2012/0312859 A1 | 12/2012 | Gupta et al. |
| 2012/0312860 A1 | 12/2012 | Ming et al. |
| 2012/0312861 A1 | 12/2012 | Gurumurthy et al. |
| 2012/0318842 A1 | 12/2012 | Anim et al. |
| 2012/0318843 A1 | 12/2012 | Henderson et al. |
| 2012/0318844 A1 | 12/2012 | Shelton, IV et al. |
| 2012/0330285 A1 | 12/2012 | Hartoumbekis et al. |
| 2013/0008937 A1 | 1/2013 | Viola |
| 2013/0012983 A1 | 1/2013 | Kleyman |
| 2013/0015231 A1 | 1/2013 | Kostrzewski |
| 2013/0020375 A1 | 1/2013 | Shelton, IV et al. |
| 2013/0020376 A1 | 1/2013 | Shelton, IV et al. |
| 2013/0026208 A1 | 1/2013 | Shelton, IV et al. |
| 2013/0026210 A1 | 1/2013 | Shelton, IV et al. |
| 2013/0032626 A1 | 2/2013 | Smith et al. |
| 2013/0037594 A1 | 2/2013 | Dhakad et al. |
| 2013/0037595 A1 | 2/2013 | Gupta et al. |
| 2013/0037596 A1 | 2/2013 | Bear et al. |
| 2013/0037597 A1 | 2/2013 | Katre et al. |
| 2013/0037598 A1 | 2/2013 | Marczyk |
| 2013/0041406 A1 | 2/2013 | Bear et al. |
| 2013/0048697 A1 | 2/2013 | Shelton, IV et al. |
| 2013/0056518 A1 | 3/2013 | Swensgard |
| 2013/0056521 A1 | 3/2013 | Swensgard |
| 2013/0062391 A1 | 3/2013 | Boudreaux et al. |
| 2013/0062393 A1 | 3/2013 | Bruewer et al. |
| 2013/0062394 A1 | 3/2013 | Smith et al. |
| 2013/0068815 A1 | 3/2013 | Bruewer et al. |
| 2013/0068816 A1 | 3/2013 | Mandakolathur Vasudevan et al. |
| 2013/0068818 A1 | 3/2013 | Kasvikis |
| 2013/0068821 A1 | 3/2013 | Huitema et al. |
| 2013/0075443 A1 | 3/2013 | Giordano et al. |
| 2013/0075444 A1 | 3/2013 | Cappola et al. |
| 2013/0075445 A1 | 3/2013 | Balek et al. |
| 2013/0075446 A1 | 3/2013 | Wang et al. |
| 2013/0075447 A1 | 3/2013 | Weisenburgh, II et al. |
| 2013/0075448 A1 | 3/2013 | Schmid et al. |
| 2013/0075449 A1 | 3/2013 | Schmid et al. |
| 2013/0075450 A1 | 3/2013 | Schmid et al. |
| 2013/0075451 A1 | 3/2013 | Balek et al. |
| 2013/0082086 A1 | 4/2013 | Hueil et al. |
| 2013/0087597 A1 | 4/2013 | Shelton, IV et al. |
| 2013/0087599 A1 | 4/2013 | Krumanaker et al. |
| 2013/0087600 A1 | 4/2013 | Scirica |
| 2013/0087601 A1 | 4/2013 | Farascioni |
| 2013/0087602 A1 | 4/2013 | Olson et al. |
| 2013/0087603 A1 | 4/2013 | Viola |
| 2013/0092717 A1 | 4/2013 | Marczyk et al. |
| 2013/0093149 A1 | 4/2013 | Saur et al. |
| 2013/0098964 A1 | 4/2013 | Smith et al. |
| 2013/0098965 A1 | 4/2013 | Kostrzewski et al. |
| 2013/0098966 A1 | 4/2013 | Kostrzewski et al. |
| 2013/0098968 A1 | 4/2013 | Aranyi et al. |
| 2013/0098970 A1 | 4/2013 | Racenet et al. |
| 2013/0105545 A1 | 5/2013 | Burbank |
| 2013/0105548 A1 | 5/2013 | Hodgkinson et al. |
| 2013/0105552 A1 | 5/2013 | Weir et al. |
| 2013/0105553 A1 | 5/2013 | (Tarinelli) Racenet et al. |
| 2013/0112730 A1 | 5/2013 | Whitman et al. |
| 2013/0112732 A1 | 5/2013 | Aranyi et al. |
| 2013/0112733 A1 | 5/2013 | Aranyi et al. |
| 2013/0119109 A1 | 5/2013 | Farascioni et al. |
| 2013/0126581 A1 | 5/2013 | Yates et al. |
| 2013/0126582 A1 | 5/2013 | Shelton, IV et al. |
| 2013/0126586 A1 | 5/2013 | Zhang et al. |
| 2013/0140343 A1 | 6/2013 | Knodel |
| 2013/0144333 A1 | 6/2013 | Viola |
| 2013/0181035 A1 | 7/2013 | Milliman |
| 2013/0184704 A1 | 7/2013 | Beardsley et al. |
| 2013/0274722 A1 | 10/2013 | Kostrzewski et al. |
| 2013/0282052 A1 | 10/2013 | Aranyi et al. |
| 2013/0324978 A1 | 12/2013 | Nicholas et al. |
| 2013/0324979 A1 | 12/2013 | Nicholas et al. |
| 2013/0334281 A1 | 12/2013 | Williams |
| 2014/0001235 A1 | 1/2014 | Shelton, IV |
| 2014/0005678 A1 | 1/2014 | Shelton, IV et al. |
| 2014/0207125 A1 | 7/2014 | Applegate et al. |
| 2014/0303668 A1 | 10/2014 | Nicholas et al. |
| 2014/0367447 A1 | 12/2014 | Woodard, Jr. et al. |
| 2014/0373652 A1 | 12/2014 | Zergiebel et al. |
| 2015/0157321 A1 | 6/2015 | Zergiebel et al. |
| 2015/0164502 A1 | 6/2015 | Richard et al. |
| 2015/0209040 A1 | 7/2015 | Whitman et al. |
| 2015/0272577 A1 | 10/2015 | Zemlok et al. |
| 2015/0297199 A1 | 10/2015 | Nicholas et al. |
| 2015/0303996 A1 | 10/2015 | Calderoni |
| 2015/0320420 A1 | 11/2015 | Penna et al. |
| 2015/0327850 A1 | 11/2015 | Kostrzewski |
| 2015/0342601 A1 | 12/2015 | Williams et al. |
| 2015/0342603 A1 | 12/2015 | Zergiebel et al. |
| 2015/0374366 A1 | 12/2015 | Zergiebel et al. |
| 2015/0374370 A1 | 12/2015 | Zergiebel et al. |
| 2015/0374371 A1 | 12/2015 | Richard et al. |
| 2015/0374372 A1 | 12/2015 | Zergiebel et al. |
| 2015/0374449 A1 | 12/2015 | Chowaniec et al. |
| 2015/0380187 A1 | 12/2015 | Zergiebel et al. |
| 2016/0095585 A1 | 4/2016 | Zergiebel et al. |
| 2016/0095596 A1 | 4/2016 | Scirica et al. |
| 2016/0106406 A1 | 4/2016 | Cabrera et al. |
| 2016/0113648 A1 | 4/2016 | Zergiebel et al. |
| 2016/0113649 A1 | 4/2016 | Zergiebel et al. |

FOREIGN PATENT DOCUMENTS

| | | |
|---|---|---|
| CN | 104736070 A | 6/2015 |
| EP | 2505146 A1 | 10/2012 |
| EP | 2668910 A2 | 12/2013 |
| EP | 2687164 A2 | 1/2014 |
| JP | 2000512185 A | 9/2000 |
| JP | 2004041733 A | 2/2004 |
| JP | 2014018667 A | 2/2014 |
| JP | 2014155826 A | 8/2014 |
| KR | 20120022521 A | 3/2012 |
| WO | 9814124 | 4/1998 |
| WO | 2006048905 A1 | 5/2006 |

OTHER PUBLICATIONS

Japanese Office Action corresponding to International Application No. JP 2011-084092 dated Jan. 14, 2016.

Extended European Search Report corresponding to International Application No. EP 12 19 7970.2 dated Jan. 28, 2016.

Chinese Office Action corresponding to International Application No. CN 201210560638.1 dated Oct. 21, 2015.

European Office Action corresponding to International Application No. EP 14 15 9056.2 dated Oct. 26, 2015.

Australian Examination Report No. 1 corresponding to International Application No. AU 2015200153 dated Dec. 11, 2015.

Australian Examination Report No. 1 corresponding to International Application No. AU 2014204542 dated Jan. 7, 2016.

Chinese Office Action corresponding to International Application No. CN 201310125449.6 dated Feb. 3, 2016.

Extended European Search Report corresponding to International Application No. EP 15 19 0245.9 dated Jan. 28, 2016.

Extended European Search Report corresponding to International Application No. EP 15 16 7793.7 dated Apr. 5, 2016.

European Office Action corresponding to International Application No. EP 14 18 4882.0 dated Apr. 25, 2016.

Extended European Search Report corresponding to International Application No. EP 14 19 6704.2 dated Sep. 24, 2015.

International Search Report and Written Opinion corresponding to Int'l Appln. No. PCT/US2015/051837, dated Dec. 21, 2015.

Extended European Search Report corresponding to International Application No. EP 14 19 7563.1 dated Aug. 5, 2015.

Partial European Search Report corresponding to International Application No. EP 15 19 0643.5 dated Feb. 26, 2016.

Extended European Search Report corresponding to International Application No. EP 15 16 6899.3 dated Feb. 3, 2016.

(56) References Cited

OTHER PUBLICATIONS

Extended European Search Report corresponding to International Application No. EP 14 19 9783.3 dated Dec. 22, 2015.
Extended European Search Report corresponding to International Application No. EP 15 17 3807.7 dated Nov. 24, 2015.
Extended European Search Report corresponding to International Application No. EP 15 19 0760.7 dated Apr. 1, 2016.
Extended European Search Report corresponding to International Application No. EP 15 17 3803.6 dated Nov. 24, 2015.
Extended European Search Report corresponding to International Application No. EP 15 17 3804.4 dated Nov. 24, 2015.
Extended European Search Report corresponding to International Application No. EP 15 18 8539.9 dated Feb. 17, 2016.
Extended European Search Report corresponding to International Application No. EP 15 17 3910.9 dated Nov. 13, 2015.
European Office Action corresponding to International Application No. EP 14 15 2236.7 dated Aug. 11, 2015.
Extended European Search Report corresponding to International Application No. EP 15 18 4915.5 dated Jan. 5, 2016.
Extended European Search Report for EP 16 16 8312 dated Sep. 29, 2016.
European Search Report dated Dec. 1, 2017, issued in EP Appln. No. 17169869.
Australian Examination Report dated Nov. 11, 2019, issued in AU Appln. No. 2016202266.
Chinese Office Action (with English translation), dated Sep. 21, 2020, corresponding to counterpart Chinese Application No. 201710305087.7; 17 total pages.
Chinese Office Action dated Nov. 4, 2019, issued in Chinese Appln. No. 201610293620.
Chinese Office Action dated May 15, 2020, issued in CN Appln. No. 201610293620, 7 pages.
Japanese Office Action dated Dec. 16, 2019, issued in JP Appln. No. 2016090674.
Chinese Office Action (with English translation), dated Sep. 23, 2020, corresponding to counterpart Chinese Application No. 201610293620.8; 14 total pages.
Japanese Office Action issued in Japanese Patent Application No. 2017-092214, dated Apr. 1, 2021.

* cited by examiner

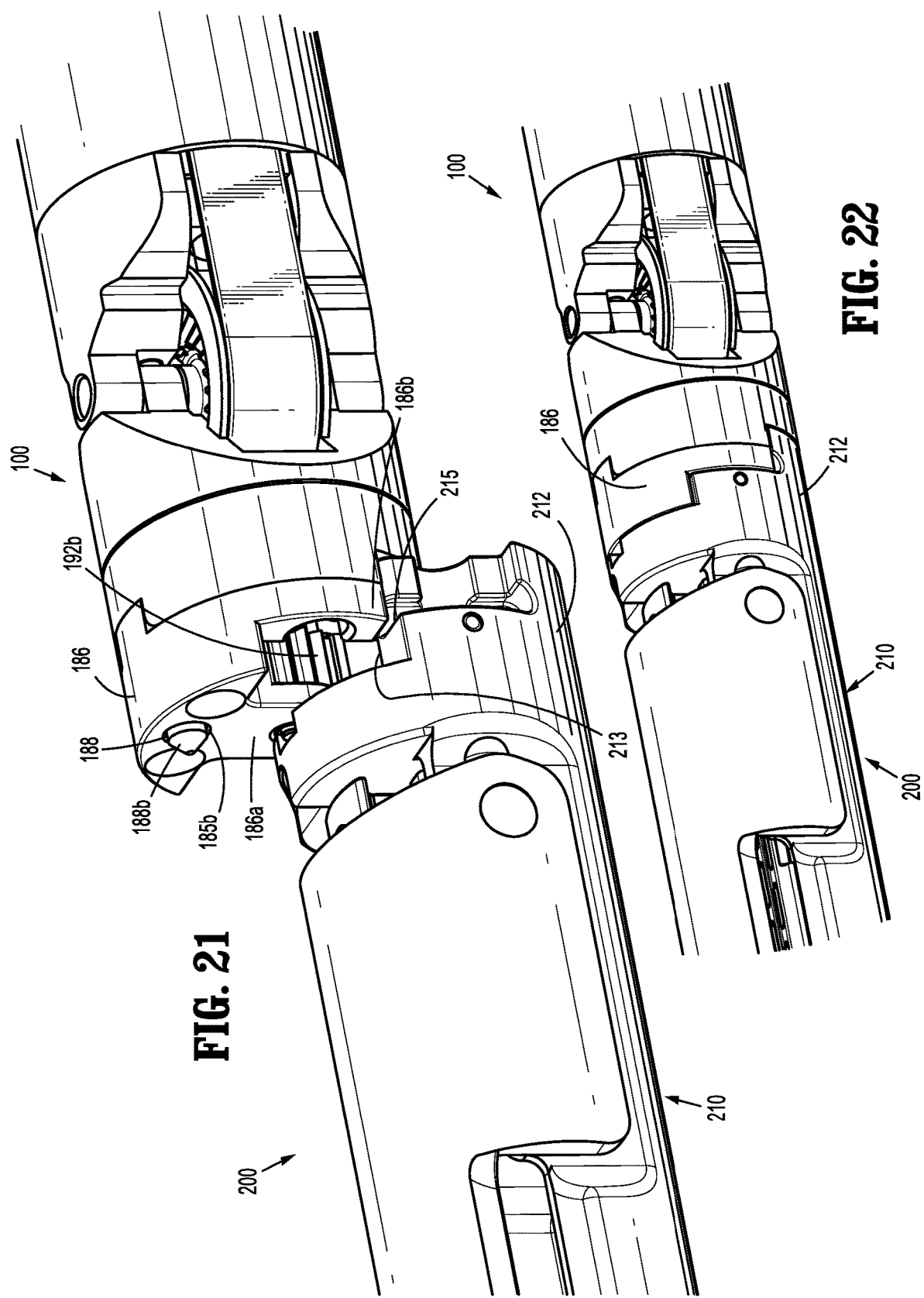

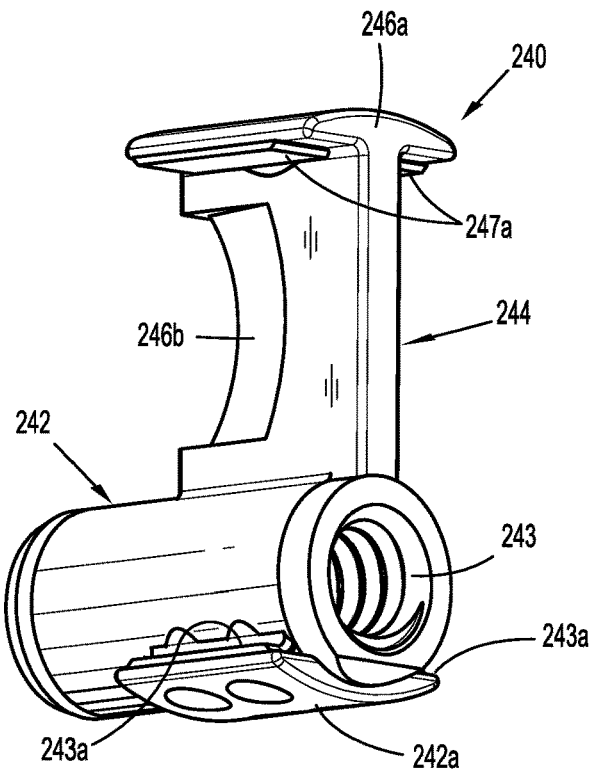
FIG. 24
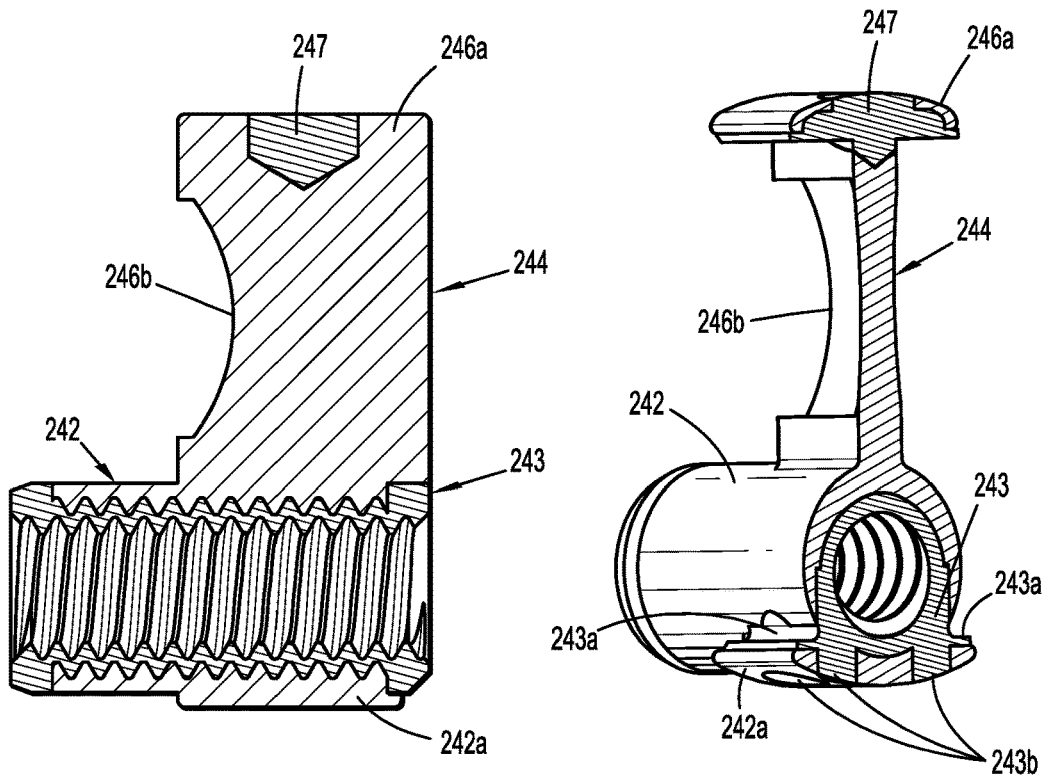
FIG. 25  FIG. 26

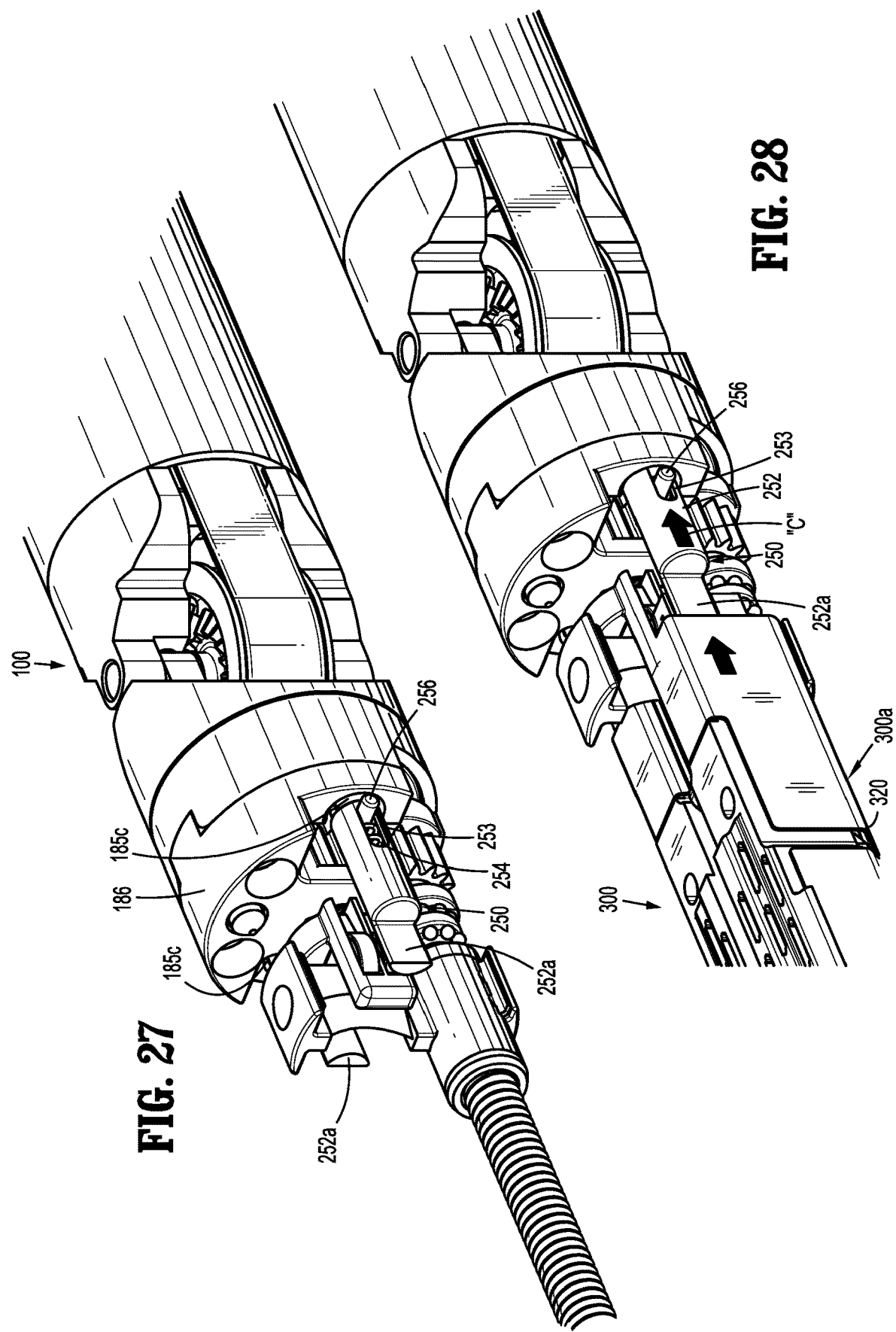

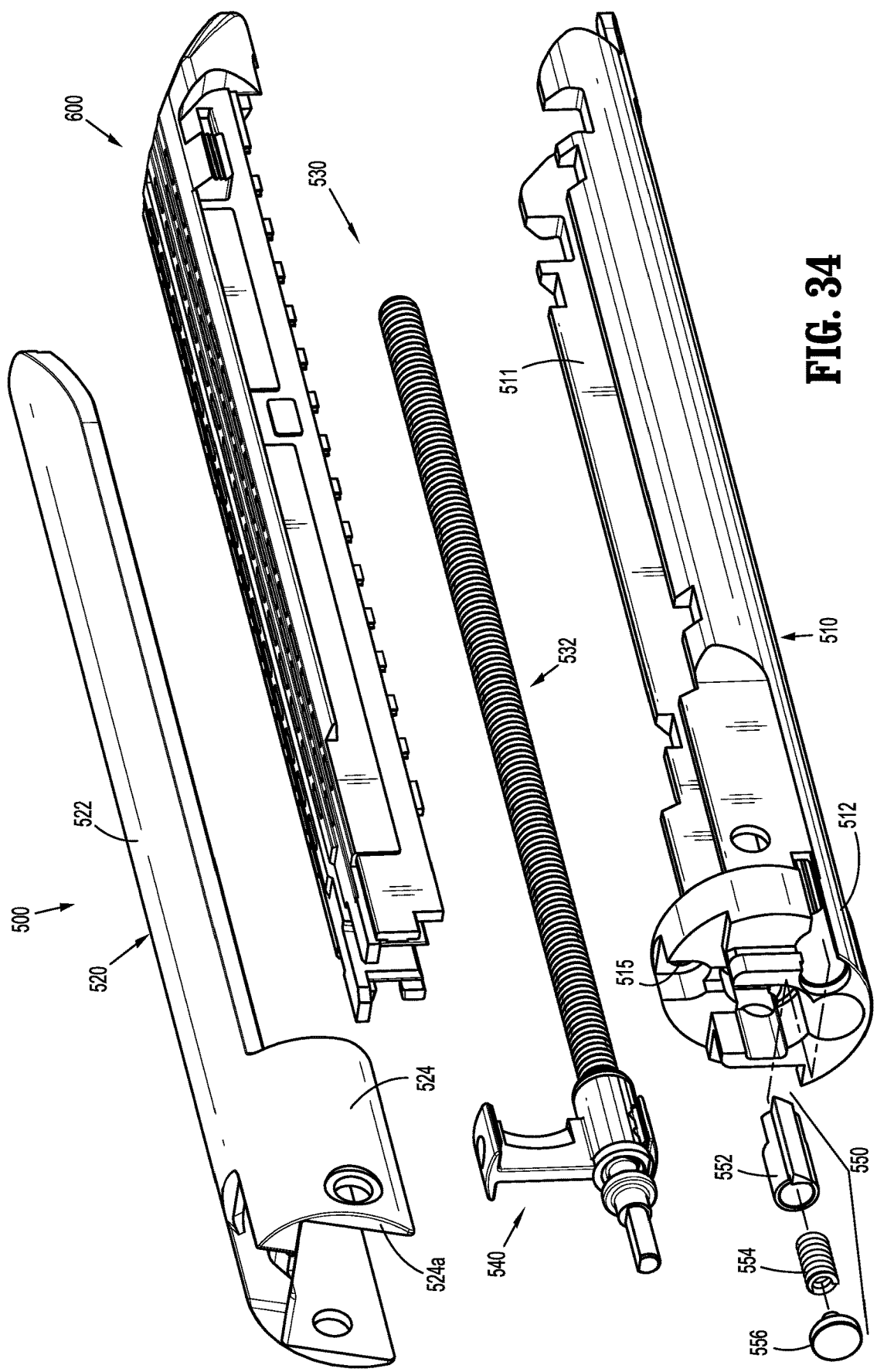

ADAPTER ASSEMBLY AND LOADING UNITS FOR SURGICAL STAPLING DEVICES

CROSS-REFERENCE TO RELATED APPLICATIONS

The present application is a Continuation application which claims that benefit of and priority to U.S. patent application Ser. No. 14/703,956, filed on May 5, 2015, now U.S. Pat. No. 10,117,650, the entire content of which is incorporated herein by reference.

BACKGROUND

1. Technical Field

The present disclosure relates to surgical stapling devices. More specifically, the present disclosure relates to adapter assemblies for use with the powered surgical stapling devices and loading units for use with the adapter assemblies.

2. Background of Related Art

Surgical stapling devices having a powered handle are known. Such devices typically include an adapter assembly for connecting loading units to the powered handle. Often the adapter assemblies transfer rotational motion from one or more motors in the powered handle assembly into linear motion to actuate and articulate the attached loading units. Because replacing a used disposable loading unit or replacing a used cartridge assembly of a multiple use loading unit during a surgical procedure may be a complicated and/or time consuming process, it would be desirable to have an adapter assembly and loading unit with an easily attachable and replaceable loading unit.

SUMMARY

Accordingly, a surgical apparatus is provided. The surgical apparatus includes a proximal body portion a distal body portion selectively articulable relative to the proximal body portion at an articulation joint and including a distal end configured for selective engagement with a loading unit, and a first drive gear disposed within the distal body portion. The distal body portion defines a longitudinal axis and having a diameter and a length. The length of the distal body portion is substantially the same as the diameter of the distal body portion. The drive gear may be rotatable about the longitudinal axis. The surgical apparatus may further include a handle assembly. A proximal end of the proximal body portion may be connected to the handle assembly.

In embodiments, the surgical apparatus further includes a loading unit selectively engageable with the distal end of the distal body portion. The loading unit may include a second drive gear configured to engage the first drive gear when the loading unit is secured to the distal end of the distal body portion. The loading unit may include a drive screw and the second drive gear may be disposed on a proximal end of the drive screw. The loading unit may include a drive beam operably disposed on the drive screw. Rotation of the drive screw may cause advancement of the drive beam to staple and cut tissue.

In some embodiments, the surgical apparatus includes a rotation gear disposed within the distal body portion for rotating the distal end of the distal body portion about the longitudinal axis. The surgical apparatus may further include a drive transfer assembly extending between the proximal and distal body portions. The drive transfer assembly may include first and second horizontal bevel gears disposed about the articulation joint. A first distal bevel gear may be operably connected to the first horizontal bevel gear and a second distal bevel gear may be operably connected the second bevel gear. The first distal bevel gear may be connected to the first drive gear by a first spur gear and the second distal bevel gear may be connected to the rotation gear by a second spur gear. The first and second spur gears, the rotation gear, and the drive gear may be disposed within the same cross-sectional plane. The drive transfer assembly may further includes a first proximal bevel gear operably connected to the first horizontal bevel gear and a second proximal bevel gear operably connected to the second horizontal bevel gear.

The surgical apparatus may further include first and second drive shafts extending through the proximal body portion. The first drive shaft may be operably connected to the first proximal bevel gear and the second drive shaft may be operably connected to the second proximal bevel gear. The surgical apparatus may further include an articulation assembly disposed within the proximal body portion and a pivot member disposed within the articulation joint. The pivot member may be fixedly secured to the distal body portion and pivotally secured to the proximal body portion. The articulation assembly may include a flexible band received about the pivot member. The flexible band may be operably connected to a third drive shaft extending through the proximal body portion. Rotation of the third drive shaft may effectuate articulation of the distal body portion relative to the proximal body portion.

An adapter assembly for connecting a loading unit to a handle assembly is provided is also provided. The adapter assembly includes a proximal body portion defining a longitudinal axis, a distal body portion selectively articulable relative to the proximal body portion, and an articulation assembly for articulating the distal body portion relative to the proximal body portion. The articulation assembly includes a pivot member fixedly secured to the distal body portion and rotatably secured relative to the proximal body portion and a flexible band received about the pivot member and including first and second ends, wherein longitudinal translation of the first and second ends of the flexible band causes articulation of the distal body portion relative to the proximal body portion. The proximal body portion may be configured for operable engagement with a handle assembly and the distal body portion may be configured for operable engagement with a loading unit.

In embodiments, the articulation assembly may further include a connector tube secured to the flexible band and a drive screw in operable engagement with the connector tube. Rotation of the drive screw relative to the connector tube may cause longitudinal translation of the first and second ends of the flexible band. Rotation of the drive screw in a first direction may translate the first end of the flexible band in a first longitudinal direction to articulate the distal body portion in a first direction relative to the proximal body portion. In addition, rotation of the drive screw in a second direction may translate the first end of the flexible band in a second longitudinal direction to articulate the distal body portion in a second direction. A proximal end of the drive screw may be configured for operable connection with a drive shaft of a handle assembly.

In some embodiments, the articulation assembly includes a tensioning mechanism for maintaining the flexible band in tension about the pivot member. The tensioning mechanism may operably engage proximal and distal portion of the flexible band to maintain the flexible band in tension about the pivot member. The tensioning mechanism may include a tensioning housing, a tensioning screw, and a tensioning gear rotatably received within the tensioning housing, the tensioning gear operably engaging the proximal and distal portions of the flexible band to maintain the flexible band in tension about the pivot member. Rotation of the tensioning screw relative to the tensioning housing in a first direction may increase the tension of the flexible band on the pivot member and rotation of the tensioning screw relative to the tensioning housing in a second direction may reduce the tension of the flexible band on the pivot member. The tensioning gear may operably engage the proximal and distal portions of the flexible band to move the proximal and distal portions of the flexible band relative to each other during longitudinal translation of the flexible band.

The adapter assembly may further including a drive assembly extending therethough for actuating a loading unit when the loading unit is secured to distal body portion. The adapter assembly may include a latch mechanism operably received within distal body portion for selectively securing the loading unit to the distal body portion. The loading unit may include a cartridge assembly, an anvil assembly pivotally secured relative to the cartridge assembly between an open position and a closed position, and a plunger assembly for biasing the anvil assembly to the open position.

In addition, an adapter assembly for connecting a loading unit to a handle assembly is also provided. The adapter assembly includes a proximal body portion defining a longitudinal axis, a distal body portion selectively articulable relative to the proximal body portion, and an articulation assembly for moving the distal body portion relative to the proximal body portion. The articulation assembly includes a flexible band for moving the distal body portion relative to the proximal body portion. A first end of the flexible band is operably connected to a drive screw for effecting longitudinal movement of the flexible band.

The adapter assembly may further include a pivot member received between the proximal body portion and the distal body portion, the pivot member being fixed to the distal body portion and movable relative to the proximal body portion. The flexible band may be received about the pivot member to effect movement of the distal body portion relative to the proximal body portion. A tensioning mechanism may be received between first and second ends of the flexible member to move the second end of the flexible band relative to the first end of the flexible band.

Also provided is a surgical stapler including a handle assembly, an elongated body extending from the handle assembly, and a loading unit selectively secured to the elongated body. The loading unit includes a cartridge assembly, an anvil assembly pivotally secured relative to the cartridge assembly between an open position and a closed position, and a plunger assembly for biasing the anvil assembly to the open position, wherein the plunger assembly extends parallel to a longitudinal axis of the loading unit. The plunger assembly may include a plunger configured to engage a flange formed on a proximal end of the anvil assembly. The plunger may be biased distally by a spring.

Further, a surgical stapler including an adapter assembly and a loading unit is provided. The adapter assembly includes a body portion including a tongue and defining a longitudinal opening. The adapter assembly further includes a latch mechanism operably received within the longitudinal opening. The latch mechanism includes a latch member and a spring for biasing the latch mechanism in a distal direction. The loading unit is selectively securable to the adapter assembly and defines a cutout for selectively receiving the tongue and a recess for selectively receiving a distal end of the latch member for selectively securing the loading unit to the adapter assembly.

In embodiments, the loading unit may include an extension defining the cutout and the recess. The latch member may include a proximal portion configured for operable engagement by a user to bias the latch member in a proximal direction. The body portion may include a pair of inwardly extending lips and the extension may define a pair of notches for selectively receiving the respective pair of inwardly extending lips. The distal end of the latch member may be conical. The biasing member may be a compression spring received about a proximal end of the latch member.

The loading unit may further include a locking mechanism for locking the loading unit to the adapter assembly. The locking mechanism may include at least one locking member and the distal body portion of the adapter assembly may define at least one longitudinal bore. A proximal end of the at least one locking member may be selectively receivable within the at least one longitudinal bore to secure the loading unit to the adapter assembly.

The surgical stapler may further include a cartridge assembly selectively engageable to the loading unit, wherein the proximal end of the at least one locking member is received within the at least one longitudinal bore when the cartridge assembly is engaged with the loading unit to secure the loading unit to the adapter assembly. The proximal end of the at least one locking member may be retracted from within the at least one longitudinal bore when the cartridge assembly is separated from the loading unit to permit separation of the loading unit from the adapter assembly. The loading unit may include a carrier defining a longitudinal recess for receiving the cartridge assembly. The at least one locking member may include a distal end slidably disposed within the longitudinal recess engageable by the cartridge assembly when the cartridge assembly is received within the longitudinal recess. Engagement of the cartridge assembly with the distal end of the at least one locking member may move the proximal end of the at least one locking member into the at least one longitudinal bore to secure the loading unit to the adapter assembly.

Also provided is a method of securing a loading unit to an adapter assembly. The method includes aligning a tongue formed on a distal end of an adapter assembly with a cutout formed on a proximal end of a loading unit and receiving the tongue of the adapter assembly within the cutout of the loading unit until a latch member of the adapter assembly is biased within a recess of the loading unit.

In embodiments, aligning the tongue of the adapter assembly with the cutout of the loading unit further includes aligning a pair of inwardly extending lips of the adapter assembly with a pair of notches of the loading unit. Receiving the tongue of the adapter assembly within the cutout of the loading unit further includes receiving the pair of inwardly extending lips of the adapter assembly within the respective pair of notches of the loading unit. The method may further include receiving a cartridge assembly within the loading unit to actuate a locking mechanism to secure the loading unit to the adapter assembly. Receiving the cartridge assembly within the loading unit may include engaging a locking member of the locking mechanism with the cartridge assembly to move the locking member into engagement with the adapter assembly.

In addition, an adapter assembly for a surgical stapler is provided. The adapter assembly includes a proximal body portion and a distal body portion selectively articulable relative to the proximal body portion about an articulation joint. The distal body portion having a diameter and a length. The adapter assembly further includes a drive gear disposed within the distal body portion for rotating a lead screw of a loading unit attached to the distal body portion. The length of the distal body portion is substantially the same as the diameter of the distal body portion.

In embodiments, the adapter assembly further includes a rotation gear disposed within the distal body portion for rotating a distal housing of the distal body portion about a longitudinal axis of the distal body portion. The adapter assembly may further include a drive transfer assembly extending between the proximal and distal body portions. The drive transfer assembly may include first and second horizontal bevel gears disposed within the articulation joint, a first distal bevel gear operably connected to the first horizontal bevel gear, and a second distal bevel gear operably connected the second bevel gear. The first distal bevel gear may be connected to the drive gear by a first spur gear and the second distal bevel gear may be connected to the rotation gear by a second spur gear. The first and second spur gears, the rotation gear, and the drive gear may be disposed within the same cross-sectional plane. The drive transfer assembly may further include a first proximal bevel gear operably connected to the first horizontal bevel gear and a second proximal bevel gear operably connected to the second horizontal bevel gear.

The adapter assembly may include first and second drive shafts extending through the proximal body portion. The first drive shaft may be operably connected to the first proximal bevel gear and the second drive shaft may be operably connected to the second proximal bevel gear. The adapter assembly may further include an articulation assembly disposed within the proximal body portion. The articulation assembly may include a flexible band received about the articulation joint. A proximal end of the proximal body portion is configured for operable connection to a handle assembly and a distal end of the distal body portion is configured for operable connection with a loading unit.

BRIEF DESCRIPTION OF THE DRAWINGS

Embodiments of the present disclosure are described herein with reference to the accompanying drawings, wherein:

FIG. 21 is an enlarge perspective side view of the distal end of the adapter assembly and the proximal end of the loading unit shown in FIG. 1, as the loading unit is secured to the adapter assembly;

FIG. 22 is a perspective side view of the distal end of the adapter assembly and the proximal end of the loading unit shown in FIG. 21, with the loading unit secured to the adapter assembly;

FIG. 24 is a perspective side view of a drive beam of the loading unit shown in FIG. 1;

FIG. 25 is a cross-sectional side view of the drive beam shown in FIG. 24;

FIG. 26 is a cross-sectional perspective end view of the drive beam shown in FIG. 24;

FIG. 27 is a perspective side view of the distal end of the adapter assembly and a proximal end of the actuation assembly shown in FIG. 16, further including a locking mechanism in a first or distal position;

FIG. 28 is a perspective view of the distal end of the adapter assembly, the proximal end of the actuation assembly, and the locking mechanism shown in FIG. 27, further including a proximal end of the cartridge assembly shown in FIG. 1, with the locking mechanism in the second or proximal position;

FIG. 34 is a perspective side view of the loading unit shown in FIG. 32;

DETAILED DESCRIPTION OF EMBODIMENTS

Figure 1:
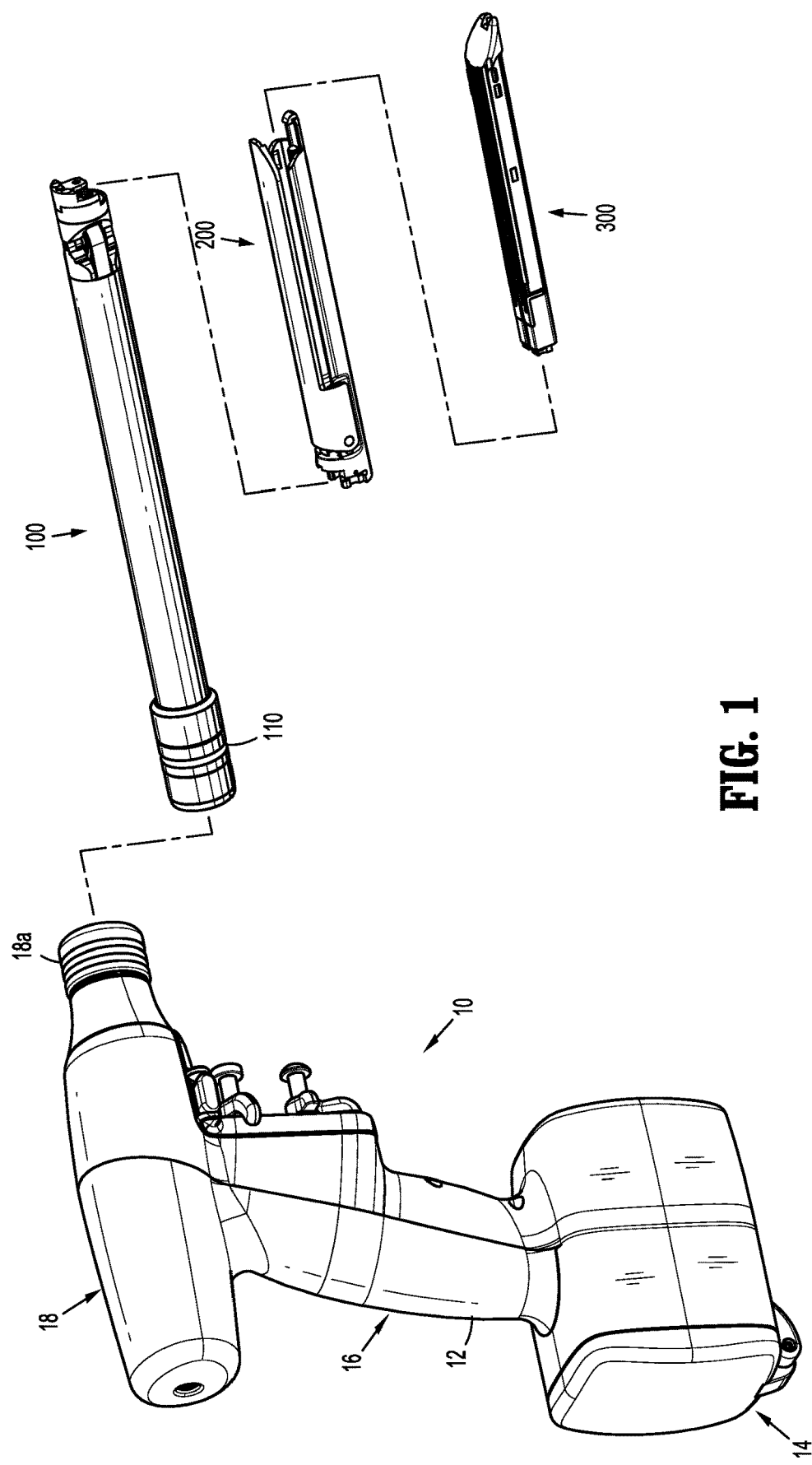
FIG. 1 is a perspective view of an electromechanical surgical stapling device including an adapter assembly, loading unit and cartridge assembly, in accordance with an embodiment of the present disclosure, and a powered handle assembly.

Embodiments of the presently disclosed adapter assembly and loading units for surgical devices and/or handle assemblies are described in detail with reference to the drawings, in which like reference numerals designate identical or corresponding elements in each of the several views. As used herein the term "distal" refers to that portion of the adapter assembly or surgical device, or component thereof, farther from the user, while the term "proximal" refers to that portion of the adapter assembly or surgical device, or component thereof, closer to the user.

With reference to FIG. 1, an adapter assembly in accordance with an embodiment of the present disclosure, shown generally as adapter assembly 100, and a loading unit according to an embodiment of the present disclosure, shown generally as loading unit 200, are configured for selective connection to a powered hand-held electromechanical instrument, shown generally as handle assembly 10. The adapter assembly 100 is configured for selective connection with the handle assembly 10, and, the loading unit 200 is configured for selective connection with the adapter assembly 100. As will be shown and described in detail below, the loading unit 200 is a multiple use loading unit ("MULU") configured to selectively receive a replaceable loading unit, i.e., cartridge assembly 300. The adapter assembly 100, the loading unit 200 and the cartridge assembly 300 operate to staple and cut tissue. Although shown and described as being formed independent of the handle assembly 10, it is envisioned that the aspects of the adapter assembly 100 may be directly incorporated into the handle assembly 10.

Figure 2:
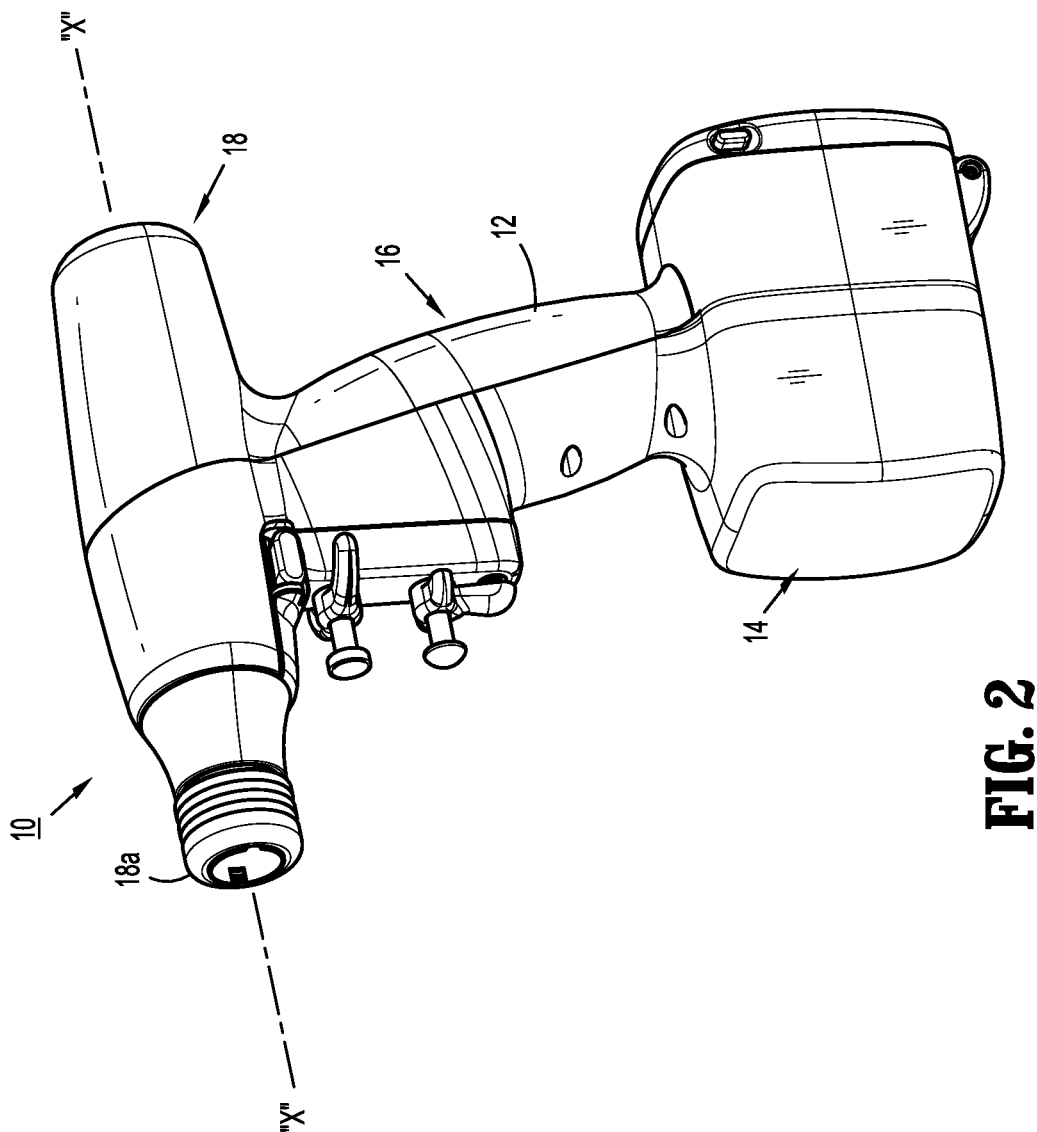
FIG. 2 is a perspective view of the powered handle assembly shown in FIG. 1.

As illustrated in FIGS. 1 and 2, the handle assembly 10 includes a handle housing 12 having a lower housing portion 14, an intermediate housing portion 16 extending from and/or supported on the lower housing portion 14, and an upper housing portion 18 extending from and/or supported on the intermediate housing portion 16. A distal half-section of the upper housing portion 18 defines a nose or connecting portion 18a configured to accept a corresponding drive coupling assembly 110 of the adapter assembly 100. For a detailed description of the structure and function of an exemplary powered hand-held electromechanical instrument, please refer to commonly owned U.S. Pat. Appl. Publ. No. 2012/0253329 ("the '329 application") and U.S. Pat. Appl. Publ. No. 2012/0323226 ("the '226 application), the contents of which are incorporated by reference herein in their entirety.

Figure 3:
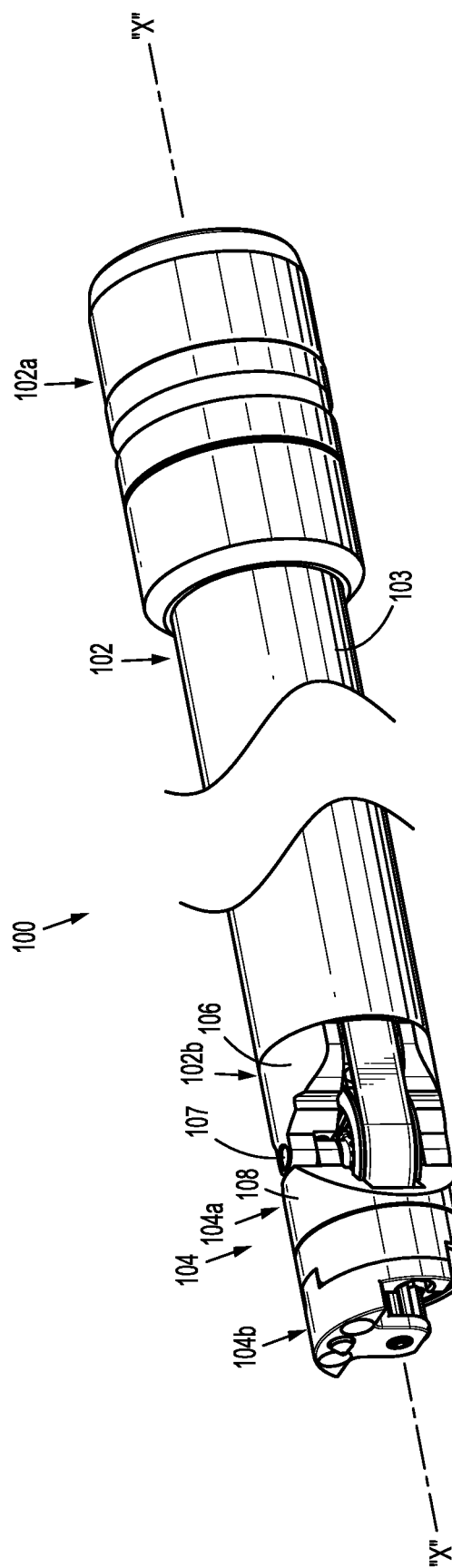
FIG. 3 is a perspective side view of the adapter assembly shown in FIG. 1.
Figure 4:
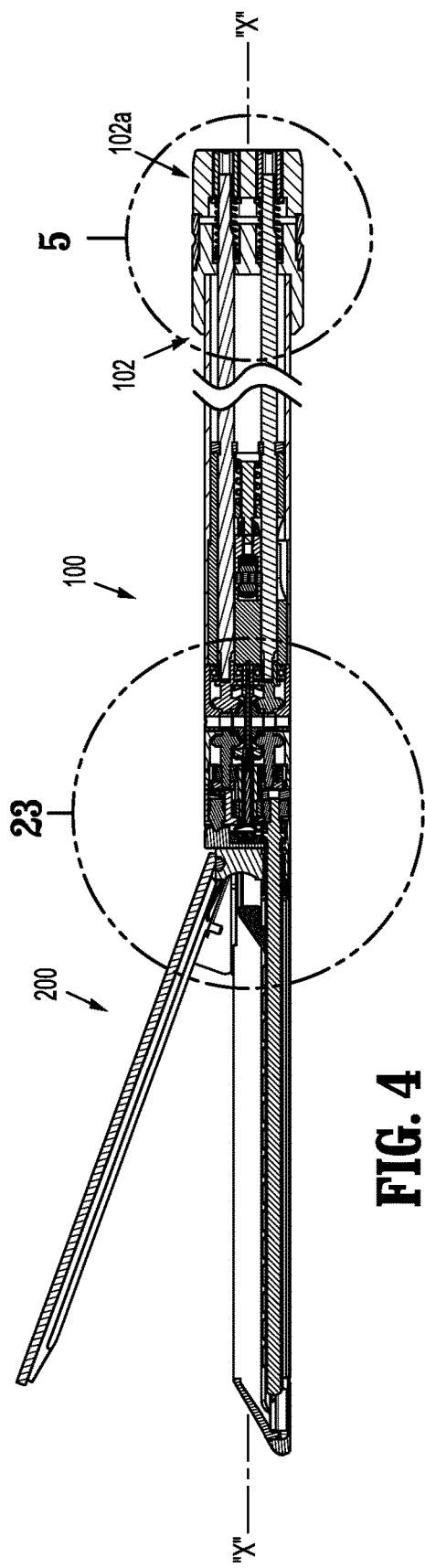
FIG. 4 is a cross-sectional side view of the adapter assembly and the loading unit shown in FIG. 1.

The adapter assembly 100 will now be described with reference to FIGS. 3-18. Referring initially to FIG. 3, the adapter assembly 100 includes a proximal body portion 102 and a distal body portion 104. The proximal body portion 102 includes a proximal end 102a configured for operable connection to the connecting portion 18a (FIG. 2) of the handle assembly 10 (FIG. 2) and a distal end 102b pivotally connected to a proximal end 104a of the distal body portion 104 at an articulation joint 105 (FIG. 3). More particularly, and as will be described in further detail below, a first connector housing 106 is disposed on the distal end 102b of the proximal body portion 102 and is pivotally secured to a distal connector housing 108 disposed on the proximal end 104a of the distal body portion 104 at the articulation joint 105 by a pivot pin 107. The distal body portion 104 includes a distal end 104b configured for selective connection to the loading unit 200 (FIG. 1). As will also be described in further detail below, the compact length of the distal body portion 104 allows for greater manipulation of an attached loading unit 200 within a body cavity (not shown) during a surgical procedure. The ability of the distal body portion 104 to pivot through an arc of one-hundred eight degrees (180°) relative to the proximal body portion 102 allows for further manipulation of an attached loading unit 200.

The proximal body portion 102 of the adapter assembly 100 includes the drive coupling assembly 110 (FIG. 5) and an articulation assembly 130 (FIG. 12) operably connected to the drive coupling assembly 110 and maintained within an outer sleeve 103 of the proximal body portion 102. A drive transfer assembly 160 (FIG. 15) extends between the proximal and distal body portions 102, 104 of the adapter assembly 100 and operably connects the drive coupling assembly 110 to a drive assembly 190 (FIG. 15) disposed within the distal body portion 104 of the adapter assembly 100.

With reference to FIGS. 4-10, as shown, the drive coupling assembly 110 has a cylindrical profile and is configured to selectively secure the adapter assembly 100 to the handle assembly 10 (FIG. 1). The drive coupling assembly 110 includes a connector housing 112 and a connector extension 114 fixedly connected to the connector housing 112 by an annular ring 113. The annular ring 113 may include a groove 113a or other feature for securing the adapter assembly 100 to the handle assembly 10. The connector extension 114 may include a notch 114a or other feature formed in an outer surface thereof for facilitating alignment of the adapter assembly 100 with the connector portion 18a of the handle assembly 10.

Figure 5:
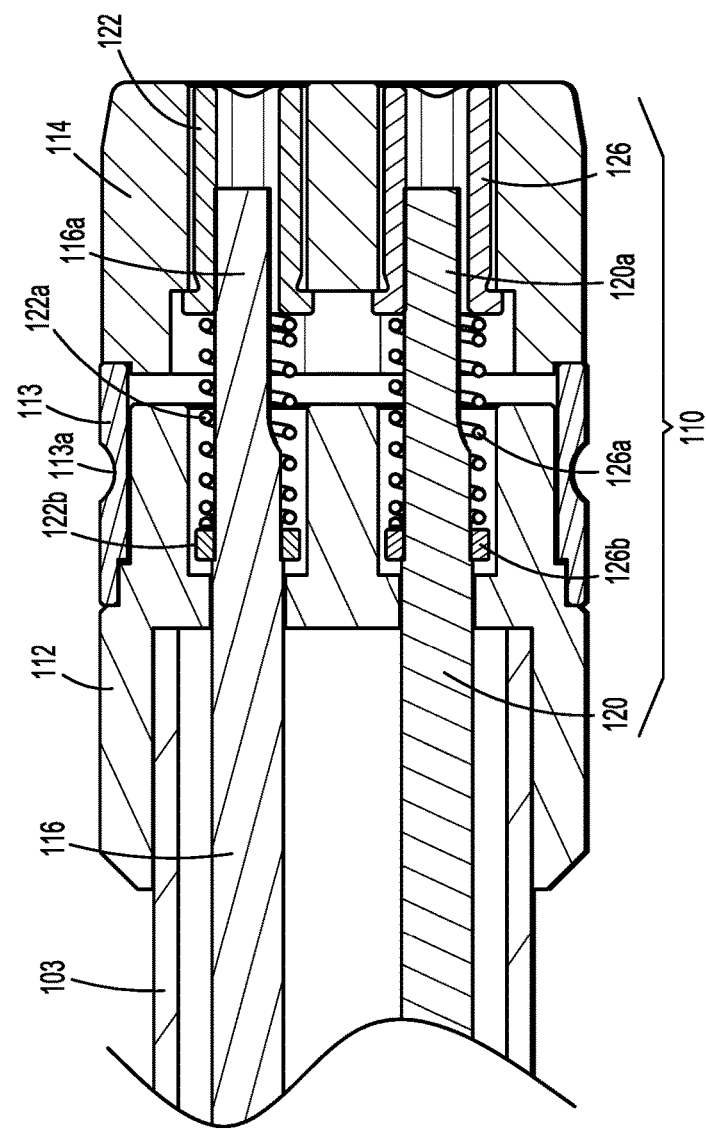
FIG. 5 is an enlarged view of the indicated area of detail shown in FIG. 4.
Figure 6:
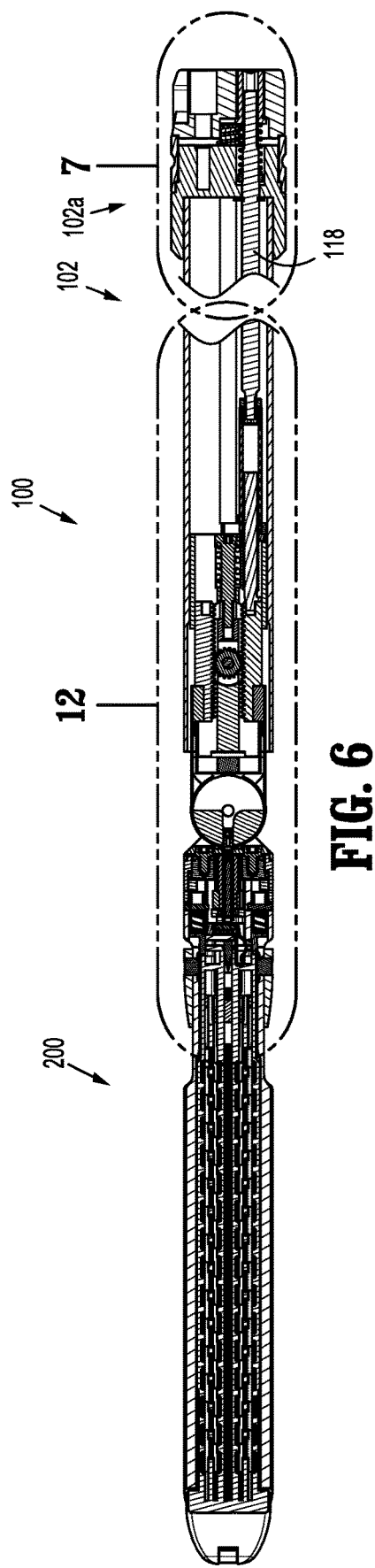
FIG. 6 is a cross-sectional top view of the adapter assembly, the loading unit, and cartridge assembly shown in FIG. 1.
Figure 7:
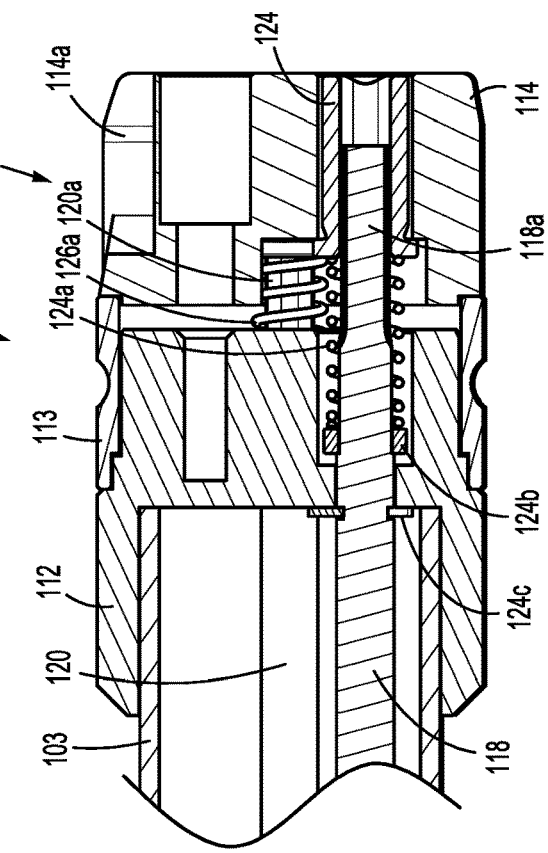
FIG. 7 is an enlarged view of the indicated area of detail shown in FIG. 6.
Figure 8:
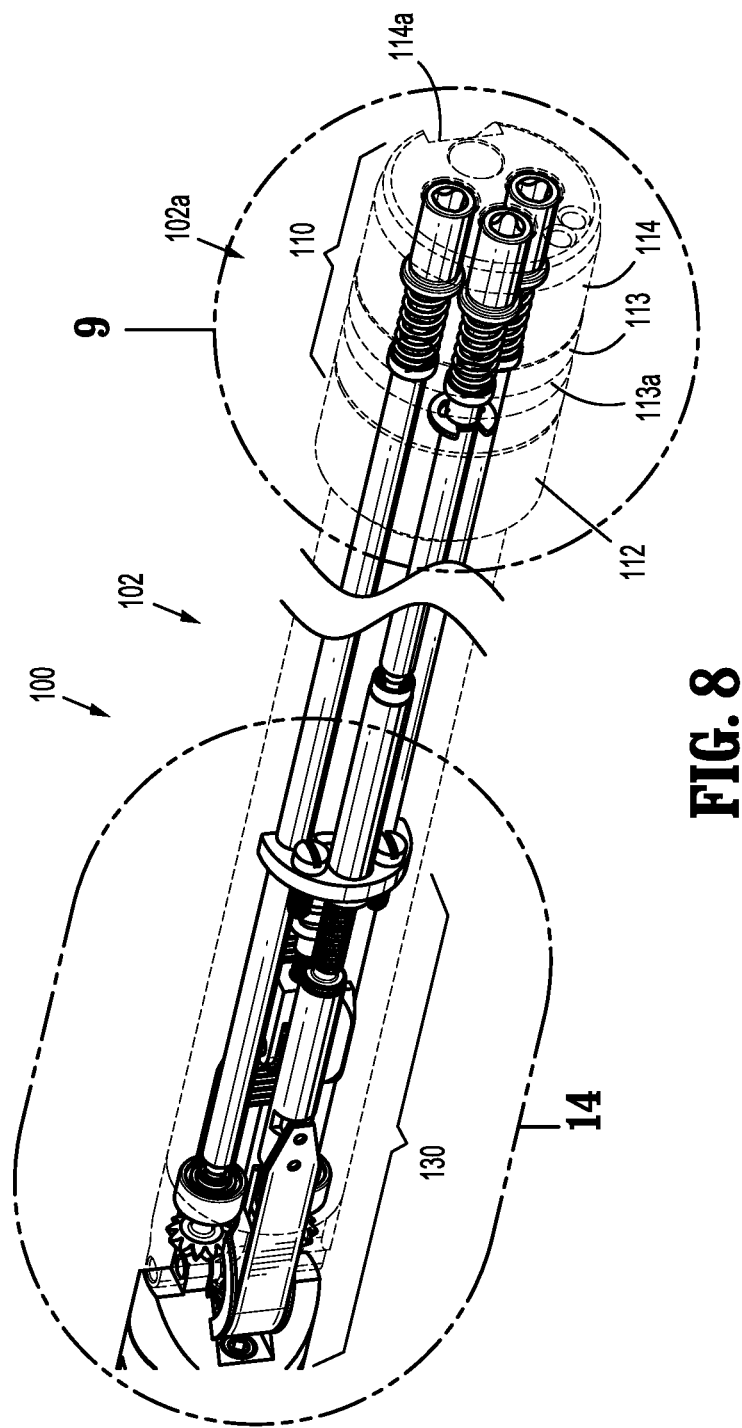
FIG. 8 is a perspective end view of the adapter assembly shown in FIG. 1 with an outer sleeve removed and a proximal end shown in phantom.
Figure 9:
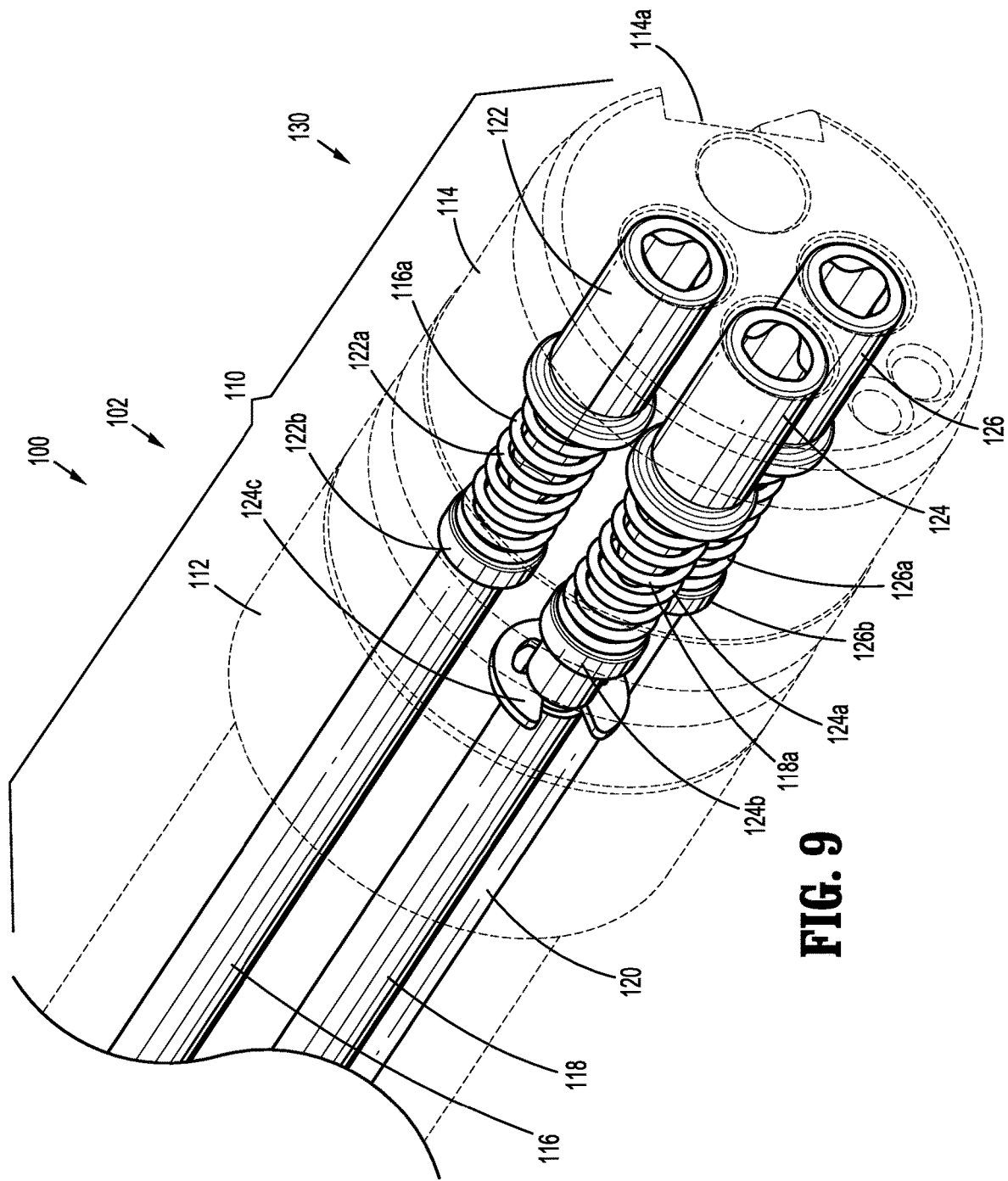
FIG. 9 is an enlarged view of the indicated area of detail shown in FIG. 8.

The connector housing 112 and the connector extension 114 operate to rotatably support a first drive shaft 116 (FIG. 5), a second drive shaft 118 (FIG. 7), and a third drive shaft 120 (FIG. 5). The connector housing 112 and the connector extension 114 of the drive coupling assembly 110 also rotatably support the first, second, and third connector sleeves 122 (FIG. 5), 124 (FIG. 7), and 126 (FIG. 5), respectively. The first, second, and third connector sleeves 122, 124, and 126 are configured to mate with the respective first, second, and third drive connectors (not shown) of the handle assembly 10 (FIG. 1) and are further configured to mate with a proximal end 116a, 118a, 120a of the respective first, second, and third drive shafts 116 (FIG. 5), 118 (FIG. 7), and 120 (FIG. 5) of the adapter assembly 100.

The drive coupling assembly 110 also includes first, second and third biasing members 122a (FIG. 5), 124a (FIG.

7), and 126a (FIG. 5) disposed distally of the respective first, second, and third connector sleeves 122, 124, and 126. The first, second, and third biasing members 122a, 124a, 126a are disposed about the respective first, second, and third drive shafts 116, 118, and 120 to facilitate engagement of the respective first, second, and third connector sleeves 122, 124, and 126 with respective first, second, and third rotatable drive connectors (not shown) of the handle assembly 10 (FIG. 1) when the adapter assembly 100 is connected to the handle assembly 10. In particular, the first, second, and third biasing members 122a, 124a, and 126a function to bias the respective first, second, and third connector sleeves 122, 124, and 126 in a proximal direction. First, second, and third washers 122b, 124b, and 126b are received about the respective proximal ends 116a, 118a, and 120a of the respective first, second, and third drive shafts 116, 118, and 120 to maintain the respective first, second, and third biasing members 122a, 124a, and 126a relative to the respective first, second, and third drive shafts 116, 118, and 120. A spring clip 124c (FIG. 7) is received about the second drive shaft 118 adjacent the proximal end 118a of the second drive shaft 118 to secure the second drive shaft 118 relative to the connector housing 112 of the drive coupling assembly 110.

For a detailed description of an exemplary drive coupling assembly, reference may be made to the '329 application, the content of which was previously incorporated by reference herein.

Figure 10:
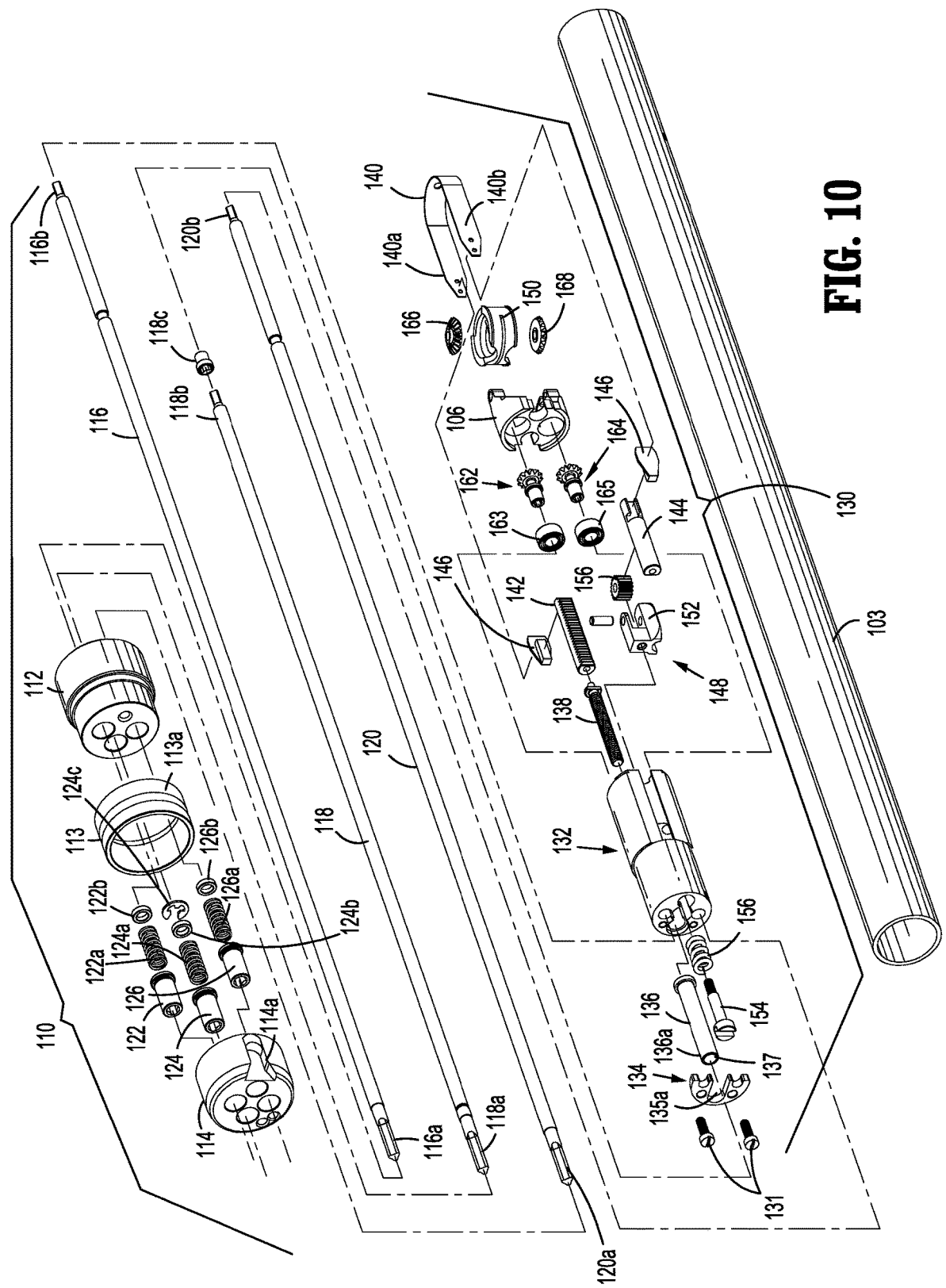
FIG. 10 is an exploded perspective view of a proximal body portion of the adapter assembly shown in FIG. 1.
Figure 11:
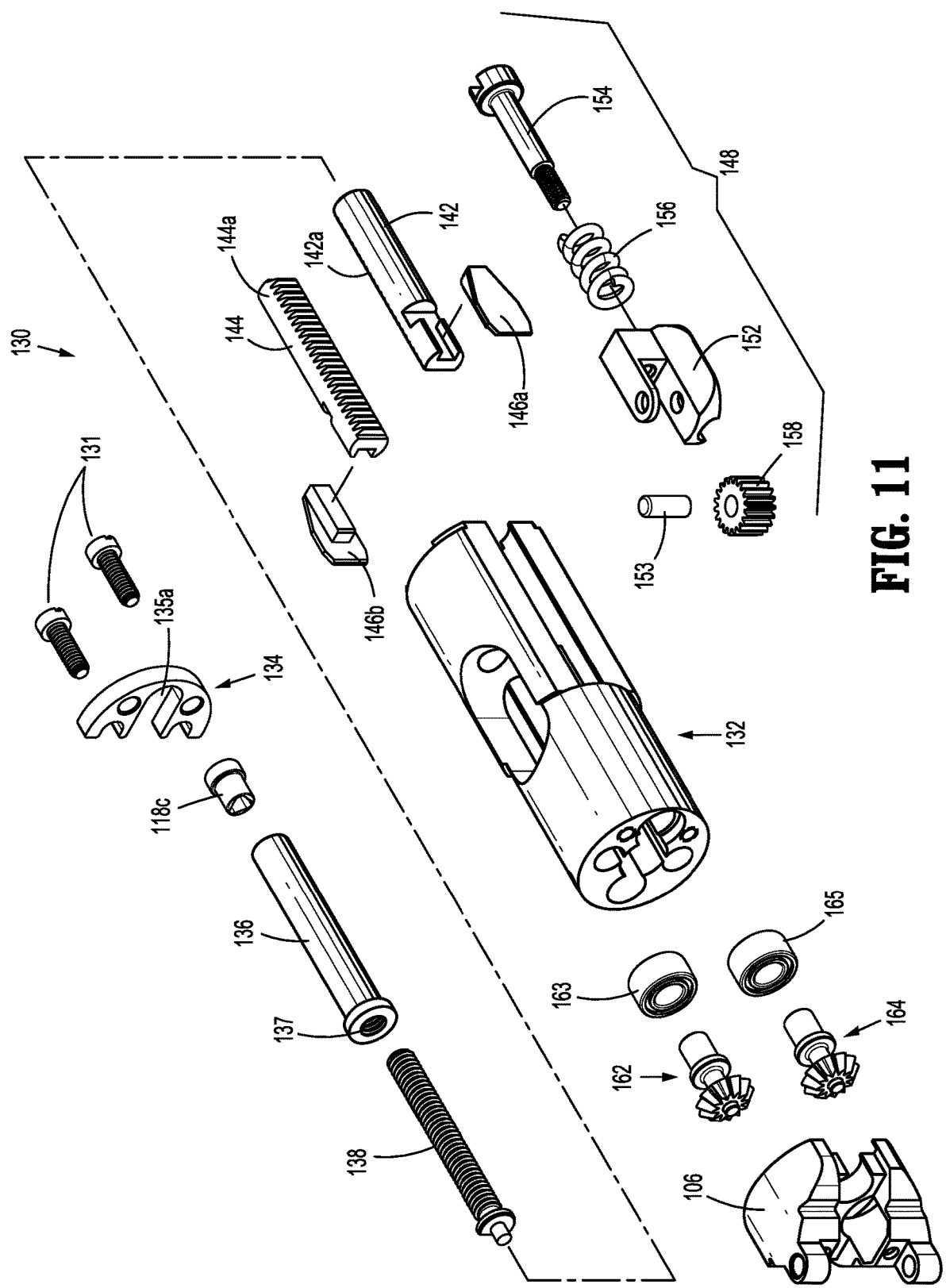
FIG. 11 is an exploded perspective view of an articulation assembly of the adapter assembly shown in FIG. 1.
Figure 12:
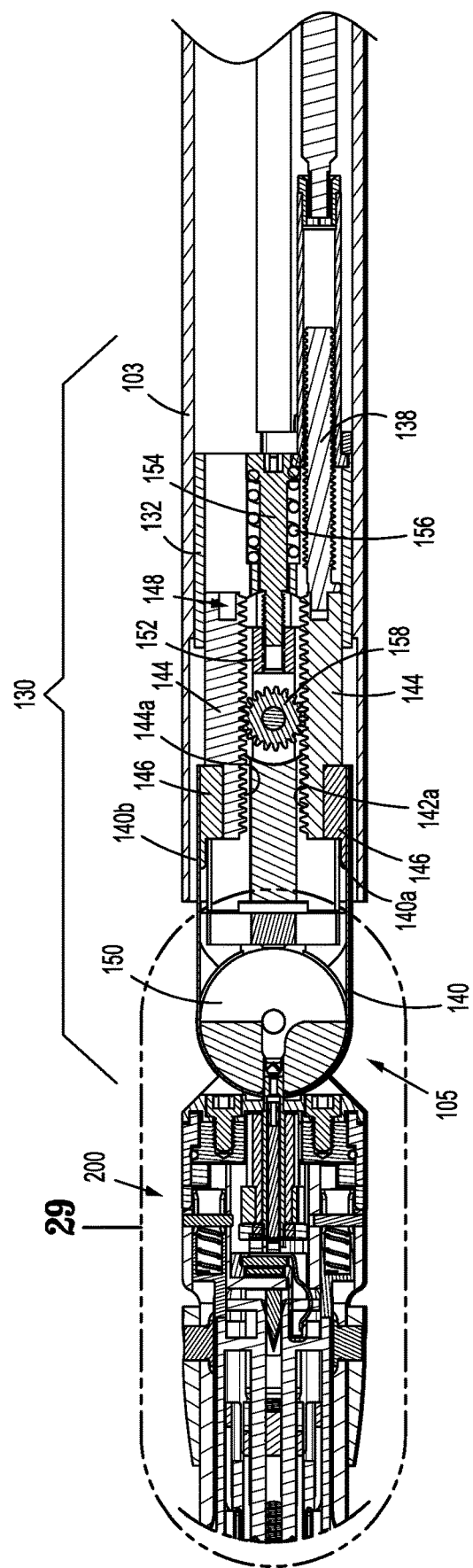
FIG. 12 is a cross-sectional top view of a distal end of the adapter assembly and the loading unit shown in FIG. 1.
Figure 13:
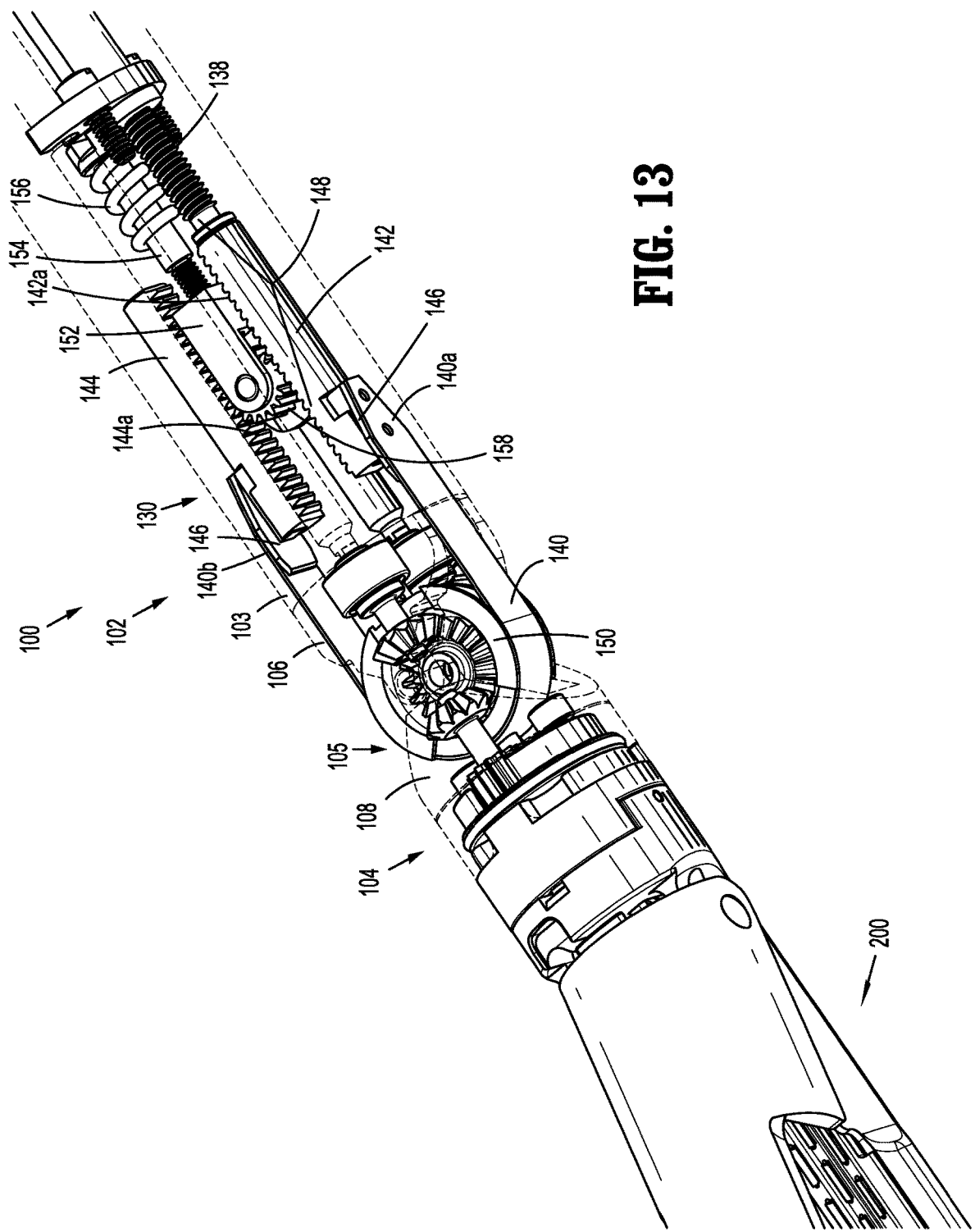
FIG. 13 is a perspective top view of the distal end of the adapter assembly and a proximal end of the loading unit shown in FIG. 1, with connector housings and the outer sleeve of the adapter assembly shown in phantom.
Figure 14:
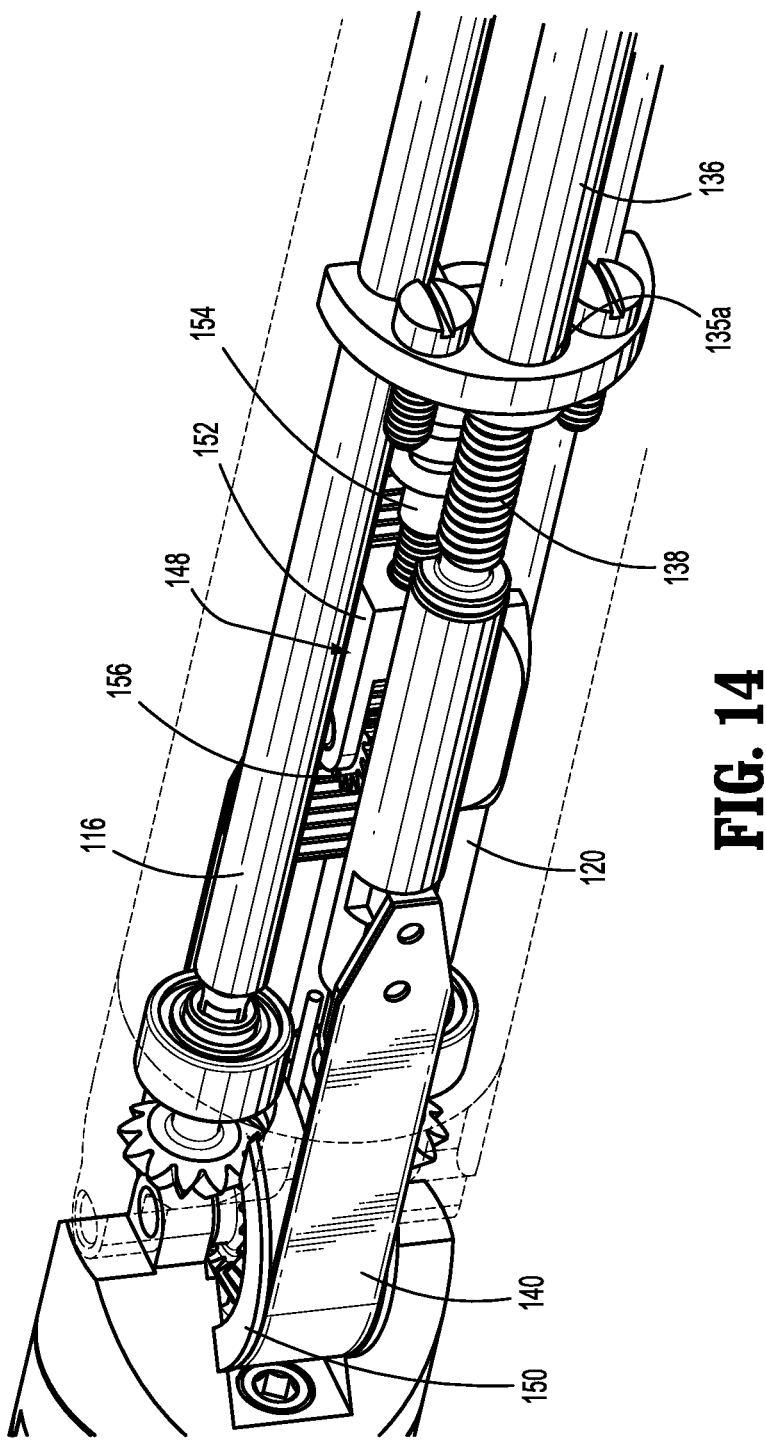
FIG. 14 is a perspective side view of the articulation assembly shown in FIG. 11.

With reference now to FIGS. 10-16, the articulation assembly 130 effects articulation of the distal body portion 104 (FIG. 3) of the adapter assembly 100 relative to the proximal body portion 102 (FIG. 3) of the adapter assembly 100. With particular reference to FIGS. 10 and 11, the articulation assembly 130 includes an articulation housing 132 and a support plate 134 secured to a proximal end of the articulation housing 132 by a pair of screws 131. A connector tube 136 extends through an opening 135a in the support plate 134 and includes a threaded inner surface 137 for receiving a threaded connector screw 138. A proximal end 136a of the connector tube 136 operably engages an adapter member 118c that is secured to the distal end 118b (FIG. 10) of the second drive shaft 118.

The articulation assembly 130 further includes a flexible band 140 slidably disposed relative to the articulation housing 132. A first end 140a of the flexible band 140 is secured to the connector screw 138 by a first connector 142 and a second end 140b of the flexible band 140 is secured to a second connector 144. More particularly, the first and second connectors 142, 144 are each secured to the flexible band 140 by first and second adaptors 146a, 146b which are fixedly secured to the first and second ends 140a, 140b, respectively, of the flexible band 140 and operably secured to the respective first and second connectors 142, 144. The first and second adaptors 146a, 146b may be secured to the flexible band 140 by adhesive, welding, mechanical fasteners, or in any other suitable manner. Alternatively, the first and second connectors 142, 144 are directly secured to the flexible band 140 without the use of the first and second adaptors 146a, 146b. Each of the first and second connectors 142, 144 may be in the form of a gear rack each including a toothed surface 142a, 144a for operable engagement with a tensioning mechanism 148.

Figure 15:
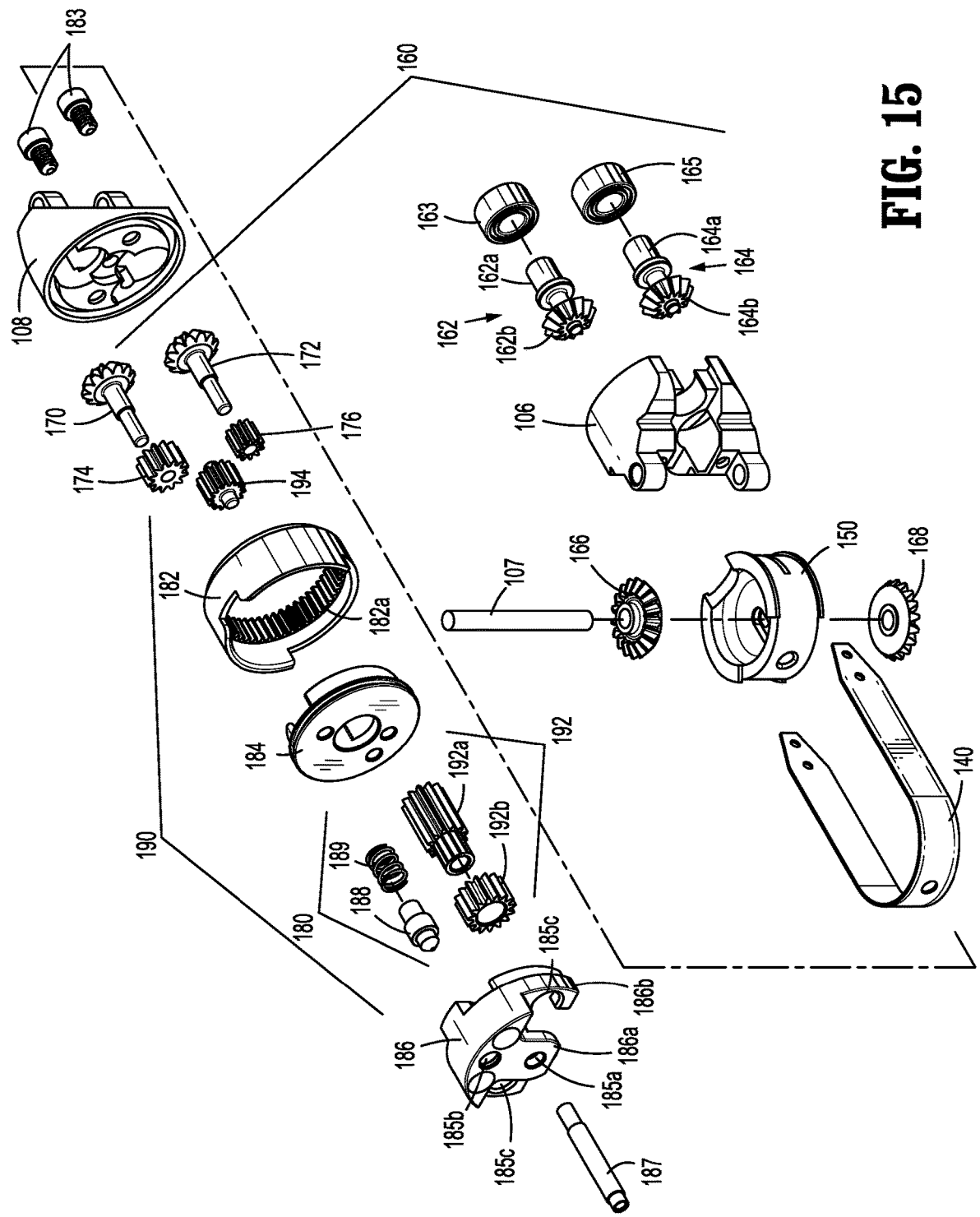
FIG. 15 is an exploded perspective view of a distal body portion of the adapter assembly shown in FIG. 1.

Turning briefly to FIG. 15, the flexible band 140 is received about a pivot member 150. The pivot member 150 is secured between the proximal connector housing 106 of the proximal body portion 102 and the distal connector housing 108 of the distal body portion 104 by the pivot pin 107. The pivot member 150 is pivotal relative to the proximal connector housing 106 and is fixedly secured to the distal connector housing 108. Rotation of the pivot member 150 about the pivot pin 107 through operation of the articulation assembly 130, i.e., longitudinal movement of the flexible band 140 relative to the pivot member 150, causes articulation of the distal body portion 104 of the adapter assembly 100 relative to the proximal body portion 102 of the adapter assembly 100.

During use, the articulation assembly 130 is actuated through rotation of the second drive shaft 118. In particular, rotation of the second drive shaft 118 causes rotation of the connector tube 136. Rotation of the connector tube 136 causes longitudinally movement of the connector screw 138. When the connector tube 136 is rotated in a first direction, the connector screw 138 is moved longitudinally in a proximal direction and when the connector tube 136 is rotated in a second direction (opposite the first direction), the connector screw 138 is moved in a distal direction. As noted above, the connector screw 138 is connected to the first connector 142 and the first connector 142 is connected to the flexible band 140. Thus, longitudinal movement of the first connector 142 causes corresponding movement of the flexible band 140. Since the flexible band 140 is received or fixedly connected about the pivot member 150, longitudinal movement of the flexible band 140 causes corresponding pivoting of the pivot member 150.

With continued reference to FIGS. 10-14, the flexible band 140 is maintained in tension about the pivot member 146 by the tensioning mechanism 148 received between the first and second connectors 142, 144 of the articulation assembly 130. The tensioning mechanism 148 includes a tensioning housing 152, a tensioning screw 154, a biasing member 156, and a tensioning gear 158 rotatably received within the tensioning housing 152 by a pivot pin 153. The tensioning housing 152 is adjustably secured to the tensioning screw 154 such that the tensioning housing 152 is slidably disposed within the articulation housing 132 between the first and second connectors 142, 144. The biasing member 156 is received about the tensioning screw 154 and engages the articulation housing 132. The biasing member 156 applies a force on the tensioning screw 154 which pulls the tensioning housing 152 in a proximal direction. The force applied by the biasing member 156 on the tensioning screw 154 can be adjusted by rotating the tensioning screw 154 and acts on the first and second connectors 142, 144 through the tensioning gear 158 to keep the first and second connectors 142, 144 and the flexible band 140 in tension, thereby ensuring that the first and second connectors 142, 144 move uniformly during operation of the articulation assembly 130. In this manner, the tensioning mechanism 148 ensures that the first connector 142 is advanced or retracted at the same rate as the second connector 144 is retracted or advanced. The tensioning mechanism 148 may also operate to maintain frictional engagement between the flexible band 140 and the pivot member 150. Alternatively, the flexible band 140 is secured to the pivot member 150 using an adhesive, mechanical fastener or other in any other suitable manner.

Figure 16:
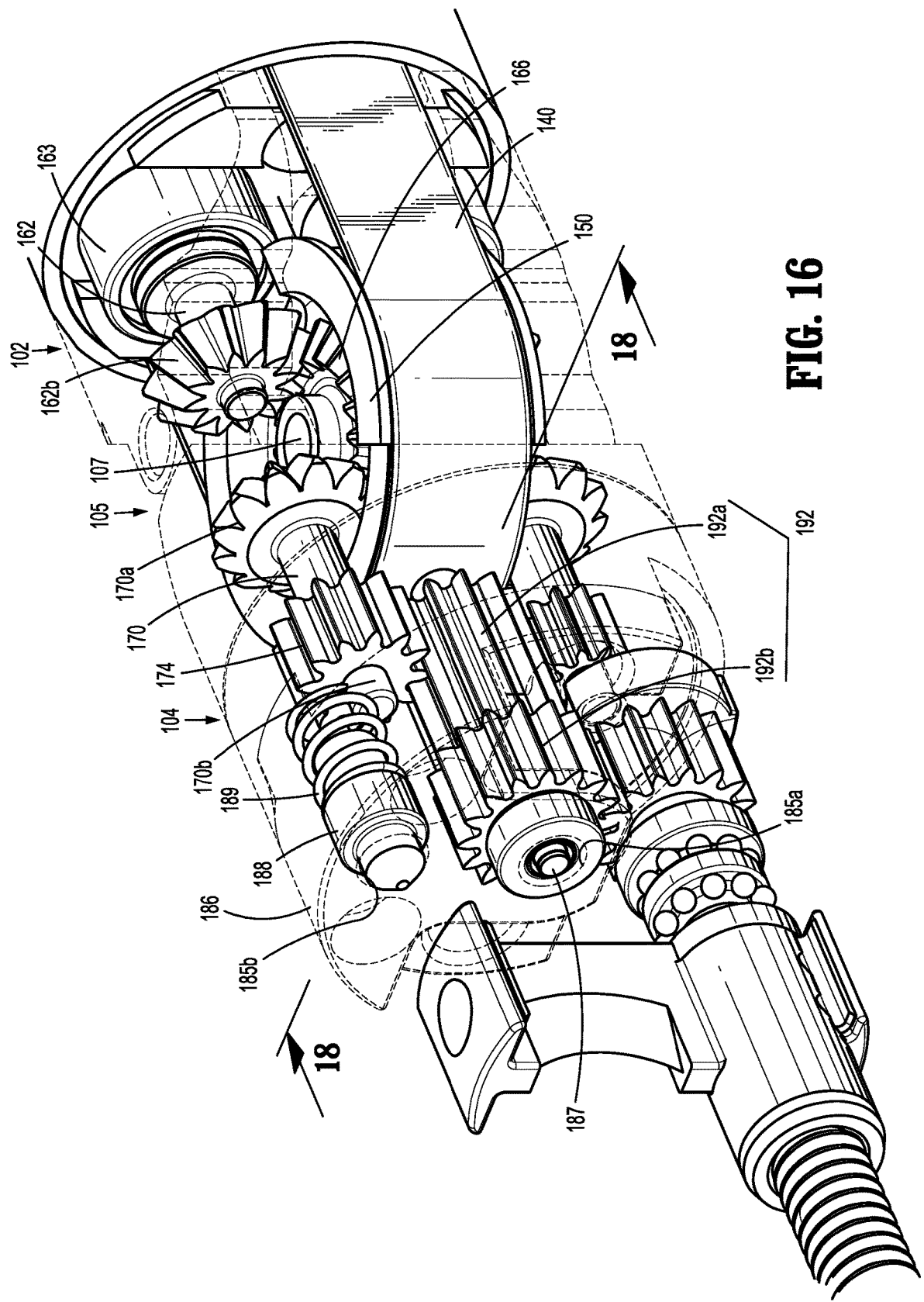
FIG. 16 is an enlarged perspective view of the distal end of the adapter assembly and an actuation assembly of the loading unit shown in FIG. 1, with housings shown in phantom.
Figure 17:
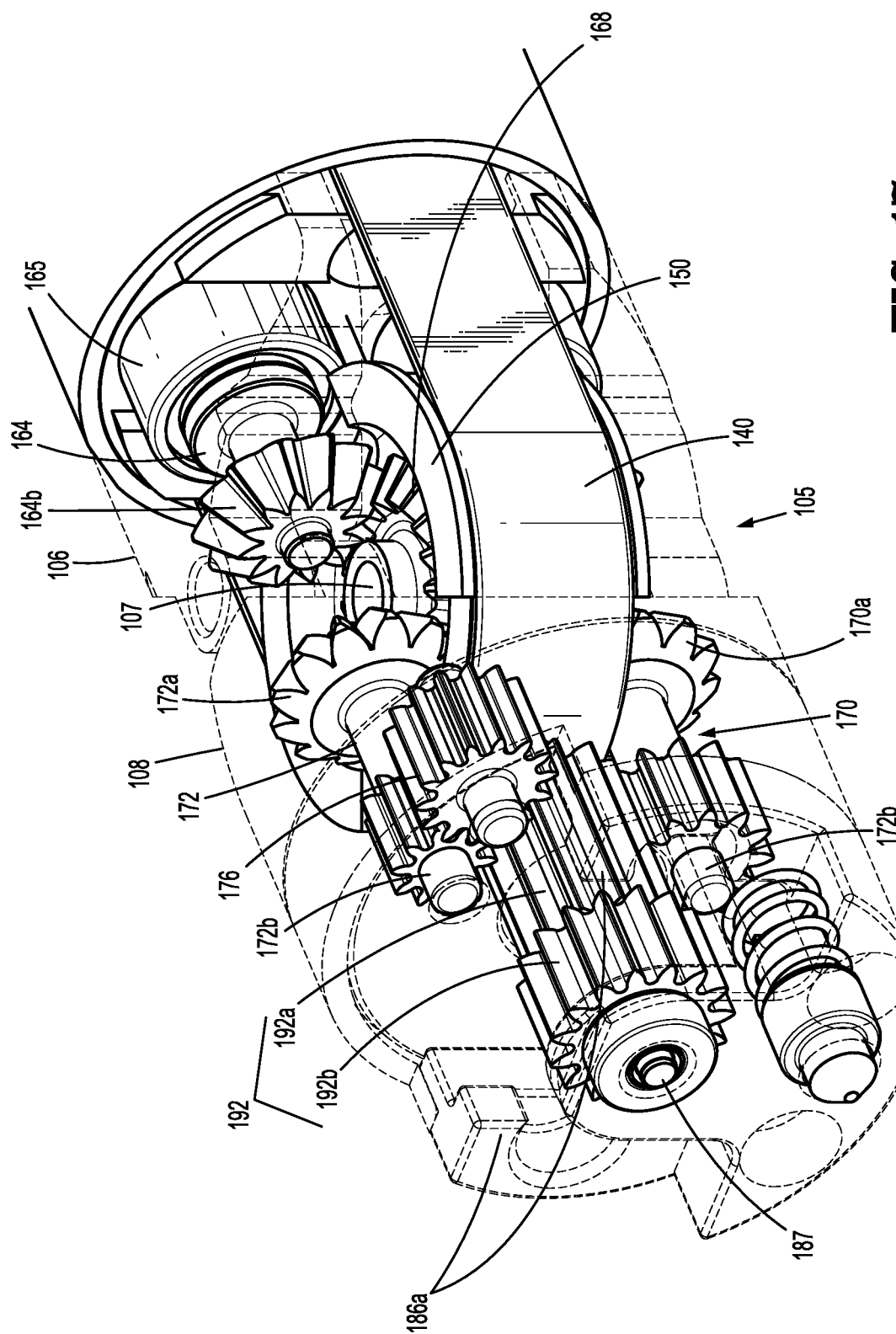
FIG. 17 is an enlarged perspective view of the distal end of the adapter assembly shown in FIG. 1 with the housings shown in phantom.
Figure 18:
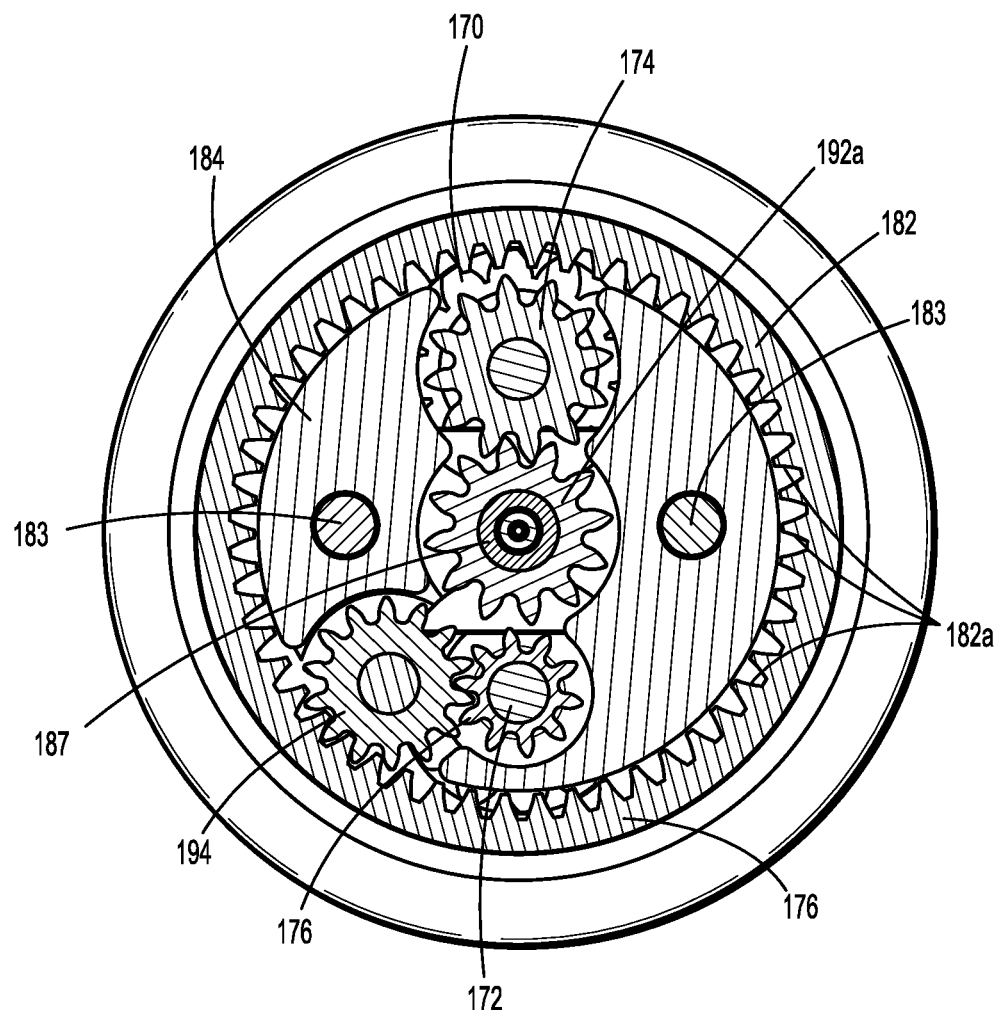
FIG. 18 is a cross-sectional end view taken along line 18-18 in FIG. 16.

With particular reference again to FIG. 15 and additional reference to FIGS. 16-18, the drive transfer assembly 160 operably connects the drive coupling assembly 110 (FIG. 10) with the drive assembly 190. The drive transfer assembly 160 includes first and second proximal bevel gears 162, 164, first and second horizontal bevel gears 166, 168, and first and second distal bevel gears 170, 172. The first proximal bevel gear 162 is rotatably supported within the proximal connector housing 106 by a first bearing assembly 163. A first end 162a of the first proximal bevel gear 162 operably engages the distal end 116b (FIG. 10) of the first drive shaft 116 of the drive coupling assembly 110 and a second end 162b of the first proximal bevel gear 162 engages the first horizontal bevel gear 166. The second proximal bevel gear 164 is rotatably supported within the proximal connector housing 106 by a second bearing assembly 165. A first end 164a of the second proximal bevel gear 164 operably engages the distal end 120b (FIG. 10) of the third drive shaft 120 of the drive coupling assembly 110 and a second end 164b of the second proximal bevel gear 164 engages the second horizontal bevel gear 168.

The first and second horizontal bevel gears 166, 168 are rotatably supported within the pivot member 150 of the articulation assembly 130 (FIG. 10) about the pivot pin 107. The first horizontal bevel gear 166 operably engages a first end 170a of the first distal bevel gear 170 and the second horizontal bevel gear 168 operably engages a first end 172a of the second distal bevel gear 170. The first and second distal bevel gears 170, 172 are rotatably supported within the distal connector housing 108. A second end 170b of the first distal bevel gear 170 includes or supports a first spur gear 174 and a second end 172b of the second distal bevel gear 172 includes or supports a second spur gear 176. In this manner, power transmission between the proximal and distal body portions 102, 104 occurs within the articulation joint 105.

The drive transfer assembly 160 operates to transfer the rotational motion from the first and third drive shafts 116, 120 (FIG. 10) of the drive coupling assembly 110 in the proximal body portion 102 of the adapter assembly 100 to rotational motion of the respective first and second spur gears 174, 176 within the distal body portion 104 of the adapter assembly 100. As will be described in further detail below, rotation of the first spur gear 174 causes actuation of the loading unit 200 (FIG. 1) and rotation of the second spur gear 176 causes rotation of the loading unit 200 (FIG. 1) about the longitudinal axis "x" of the adapter assembly 100.

With particular reference to FIG. 16, the first drive shaft 116 (FIG. 10) rotates the first proximal bevel gear 162 in a first direction about a first longitudinal axis (not shown) extending parallel to the longitudinal axis "x" of the adapter assembly 100. Engagement between the first proximal bevel gear 162 and the first horizontal bevel gear 166 causes the first horizontal bevel gear 166 to rotate about a longitudinal axis (not shown) of the pivot pin 107, i.e., perpendicular to the longitudinal axis "x" of the adapter assembly 100. Engagement between the first horizontal bevel gear 166 and the first distal bevel gear 170 causes rotation of the first spur gear 174 in a second direction about the first longitudinal axis (not shown) of the adapter assembly 100 when the proximal and distal body portions 102, 104 (FIG. 3) of the adapter assembly 100 are axially aligned. The drive transfer assembly 160 permits the transfer of rotational motion from the first drive shaft 116 to the first spur gear 174 throughout articulation of the distal body portion 104 of the adapter assembly 100 relative to the proximal body portion 102 of the adapter assembly 100.

With particular reference to FIG. 17, the third drive shaft 120 (FIG. 10) rotates the second proximal bevel gear 164 in a first direction about a second longitudinal axis (not shown) extending parallel to the longitudinal axis "x" of the adapter assembly 100. Engagement between the second proximal bevel gear 164 and the second horizontal bevel gear 168 causes the second horizontal bevel gear 168 to rotate about the longitudinal axis (not shown) of the pivot pin 107, i.e., perpendicular to the longitudinal axis "x" of the adapter assembly 100. Engagement between the second horizontal bevel gear 168 and the second distal bevel gear 172 causes rotation of the second spur gear 176 in a second direction about the second longitudinal axis (not shown) of the adapter assembly 100 when the proximal and distal body portions 102, 104 of the adapter assembly 100 are axially aligned. The drive transfer assembly 160 permits the transfer of rotational motion from the third drive shaft 120 to the second distal spur gear 176 throughout articulation of the distal body portion 104 of the adapter assembly 100 relative to the proximal body portion 102 of the adapter assembly 100.

With continued reference to FIGS. 15-17, the distal body portion 104 of the adapter assembly 100 includes a cylindrical housing 182 rotatably supported relative to the distal connector housing 108, a support plate 184 securely supported on or connected to the distal connector housing 108, and a latch housing 186 securely supported to the cylindrical housing 182. The cylindrical housing 182 includes a toothed inner surface 182a for effecting rotation of the cylindrical housing 182 and the latch housing 186. Although shown secured to the distal connector housing 108 by a pair of screws 183, the support plate 184 may be secured to the distal connector housing 108 in any suitable manner.

The latch housing 186 of the distal body portion 104 of the adapter assembly 100 is configured for selective connection with the loading unit 200. More particularly, the latch housing 186 includes a tongue 186a and a pair of inwardly extending lips 186b. As will be described in further detail below, the tongue 186a and the lips 186b cooperate to engage the loading unit 200. The latch housing 186 defines a first longitudinal opening 185a for receiving a pivot pin 187 and a second longitudinal opening 185b for operably receiving a latch member 188 and a biasing member 189. Biasing member 189 may include a compression spring, as shown in FIG. 15, or any other means capable of biasing the latch member 188 in a distal direction. As will be described in further detail below, the latch housing 186 further includes a pair of bores 185c for receiving a pair of locking members 252 that selectively extend from the loading unit 200 to prevent separation of the loading unit 200 from the adapter assembly 100 when the cartridge assembly 300 is received within the loading unit 200.

The distal body portion 104 of the adapter assembly 100 operably supports the drive assembly 190 of the adapter assembly 100. The drive assembly 190 includes a drive gear assembly 192 rotatably received about the pivot pin 187. The drive gear assembly 192 includes a primary drive gear 192a and a secondary drive gear 192b fixedly secured relative to the primary drive gear 192a such that the secondary drive gear 192b rotates as the primary drive gear 192a is rotated. The drive gear assembly 190 further includes a rotation drive gear 194 for causing rotation of the cylindrical housing 182 and the latch housing 186 relative to the distal connector housing 108 of the distal body portion 104. When the loading unit 200 is secured to the latch housing 182, rotation of the drive gear 194 causes rotation of the loading unit 200.

As shown in FIG. 18, the primary drive gear 192a of the drive gear assembly 192 engages the first spur gear 174 mounted on the second end 170b of the first distal bevel gear 170 of the drive transfer assembly 160 (FIG. 15). Rotation of the first spur gear 174, as described above, causes rotation of the primary and secondary drive gears 192a, 192b. The latch housing 186 is configured such that a portion of the secondary drive gear 192b is exposed. As will be described in further detail below, when the loading unit 200 is secured to the latch housing 186 of the distal body portion 104 of the adapter assembly 100, the secondary drive gear 192*b* engages a drive gear 238 (FIG. 20) of an actuation assembly 230 (FIG. 20) of the loading unit 200 to enable actuation of the loading unit 200.

With continued reference to FIG. 18, the rotation drive gear 194 engages the second spur gear 176 mounted on the second end 172*b* of the second distal bevel gear 170 of the drive transfer assembly 160 (FIG. 15) and the toothed surface 182*a* of cylindrical housing 182. Rotation of the second spur gear 176, as described above, causes rotation of the rotation drive gear 194 which causes the rotation of the cylindrical housing 182 and the latch housing 186 and further causes rotation of the loading unit 200 secured to the latch housing 186.

As shown in FIG. 18, the primary drive gear 192*a* of the drive gear assembly 192 and the first spur gear 174 for driving the primary drive gear 192, as well as the rotation drive gear 194 and the second spur gear 172 for driving the rotation drive gear 194 are disposed within the same cross-sectional plane of the distal body portion 104. This compact design of the drive transfer assembly 160 and the drive assembly 190 and the location of the power transmission within the articulation joint 105 allows for a shortened length of the distal body portion 104. The shortened length of the distal body portion 104 allows for increased manipulability of an end effector, e.g., the loading unit 200, during a surgical procedure.

As shown, the length of the distal body portion 104 is substantially equal to the diameter of the distal body portion 104. Alternatively, the length of the distal body portion 104 may be less than the diameter of the distal body portion 104. In this manner, the secondary drive gear 192*b* of the drive gear assembly 192 is disposed within one diameter length of the articulation joint 105. For example, if the diameter of the distal body portion 104 is fifteen millimeters (15 mm), the distance between the pivot pin 107 of the articulation joint 105 and the primary drive gear 192*a* is less than fifteen millimeters (15 mm). In embodiments, the distance between the pivot pin 107 and the secondary drive gear 192*b* is between five millimeters (5 mm) and thirty millimeters (30 mm), and more specifically, between ten millimeters (10 mm) and twenty millimeters (20 mm).

The loading unit 200 and the cartridge assembly 300 will be described with reference to FIGS. 19-31. The loading unit 200 includes a carrier 210, an anvil assembly 220, an actuation assembly 230, and a locking mechanism 250. The carrier 210 and an anvil member 222 of the anvil assembly 220 are pinned together by a pair of pins 222*a*, 222*b* and are movable between open (FIG. 4) and closed (FIG. 19) positions. The anvil member 222 is biased to the open position by a leaf spring 204. The carrier 210 defines a longitudinal recess 211 for operably supporting the actuation assembly 230 and selectively receiving the cartridge assembly 300. Optionally, an insert or pad 206 is received with the longitudinal recess 211 of the carrier 210 between the carrier 210 and the cartridge assembly 300 to reduce the friction between a drive beam 240 of the actuation assembly 230 and the carrier 210 during operation of the loading unit 200. An electrical contact member 208 is supported in the carrier 210 and is in electrical communication with the handle assembly 10 (FIG. 1) through the adapter assembly 100 (FIG. 1) when the loading unit 200 is secured to the adapter assembly 100.

Figure 23:
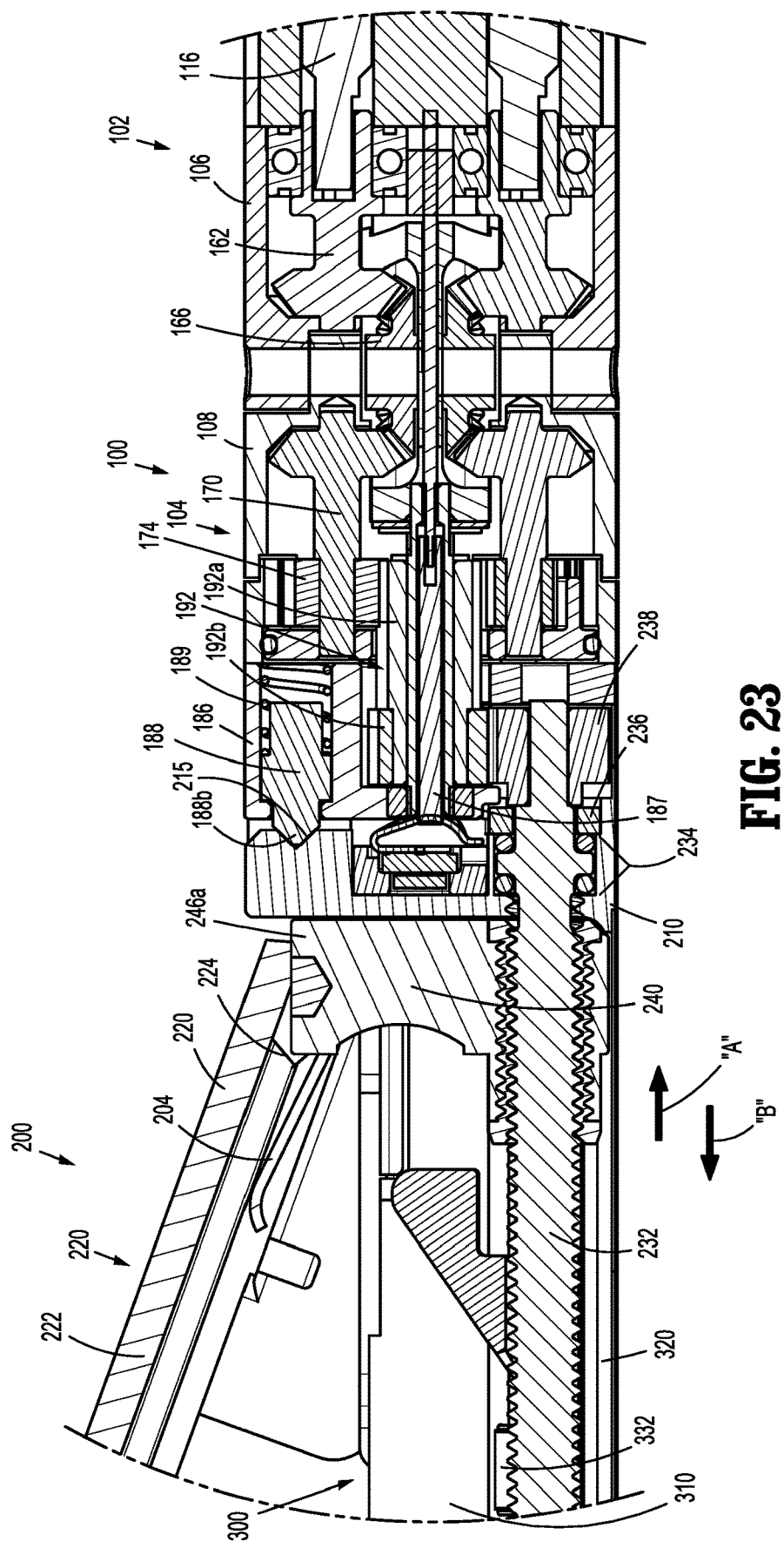
FIG. 23 is an enlarged view of the indicated area of detail shown in FIG. 4.

With particular reference now to FIGS. 21-23, a proximal end of the carrier 210 is configured to selectively secure loading unit 200 to adapter assembly 100. Specifically, the carrier 210 includes an extension 212 that engages the latch housing 186 of adapter assembly 100. The extension 212 defines a cutout 213 for receiving the tongue 186*a* of the latch housing 186 of the adapter assembly 100. The extension 212 further defines a pair of notches 213 for receiving the lips 186*b* of the latch housing 186 of the adapter assembly 100. The extension 212 still further defines a recess 215 (FIG. 23) for receiving the distal end 188*b* of the latch member 188 of the latch mechanism 180 of the adapter assembly 100 when the loading unit 200 is engaged with the adapter assembly 100 for frictionally securing the loading unit 200 to the adapter assembly 100. The extension 212 also defines a pair of longitudinal bores 217 (FIG. 29) for operably receiving locking members 252 and biasing members 254 of a locking mechanism 250, as will be described below.

With particular reference to FIGS. 21 and 22, the loading unit 200 is secured to the adapter assembly 100 by aligning the tongue 186*a* of the latch housing 186 of the adapter assembly 100 with the cutout 213 of the carrier 210 of the loading unit 200 and the lips 186*b* of the latch housing 186 of the adapter assembly 100 with the notches 215 of the carrier 210 of the loading unit 200 and moving the loading unit 200 relative to the adapter assembly 100. The tongue 186*a* and lips 186*b* of the latch housing 186 are received within the respective cutout 213 and notches 215 until the distal end 188*b* of the latch member 188 of the adapter assembly 100 aligns with and is subsequently received within the recess 215 in the carrier 210 of the loading unit 200. The distal end 188*b* of the latch member 188 may be conical, as shown in FIG. 21, to facilitate retraction of the latch member 188 within the second longitudinal opening 185*b* of the latch housing 186 against the bias of biasing member 189 (FIG. 23) as the tongue 186*a* and lips 186*b* of the latch housing 186 are received within the respective cutout 213 and notches 215 in the carrier 210 of the loading unit 200.

The receipt of the distal end 188*b* of the latch member 188 in the recess 215 of the carrier 210 of the loading unit 200 frictionally secures the loading unit 200 with the adapter assembly 100. The receipt of the distal end 188*b* of the latch member 188 in the recess 215 may produce a tactile and/or audible feedback to the user indicating that the loading unit 200 is securely attached to the adapter assembly 100. Prior to the cartridge assembly 300 (FIG. 30) being received within the longitudinal recess 211 of the carrier 210 of the loading unit 200 and/or once the cartridge assembly 300 has been removed from the carrier 210, the loading unit 200 may be separated from the adapter assembly 100 by overcoming the friction force provided by the latch member 188 of the latch mechanism 180.

With continued reference to FIG. 20-23, the actuation assembly 230 of the loading unit 200 includes a lead screw 232 rotatably supported within the carrier 210 by a bearing assembly 234 and a bearing member 236. A drive gear 238 is supported on a proximal end 232*a* of the drive screw 232 between the bearing assembly 234 and the bearing member 236. The drive gear 238 engages the secondary drive gear 192*b* (FIG. 21) of the adapter assembly 100 when the loading unit 200 is secured to the adapter assembly 100 and functions to transfer the rotational motion from the secondary drive gear 192*b* to the drive screw 232 of the loading unit 200. A distal end 232*b* of the drive screw 232 is threaded and supports a drive beam 240 thereon.

Figure 19:
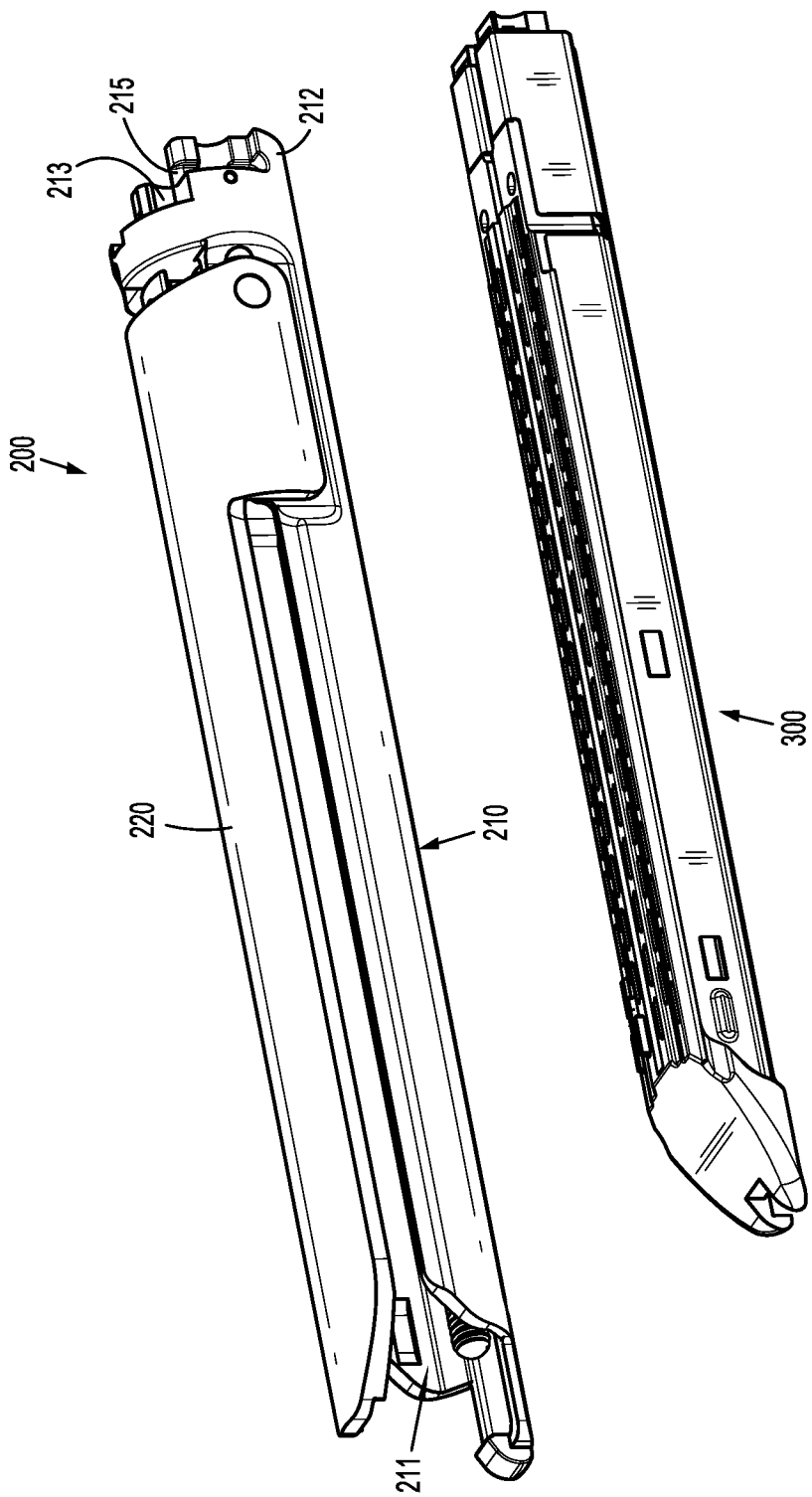
FIG. 19 is a perspective side view of the loading unit and the cartridge assembly shown in FIG. 1.
Figure 20:
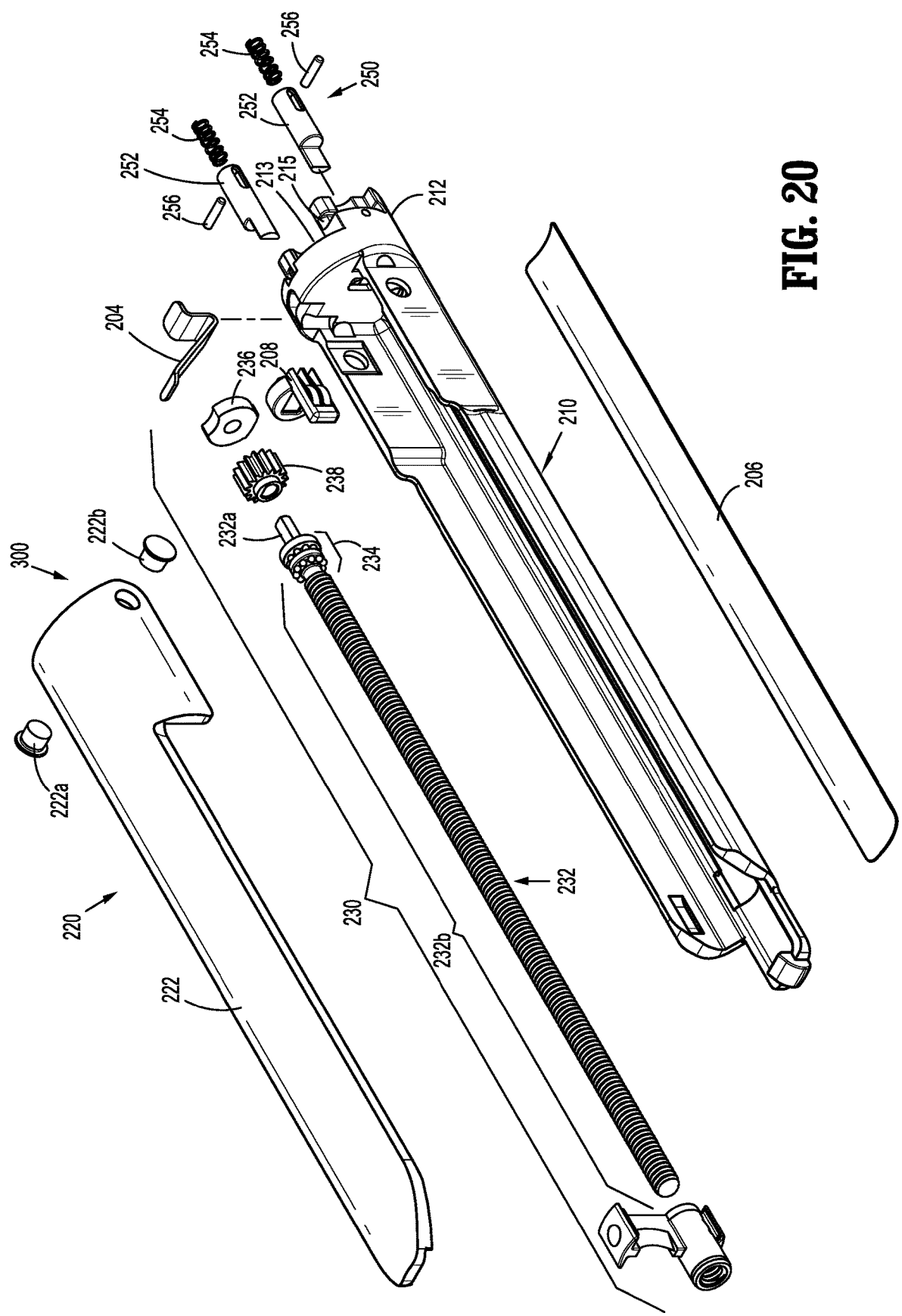
FIG. 20 is an exploded perspective view of the loading unit shown in FIG. 1.

Turning briefly to FIGS. 24-26, the drive beam 240 of the loading unit 200 includes a retention portion 242 and a vertical support portion 244. The retention portion 242 of the drive beam 240 is configured for threaded engagement with the threaded distal end 232b of the drive screw 232 (FIG. 20). A flange 242a formed on the retention portion 242 of the drive beam 240 maintains the drive beam 240 in a vertical orientation relative to the carrier 210 (FIG. 20) and the staple cartridge 300 (FIG. 19). The vertical support portion 244 of the drive beam 240 includes a cam member 246a and a knife member 246b. The cam member 246a is formed on a free end of the vertical support portion 244 of the drive beam 240 and is configured for selective engagement with a ledge 224 (FIG. 23) of the anvil member 222 of the anvil assembly 220. As will be described in further detail below, engagement of the cam member 246a of the drive beam 240 with the ledge 224 of the anvil member 222 causes anvil member 222 to move from the open position (FIG. 4) to the closed position (FIG. 19) and maintains the anvil member 222 in the closed position. The knife member 246b of the vertical support portion 244 of the drive beam 240 is configured to cut the tissue (not shown) clamped between the cartridge assembly 300 (FIG. 19) and the anvil member 222 (FIG. 19) during actuation of the loading unit 200.

In embodiments, and as shown, the drive beam 240 is formed of metal, e.g., stainless steel, or other suitable material. The retention portion 242 and the cam member 246a of the drive beam 240 each include a molded insert 243, 247, respectively, formed of plastic, e.g., peek, or other suitable material. The molded inserts 243, 247 are co-molded with the respective retention portion 242 and the cam member 246a of the drive beam 240. The molded insert 243 includes wings 243a formed on upper surfaces of the flange 242a of the retention portion 242 on either side of the retention portion 242. The wings 243a operate to reduce the friction between the drive member 240 and the carrier 210 of the loading unit 200, thereby reducing the input torque necessary to advance the drive beam 240 through the carrier 210. Similarly, the molded insert 247 includes wings 247a on an undersurface of the cam member 246a on either side of the vertical support portion 244 of the drive beam 240. The wings 247a reduce friction between the drive beam 240 and the anvil member 222, thereby reducing the input torque necessary to advance the drive beam 240 through the carrier 210 of the loading unit 200. The stainless steel portions of the drive member 240 provide sufficient strength to support the loads required to clamp and fire a plurality of staples (not shown).

As shown in FIG. 25, in addition to the threads provided in the molded insert 243, the retention portion 242 of the drive beam 240 is also provided with threads. The threads of the retention portion 242 correspond to the threads of the molded insert 243 and operate to reinforce the threads of the molded insert. In this manner, the threads of the retention portion 242 strengthen the engagement between the drive beam 240 and the lead screw 232, thereby reducing the likelihood of failure during operation of the loading unit 200.

Turning to FIG. 26, the molded insert 243 of the drive beam 240 is provided with anti-rotation features 243b. The anti-rotation features 243a extends through flange 242a of retention portion 242 to fix molded insert 243 within retention portion 242 and prevent rotation of the molded insert 243 during advancement and retraction of the drive beam 240. With particular reference now to FIG. 23, the loading unit 200 may be provided to the surgeon with the anvil member 222 of the anvil assembly 200 in the open position (FIG. 4) or in the closed position (FIG. 19). When provided to the surgeon in the closed position, following attachment of the loading unit 200 to the adapter assembly 100, the loading unit 200 is moved the open position to permit loading of the cartridge assembly 300 within the longitudinal recess 211 of the carrier 210. As noted above, the anvil member 222 of the loading unit is maintained in the closed position through engagement of the cam member 246a of the drive member 240 with the ledge 224 of the anvil member 222. Accordingly, to move the loading unit 200 to the open position the drive beam 240 is moved proximally, i.e., retracted, as indicated by arrow "A" in FIG. 23, to disengage the cam member 246a of the drive beam 240 from the ledge 224 of the anvil member 222.

As described above, the drive beam 240 is translated longitudinally relative to the drive screw 232 by rotating the first drive shaft 116, which rotates the first proximal bevel gear 162, which rotates the first horizontal bevel gear 166, which rotates the first distal bevel gear 170, which rotates of the first spur gear 174, which rotates the primary drive gear 192a thereby rotating the secondary drive gear 192b, which rotates the drive gear 238 of the loading unit 200, which rotates the drive screw 232 to move the drive beam 240. Rotation of the first drive shaft 116 in a first direction causes the drive beam 240 to move in the proximal direction and rotation of the first drive shaft 116 in the second direction causes the drive beam 240 to move in a distal direction, i.e., advance, as indicated by arrow "B" in FIG. 23.

Proximal movement of the drive beam 240 causes the cam member 246a of the drive beam 240 to disengage from the ledge 224 of the anvil member 222. Once the cam member 246a of the drive beam disengages the anvil member 222, the leaf spring 204 biases the anvil member 222 to the open position. Once open, the cartridge assembly 300 is received within the longitudinal passage 211 of the carrier 210 of the loading unit 200.

The loading unit 200 may then be received through an access port (not shown) and positioned about tissue to be stapled (not shown) in a traditional manner. At any point during the stapling procedure, as described in detail above, the loading unit 200 may be articulated relative to the proximal body portion 102 of the adapter assembly 100 and/or the loading unit 200 may be rotated about the longitudinal axis "x" of the adapter assembly 100 for positioning the loading unit 200.

With reference still to FIG. 23, once tissue to be stapled (not shown) is received between the anvil member 222 of the anvil assembly 220 and the cartridge member 310 of the cartridge assembly 300, rotation of the first drive shaft 116 of the adapter assembly 100 in a second direction causes the drive beam 240 of the loading unit 200 to move distally. As the drive beam 240 moves distally, the cam member 246a of the drive beam 240 engages the ledge 224 of the anvil member 220 to cause the closing of anvil member 220. Continued distal movement of the drive beam 240 effects movement of an actuation sled 330 of the cartridge assembly 300 into pusher members 332 to cause the stapling of tissue (not shown). As the drive member 240 is moved distally, the knife member 246b engages and cuts the stapled tissue (not shown). Once the tissue (not shown) is stapled and cut, the drive beam 240 is retracted through rotation of the first drive shaft 116 in the first direction, as described above.

The loading unit 200 may then be removed from the patient and the spent cartridge assembly 300 may be separated or unloaded from the carrier 210. Once the spent cartridge assembly 300 is separated from the carrier 210, the loading unit 200 may be separated from the adapter assembly 100 and discarded. Alternatively, a new cartridge assembly 300 may be attached to or loaded into the loading unit 200 to permit reuse of the loading unit 200.

Figure 29:
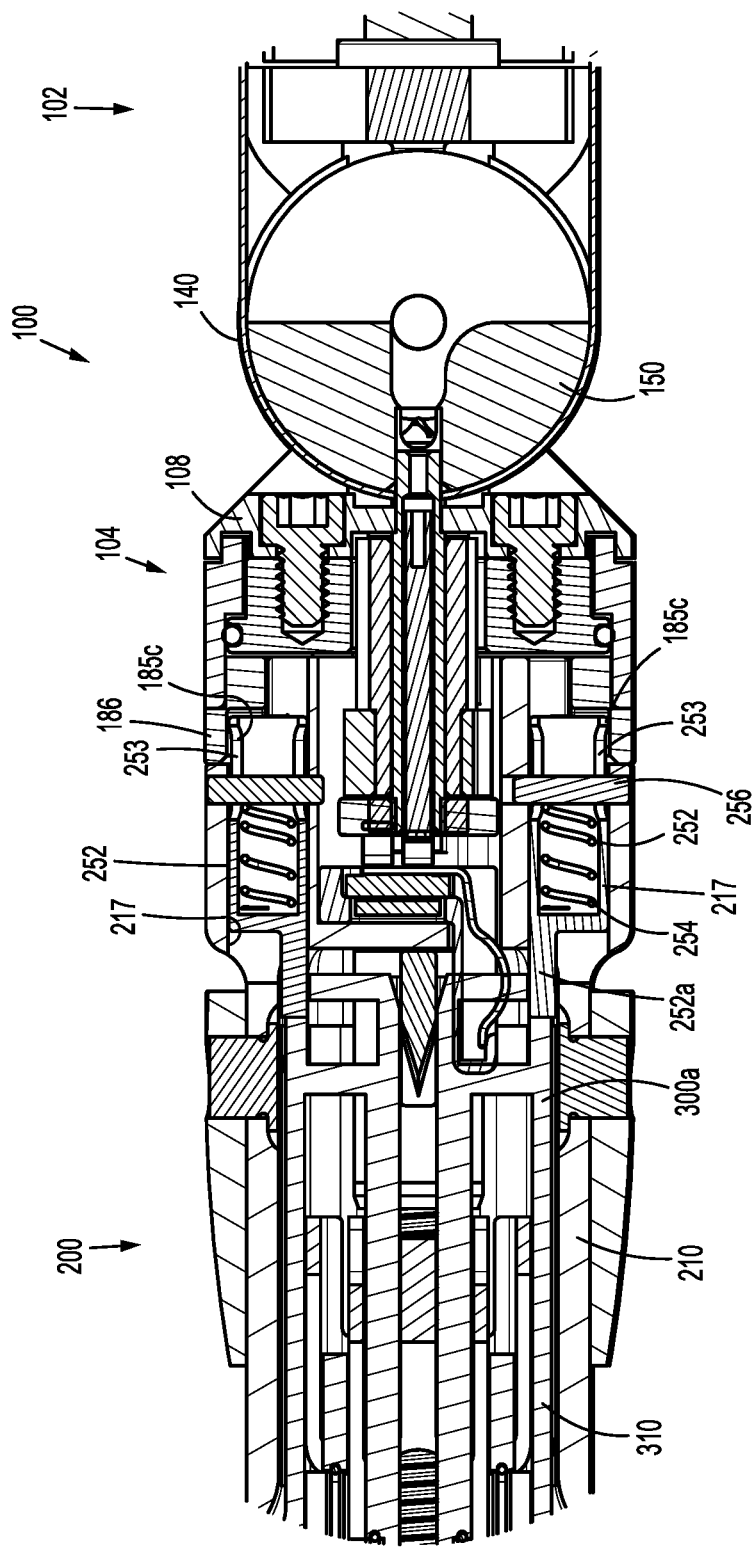
FIG. 29 is an enlarged view of the indicated area of detail shown in FIG. 12.
Figure 30:
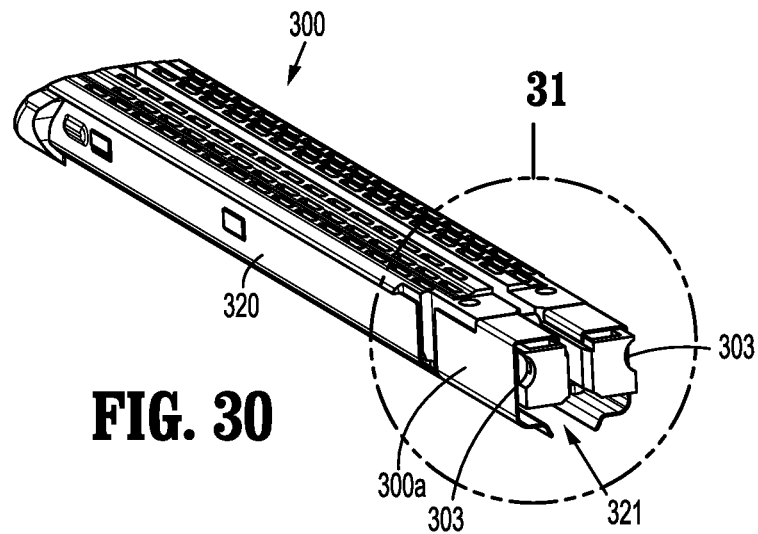
FIG. 30 is a perspective end view of the cartridge assembly shown in FIG. 1.
Figure 31:
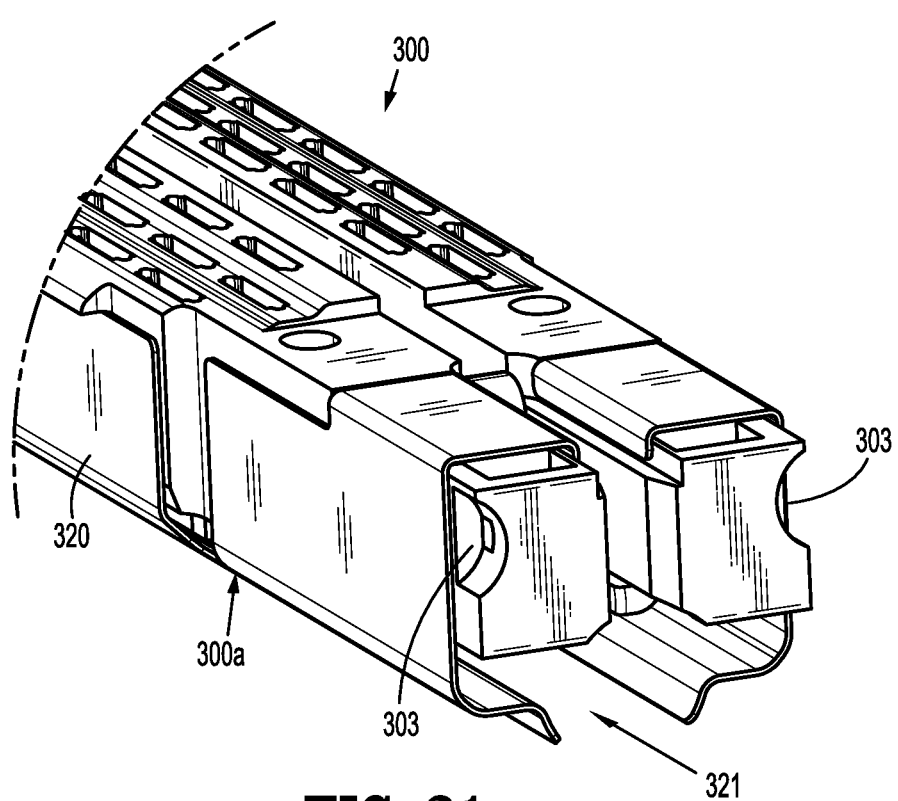
FIG. 31 is an enlarged view of the indicated area of detail shown in FIG. 30.

With reference now to FIGS. 27-31, as noted above, the loading unit 200 includes a locking mechanism 250 for preventing separation of the loading unit 200 from the adapter assembly 100 when the cartridge assembly 300 is secured within the loading unit 200. The locking mechanism 250 includes a pair of locking member 252 and a pair of biasing members, i.e., springs 254, received within the locking members 252. Pins 256 extend through slots 253 in the locking members 252 to retain the biasing members 254 about the locking members 252 and to support the locking members 252 within the longitudinal bores 217 of the extension 212 of the carrier 210. The locking members 252 include distal projections 252a that extend into the longitudinal recess 211 of the carrier 210 and engage a proximal end 300a of the cartridge assembly 300 when the cartridge assembly 300 is operably secured to the carrier 210. As shown in FIG. 31, a proximal end of a cartridge body 310 of the cartridge assembly 300 includes a pair of notches 313 for receiving the distal projections 252a of the locking members 252.

With particular reference now to FIG. 27, when the locking mechanism 250 is in a first position, i.e., prior to the cartridge assembly 300 being received within the longitudinal recess 211 of the carrier 210 of the loading unit 200, the locking members 252 are in a distal-most position. When in the distal-most position, the loading unit 200 is separable from the adapter assembly 100, as described above.

Turning to FIGS. 28 and 29, when the cartridge assembly 300 is received within the longitudinal recess 211 of the carrier 210, the proximal end 300a of the cartridge assembly 300 engages the distal projections 252a of the locking members 252 causing the locking members 252 to move in a proximal direction, as indicated by arrow "C" in FIG. 28, and into the bores 185c of the latch housing 186 of the adapter assembly 100. Receipt of the locking member 252 within the bores 185c of the latch housing 186 secure the loading unit 200 to the adapter assembly 100 and prevent the loading unit 200 from accidently detaching from the adapter assembly 100 during operation of the loading unit 200.

Turning briefly to FIGS. 30 and 31, the cartridge assembly 300 includes the cartridge body 310 and a cartridge housing 320. The cartridge housing 320 securely receives the cartridge body 310 and defines a longitudinal slot 321 for receiving the drive screw 232 of the actuation assembly 230 of the loading unit 200 therethrough. As noted above, the cartridge assembly 300 further includes the actuation sled 330 and the pusher members 332. For a detailed description of an exemplary cartridge assembly, please refer to commonly owned U.S. patent application Ser. No. 14/257,063 filed Apr. 21, 2014, entitled "Adapter Assembly with Gimbal for Interconnecting Electromechanical Surgical Devices and Surgical Loading Units, and Surgical Systems Thereof," the entire content of which is incorporated herein by reference in its entirety.

With reference now to FIGS. 32-40, an adapter assembly in accordance with another embodiment of the present disclosure, shown generally as adapter assembly 400, and a loading unit according to another embodiment of the present disclosure, shown generally as loading unit 500, are configured for selective connection to the handle assembly 10 (FIG. 1). The adapter assembly 400 is configured for selective connection with the handle assembly 10, and, the loading unit 500 is configured for selective connection with the adapter assembly 400. As will be shown and described in detail below, the loading unit 500 is a single use loading unit configured to fixedly receive a cartridge assembly 600; however, it is envisioned that the loading unit 500 may be modified to receive a replaceable cartridge assembly (not shown).

The adapter assembly 400, the loading unit 500 and the cartridge assembly 600 operate to staple and cut tissue. The adapter assembly 400 and the loading unit 500 are substantially similar to the adapter assembly 100 and the loading unit 200 described hereinabove, and therefore, will only be described to the extent necessary to detail the differences therebetween.

Figure 32:
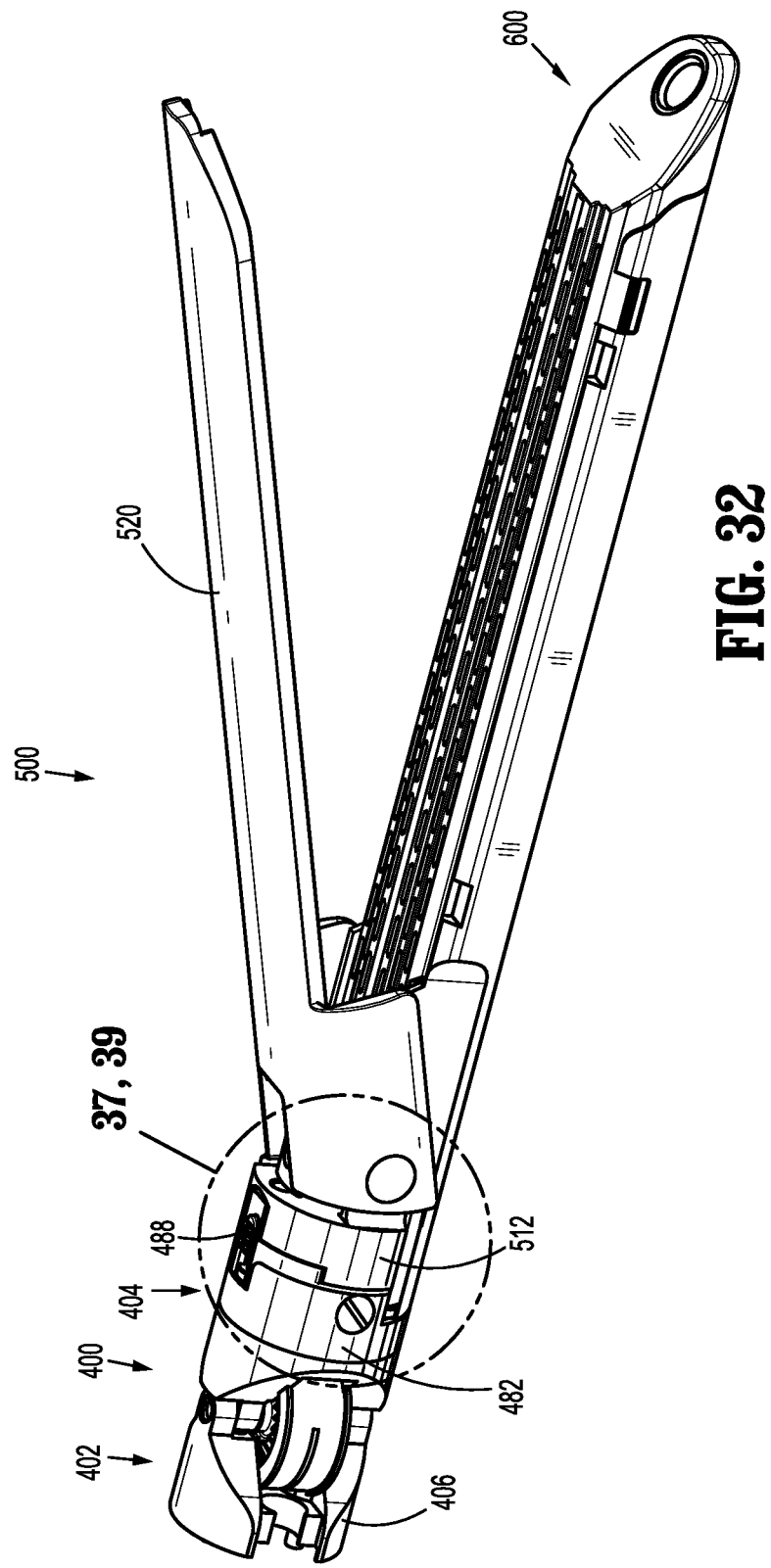
FIG. 32 is a perspective side view of an alternative embodiment of a distal end of an adapter assembly and loading unit according to the present disclosure.

With reference initially to FIG. 32, a proximal body portion 402 (only a proximal connector housing 406 shown) and a distal body portion 404 of the adapter assembly 400 are substantially the same as the proximal body portion 102 (FIG. 3) and the distal body portion 404 (FIG. 3), respectively, of the adapter assembly 100 (FIG. 3) described hereinabove. Accordingly, the proximal and distal body portions 402, 404 will only be described in detail to the extent necessary to distinguish the differences therebetween.

Figure 33:
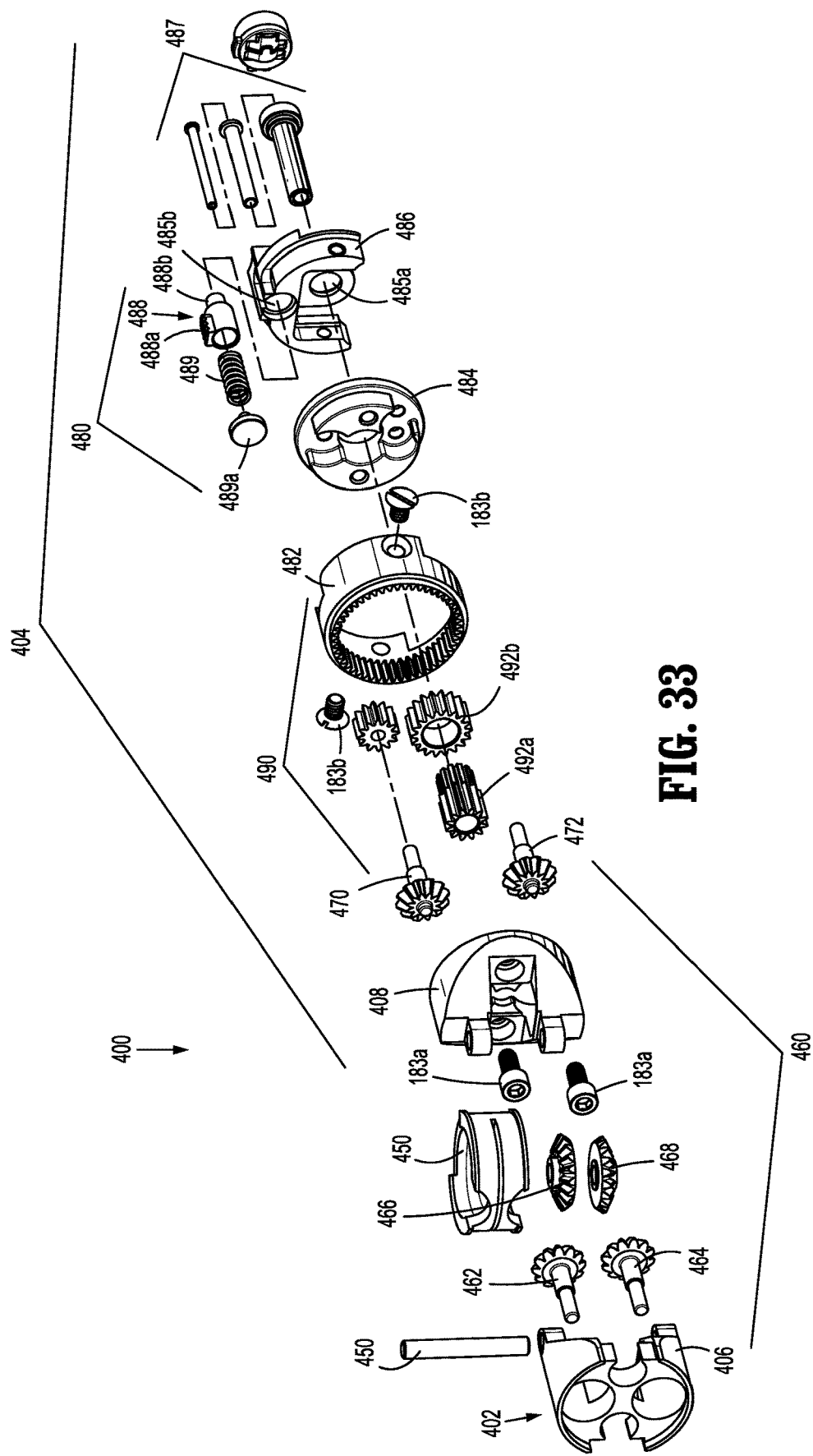
FIG. 33 is an exploded perspective side view of the proximal end of the adapter assembly shown in FIG. 32.
Figure 35A:
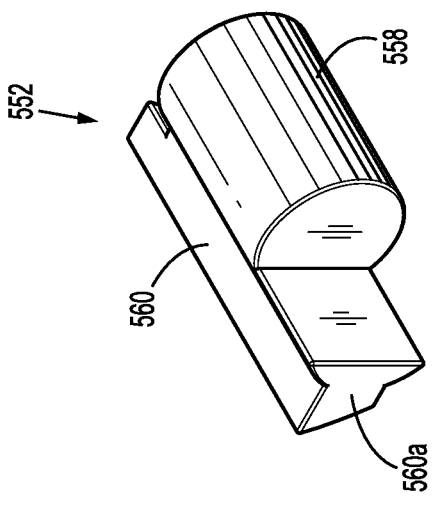
FIG. 35A is a perspective end view of a plunger member of the loading unit shown in FIG. 32.
Figure 35B:
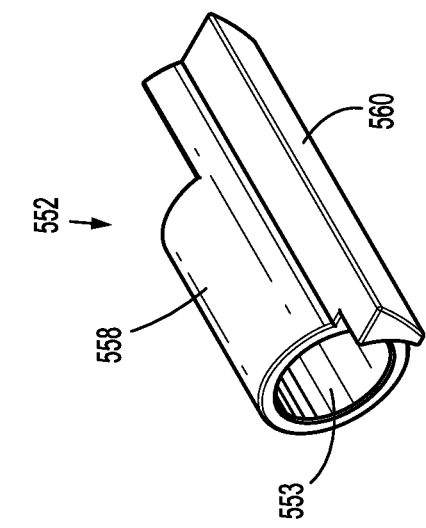
FIG. 35B is another perspective end view of the plunger member shown in FIG. 35A.
Figure 36:
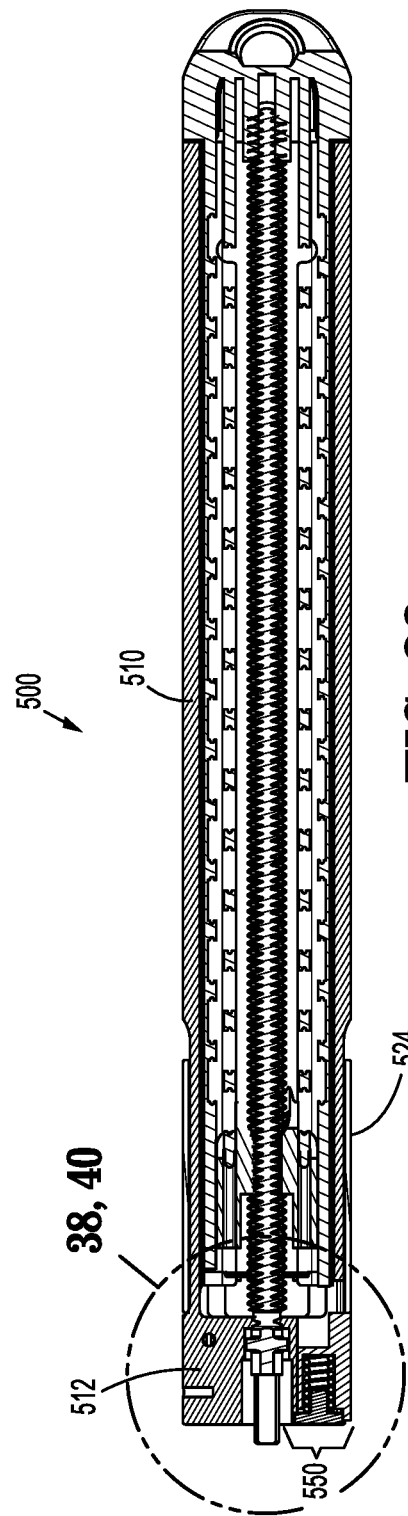
FIG. 36 is a cross-sectional top view of the loading unit shown in FIG. 32.

With reference now to FIGS. 32 and 33, a distal connector housing 408 of the distal body portion 404 is pivotally connected relative to the proximal connector housing 406 of the proximal body portion 402 by a pivot member 450. The adapter assembly 400 includes a drive transfer assembly 460 operably supported within proximal and distal connector housings 406, 408, and a drive assembly 490 operably supported within and extending through a cylindrical housing 482, support plate 484, and latch housing 486 of distal body portion 404. The support plate 484 is secured to the distal connector housing 408 by a pair of screws 483a and the latch housing 486 is secured to the cylindrical housing 482 by a pair of screws 483b. Alternatively, the support plate 484 and distal connector housing 408 and/or the latch housing and the cylindrical housing 482 may be secured to each other in any suitable manner, e.g., threading, friction fit, mechanical fasteners.

With particular reference to FIG. 33, briefly, the drive transfer assembly 460 includes first and second proximal bevel gears 462, 464, first and second horizontal bevel gears 466, 468, and first and second distal bevel gears 470, 472. The drive gear assembly 490 includes a primary drive gear 492a and a secondary drive gear 492b fixedly secured relative to the primary drive gear 492a, and a rotation drive gear (not shown). For a detailed description of the operation of the drive transfer assembly 460 and drive gear assembly 490, please refer to the drive transfer assembly 160 (FIG. 15) and the drive gear assembly 190 (FIG. 15) of adapter assembly 100 described hereinabove.

With continued reference to FIGS. 32 and 33, the latch housing 486 of the distal body portion 404 of the adapter assembly 400 is configured for selective connection with the loading unit 500 (FIG. 32). The latch housing 486 defines a first longitudinal opening 485a for receiving a bearing assembly 487 and a second longitudinal opening 485b for operably receiving a latch mechanism 480. The bearing assembly 487 rotatably supports the drive gear assembly 490 and the latch mechanism 480 selectively secures the loading unit 500 to the distal body portion 404 of the adapter assembly 400.

The latch mechanism 480 includes a latch member 488, a biasing member 489, and a cap member 489a for retaining the latch member 488 and the biasing member 489 within the second longitudinal opening 485b. The latch member 488 includes a proximal portion 488a configured for operable engagement by a user and a distal portion 488b configured to be selectively received within a recess 515 (FIG. 34) defined in an extension 512 of a carrier 510 of loading unit 500. The latch mechanism 480 operates to selective secure the loading unit 500 to the distal body portion 404 of the adapter assembly 400. Specifically, the biasing member 489 of the latch mechanism 480 biases the distal portion 488b of the latch member 488 into the recess 515 formed in the extension 512 of the carrier 510 of loading unit 500 when the loading unit 500 is engaged with the latch housing 486 of the adapter assembly 400 to prevent the loading unit 500 from disengaging from the latch housing 486 of the adapter assembly 400. Proximal movement of the latch member 488, against the bias of the biasing member 489, through engagement of the proximal portion 488a of the latch member 488 retracts the distal portion 488b of the latch member 488 from within the recess 515 in the extension 512 of the carrier 510 of the loading unit 500, thereby permitting the loading unit 500 to be separated from the adapter assembly 400 in the same manner loading unit 200 is separated from adapter assembly 100, described hereinabove.

With reference now to FIG. 34, the loading unit 500 includes the carrier 510, an anvil assembly 520, an actuation assembly 530, and a plunger assembly 550. A distal end of the carrier 510 of the loading unit 500 defines a longitudinal recess 511 for receiving the staple cartridge 600. The cartridge assembly 600 may be permanently affixed within the longitudinal recess 511 of the carrier 510 such that the cartridge assembly 600 cannot be replaced, i.e., for single use, or the cartridge assembly 600 may be selectively secured with the longitudinal recess 511 of the carrier 510 to permit replacement of the cartridge assembly 600, i.e., for multiple uses. The anvil assembly 520 includes an anvil member 522 pivotally secured to the carrier 510 by a pair of pivot pins (not shown). The anvil member 522 includes a C-shaped frame portion 524. As will be described in further detail below, a proximal end 524a of C-shaped frame portion 524 is configured for operable engagement by a distal end 560a (FIG. 35B) of a longitudinal body portion 560 of a plunger member 552 of the plunger assembly 550.

Figure 40:
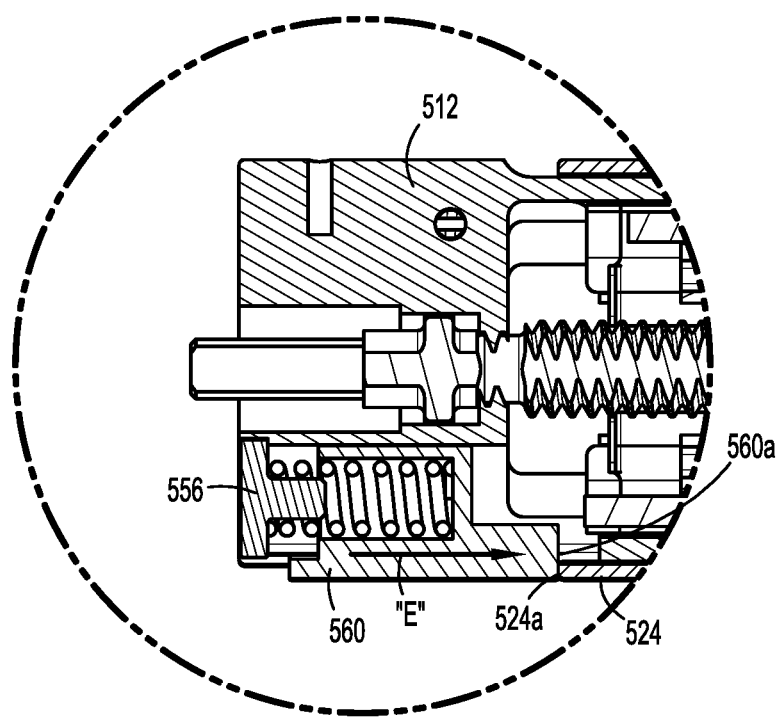
FIG. 40 is an enlarged view of the indicated area of detail shown in FIG. 36, with the anvil assembly in the opened position.

With continued reference to FIG. 34, the actuation assembly 530 includes the drive screw 532 and a drive beam 540. With additional reference to FIGS. 35A and 35B, the plunger assembly 550 is operably mounted within an extension 512 of the carrier 510 and includes a plunger member 552, a spring member 554, and an end cap 556. The plunger member 552 of the plunger assembly 550 is slidably disposed within the extension 512 of the carrier 510 of the loading unit 500 and is configured to bias the anvil member 522 of the anvil assembly 520 to an open position (FIG. 40). Specifically, the plunger member 552 includes a cylindrical body portion 558 received within a longitudinal bore 517 formed in the extension 512 of the carrier 510. A distal end 554b of the spring member 554 is received within a cylindrical recess 553 defined by the cylindrical body portion 558. The plunger member 552 and the spring member 554 are maintained within the longitudinal bore 517 of the extension 512 by the end cap 556. The end cap 556 may be secured to the extension 512 of the carrier 510 by friction fit, welding, adhesive, mechanical fasteners, or in any other suitable manner. Alternatively, the end cap 556 and the longitudinal bore 517 may be threaded or include a tab and slot arrangement for securing the end cap 556 to the extension 512 of the carrier 512.

The plunger member 552 of the plunger assembly 550 is biased in a distal direction by the spring member 554. Although shown in the form of a traditional coil spring, the spring member 554 may include any mechanism or material exhibiting elastic characteristics, e.g., pneumatic or hydraulic cylinder, rubber bumper. An elongate body portion 560 of the plunger member 552 is operably received within the longitudinal slot 319 formed in the extension 512 of the carrier 510. A distal end 560a of the elongate body portion 560 of the plunger member 552 engages the anvil member 522 of the anvil assembly 520 to bias the anvil assembly 520 to the open position (FIG. 40).

Figure 37:
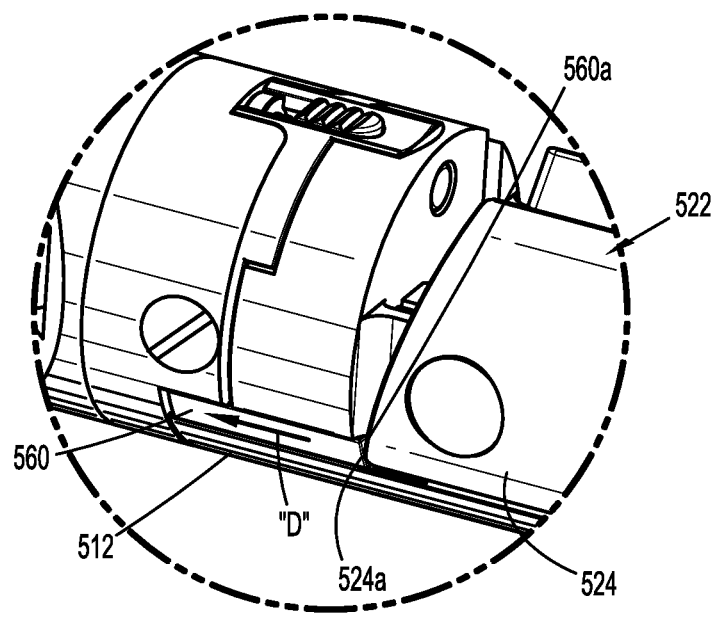
FIG. 37 is an enlarged view of the indicated area of detail shown in FIG. 32 with the anvil assembly in a closed position.
Figure 38:
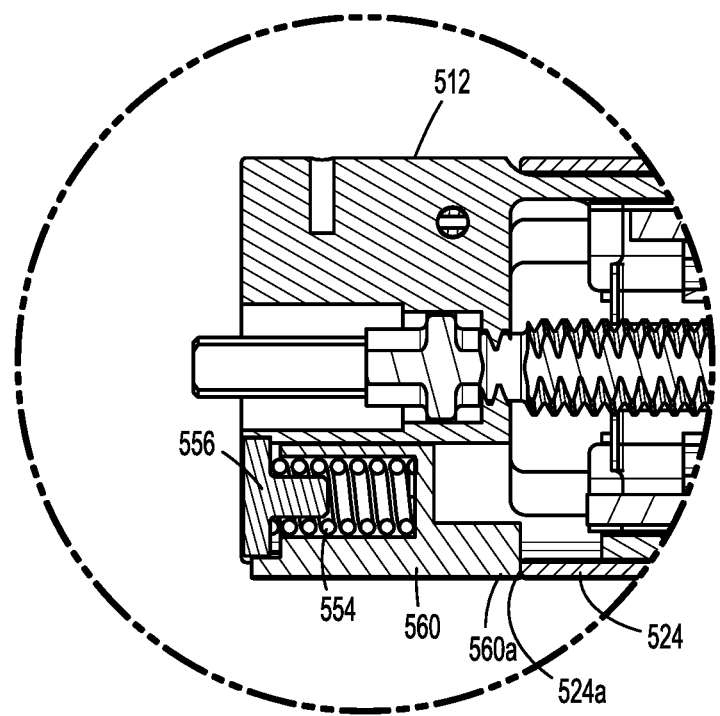
FIG. 38 is an enlarged view of the indicated area of detail shown in FIG. 36, with the anvil assembly in the closed position.

With reference now to FIGS. 37 and 38, as described above with regards to the loading unit 200, the loading unit 500 may be provided to the clinician in the closed position, the loading unit 500 may be closed prior to insertion into the body cavity (not shown) of a patient (not shown), or the loading unit 500 may be closed subsequent to positioning the tissue to be stapled (not shown) between the cartridge assembly 600 and the anvil member 522 of the anvil assembly 520. As the anvil member 522 is pivoted to the closed position, the proximal end 524a of the C-shaped frame 524 of the anvil member 522 engages the distal end 560a of the elongated body portion 560 of the plunger member 552 of the plunger assembly 550. The anvil assembly 520 may be moved to the closed position through advancement of the drive beam 540 of the actuation assembly 530 or through manual engagement of the anvil assembly 520 by the clinician. Engagement of the plunger member 552 of the plunger assembly 550 by the anvil member 522 as the anvil member 522 of the anvil assembly 520 is pivoted to the closed position causes the plunger member 552 to move in the proximal direction, as indicated by arrow "D". As plunger member 552 is moved proximally, i.e., retracted, spring member 554 of the plunger assembly 550 is compressed to provide a spring bias against anvil member 522.

Figure 39:
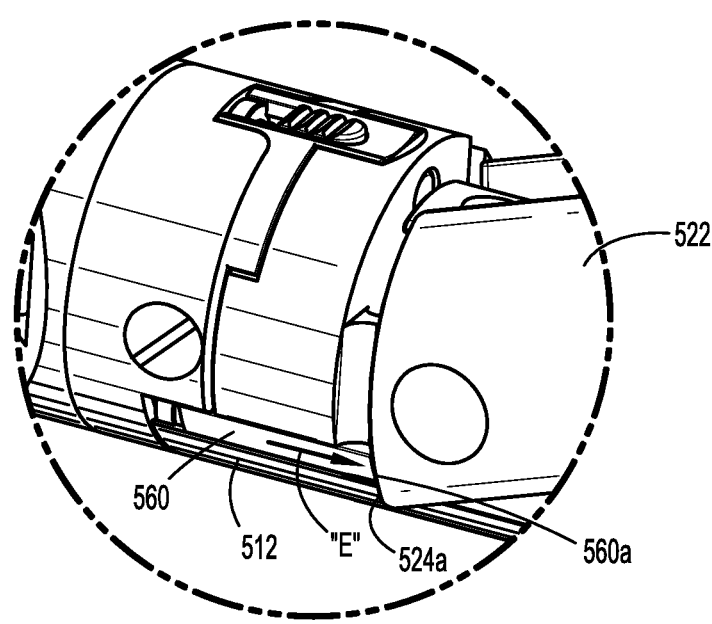
FIG. 39 is an enlarged view of the indicated area of detail shown in FIG. 32 with the anvil assembly in an opened position.

Turning now to FIGS. 39 and 40, whether the anvil assembly 520 was held closed manually by a clinician or closed through operation of the drive beam 540 of the actuation assembly 530, release of the anvil assembly 520 by the clinician or disengagement of the drive beam 540 the anvil member 522 permits the anvil assembly 520 to move to the open position. The spring bias generated by compressing spring member 554 during the closing of anvil assembly 520 acts on plunger member 552 to move the plunger member 552 in the distal direction, as indicated by arrow "E". Engagement of the distal end 560a of the elongated body portion 560 of the plunger member 552 with the proximal end 524a of the C-shaped frame 524 of the anvil member 522 to cause the pivoting of the anvil member 522 to the open position.

Upon completion of a stapling procedure, the loading unit 500 may be separated or unloaded from the adapter assembly 400 in the manner described above. Additional loading units may then be attached to the adapter assembly 400 for subsequent stapling procedures. As noted above, the loading unit 500 may be configured to receive a replaceable cartridge assembly (not shown) for permitting reuse of the loading unit 500. The adapter assembly 400 may be separated from the handle assembly 10 (FIG. 1) and discarded. Alternatively, the adapter assembly 400 may be sterilized and reused.

Any of the components described herein may be fabricated from either metals, plastics, resins, composites or the like taking into consideration strength, durability, wearability, weight, resistance to corrosion, ease of manufacturing, cost of manufacturing, and the like.

It will be understood that various modifications may be made to the embodiments of the presently disclosed adapter assemblies. Therefore, the above description should not be construed as limiting, but merely as exemplifications of embodiments. Those skilled in the art will envision other modifications within the scope and spirit of the present disclosure.

What is claimed is:

1. An adapter assembly for connecting a loading unit to a handle assembly, the adapter assembly comprising:
   a proximal body portion defining a longitudinal axis;
   a distal body portion selectively articulable relative to the proximal body portion; and
   an articulation assembly for articulating the distal body portion relative to the proximal body portion, the articulation assembly comprising:
      a pivot member fixedly secured to the distal body portion and rotatably secured relative to the proximal body portion; and
      a flexible band received about the pivot member and including first and second portions, wherein simultaneous longitudinal advancement of the first portion of the flexible band and longitudinal retraction of the second portion of the flexible band causes articulation of the distal body portion relative to the proximal body portion in a first direction.

2. The adapter assembly of claim 1, wherein the proximal body portion is configured for operable engagement with a handle assembly.

3. The adapter assembly of claim 1, wherein the distal body portion is configured for operable engagement with a loading unit.

4. The adapter assembly of claim 1, wherein the articulation assembly further includes a connector tube secured to the flexible band and a drive screw in operable engagement with the connector tube.

5. The adapter assembly of claim 4, wherein rotation of the drive screw relative to the connector tube causes longitudinal translation of the first and second portions of the flexible band.

6. The adapter assembly of claim 5, wherein rotation of the drive screw in a first direction translates the first portion of the flexible band in a first longitudinal direction to articulate the distal body portion in a first direction relative to the proximal body portion and rotation of the drive screw in a second direction translates the first portion of the flexible band in a second longitudinal direction to articulate the distal body portion in a second direction.

7. The adapter assembly of claim 5, wherein a proximal end of the drive screw is configured for operable connection with a drive shaft of a handle assembly.

8. The adapter assembly of claim 1, wherein the articulation assembly includes a tensioning mechanism for maintaining the flexible band in tension about the pivot member.

9. The adapter assembly of claim 8, wherein the tensioning mechanism operably engages proximal and distal portions of the flexible band to maintain the flexible band in tension about the pivot member.

10. The adapter assembly of claim 8, wherein the tensioning mechanism includes a tensioning housing, a tensioning screw, and a tensioning gear rotatably received within the tensioning housing, the tensioning gear operably engaging the proximal and distal portions of the flexible band to maintain the flexible band in tension about the pivot member.

11. The adapter assembly of claim 10, wherein rotation of the tensioning screw relative to the tensioning housing in a first direction increases the tension of the flexible band on the pivot member and rotation of the tensioning screw relative to the tensioning housing in a second direction reduces the tension of the flexible band on the pivot member.

12. The adapter assembly of claim 10, wherein the tensioning gear operably engages the proximal and distal portions of the flexible band to move proximal and distal portions of the flexible band relative to each other during longitudinal translation of the flexible band.

13. The adapter assembly of claim 1, further including a drive assembly extending therethrough for actuating a loading unit when the loading unit is secured to distal body portion.

14. The adapter assembly of claim 1, further including a latch mechanism operably received within distal body portion for selectively securing a loading unit to the distal body portion.

15. The adapter assembly of claim 1, further including a loading unit selectively secured to the distal body portion, wherein the loading unit includes a cartridge assembly, an anvil assembly pivotally secured relative to the cartridge assembly between an open position and a closed position, and a plunger assembly for biasing the anvil assembly to the open position.

16. The adapter assembly of claim 1, wherein the flexible band engages the pivot member.

17. An adapter assembly for connecting a loading unit to a handle assembly, the adapter assembly comprising:
   a proximal body portion defining a longitudinal axis;
   a distal body portion selectively articulable relative to the proximal body portion; and
   an articulation assembly for articulating the distal body portion relative to the proximal body portion, the articulation assembly comprising:
      a pivot member fixedly secured to the distal body portion and rotatably secured relative to the proximal body portion; and
      a flexible band received about the pivot member and including first and second portions, wherein longitudinal advancement of first portion of the flexible band causes articulation of the distal body portion relative to the proximal body portion in a first direction and advancement of the second portion of the flexible band causes articulation of the distal body portion relative to the proximal body portion in a second direction.

* * * * *